(12) United States Patent
Purschke et al.

(10) Patent No.: US 10,093,934 B2
(45) Date of Patent: *Oct. 9, 2018

(54) SDF-1 BINDING NUCLEIC ACIDS AND THE USE THEREOF IN CANCER TREATMENT

(71) Applicant: NOXXON Pharma AG, Berlin (DE)

(72) Inventors: Werner Purschke, Berlin (DE); Florian Jarosch, Berlin (DE); Dirk Eulberg, Berlin (DE); Sven Klussmann, Berlin (DE); Klaus Buchner, Berlin (DE); Christian Maasch, Berlin (DE); Nicole Dinse, Berlin (DE); Dirk Zboralski, Berlin (DE)

(73) Assignee: NOXXON Pharma AG, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/201,477

(22) Filed: Jul. 3, 2016

(65) Prior Publication Data

US 2016/0355821 A1 Dec. 8, 2016

Related U.S. Application Data

(63) Continuation of application No. 14/947,173, filed on Nov. 20, 2015, now Pat. No. 9,387,221, which is a continuation of application No. 13/821,669, filed as application No. PCT/EP2011/004554 on Sep. 9, 2011.

(30) Foreign Application Priority Data

Sep. 9, 2010 (EP) .................................... 10009379

(51) Int. Cl.

| | | |
|---|---|---|
| *C12N 15/115* | (2010.01) | |
| *A61K 31/7088* | (2006.01) | |
| *A61K 31/7105* | (2006.01) | |
| *A61K 45/06* | (2006.01) | |
| *A61K 31/69* | (2006.01) | |
| *A61K 35/12* | (2015.01) | |
| *A61K 31/713* | (2006.01) | |
| *A61K 31/7076* | (2006.01) | |

(52) U.S. Cl.
CPC ............. *C12N 15/115* (2013.01); *A61K 31/69* (2013.01); *A61K 31/7076* (2013.01); *A61K 31/7088* (2013.01); *A61K 31/713* (2013.01); *A61K 31/7105* (2013.01); *A61K 35/12* (2013.01); *A61K 45/06* (2013.01); *C12N 2310/16* (2013.01); *C12N 2310/30* (2013.01); *C12N 2310/351* (2013.01); *C12N 2320/30* (2013.01); *C12N 2320/31* (2013.01)

(58) Field of Classification Search
None
See application file for complete search history.

(56) References Cited

U.S. PATENT DOCUMENTS

| | | |
|---|---|---|
| 5,582,981 A | 12/1996 | Gilead |
| 5,840,867 A | 11/1998 | Gilead |
| 7,282,338 B2 | 10/2007 | Chemocentryx |
| 7,396,653 B2 | 7/2008 | Chemocentryx |
| 7,468,253 B2 | 12/2008 | Chemocentryx |
| 8,119,126 B2 | 2/2012 | Chugai |
| 8,314,223 B2 | 11/2012 | Purschke et al. |
| 8,772,257 B2 | 7/2014 | Purschke et al. |
| 9,387,221 B2 * | 7/2016 | Purschke ............ A61K 31/7088 |

OTHER PUBLICATIONS

Sayyed et al., "Podocytes . . . diabetes," Diabet 52:2445-2454, 2009.
Hachet-Haas et al., JBC 280(34)23189-238199, 2008.
Otsuka et al., J Thorac Oncol 3:1379-1383, 2008.
Vaday et al., Clin Cancer Res 10:5630-5639, 2004.
Curran et al., Drugs 69(7)859-888, 2009.
Gelboin et al., Chem Res Tox 9:1023-1030, 1996.
Li et al., "Retina-committed . . . retina," Ann Meeting Assoc Res Vision 46, Supp 8, 3247, 2005.
Luker & Luker, "Functions of . . . cancer," Canc Lett 238, 30-41, 2006.
Smith et al., Porcine EST collection, Genbank, XP002465983, 2004.
Burger & Kipps, "CXCR4: a key . . . microenvironment," Blood 107(5)1761-1767, 2006.
Kucia et al., "CXCR4-SDF-1 . . . adhesion," J Mol Hist 35:233-245, 2004.
Chalasani et al., "A chemokine . . . pathfinding," K Neurosci 23(4)1360-1371, 2003.

* cited by examiner

*Primary Examiner* — Richard A Schnizer
(74) *Attorney, Agent, or Firm* — MDIP LLC

(57) ABSTRACT

The present invention is related to a nucleic acid molecule capable of binding to SDF-1, preferably capable of inhibiting SDF-1, whereby the nucleic acid molecule is for use in a method for the treatment and/or prevention of a disease or disorder, for use in a method for the treatment of a subject suffering from a disease or disorder or being at risk of developing a disease or disorder as an adjunct therapy, or for use as a medicament for the treatment and/or prevention of a disease or disorder, whereby the disease or disorder is cancer.

18 Claims, 21 Drawing Sheets
Specification includes a Sequence Listing.

Type A SDF-1 binding nucleic acids

| SEQ ID NO | Name | nt. | Sequence: 5'-3' | Comp. |
|---|---|---|---|---|
| 60/146 | 192-A10-001 | 38 | GCUGUG AAAGCAACAUGUCAA-UGAAAGGUAGC CGCAGC | |
| 61/147 | 192-G10 | 38 | GCUGUG AAAGUAACAUGUCAA-UGAAAGGUAAC CACAGC | < |
| 62/148 | 192-F10 | 38 | GCUGUG AAAGUAACACGUCAA-UGAAAGGUAAC CGCAGC | < |
| 63/149 | 192-B11 | 38 | GCUGUG AAAGUAACACGUCAA-UGAAAGGUAAC CACAGC | = |
| 64/150 | 192-C9 | 38 | GCUGUA AAAGUAACAUGUCAA-UGAAAGGUAAC UACAGC | < |
| 65/151 | 192-E10 | 38 | GCUGUA AAAGUAACAAGUCAA-UGAAAGGUAAC UACAGC | < |
| 66/152 | 192-C10 | 38 | GCUGUG AAAGUAACAAGUCAA-UGAAAGGUAAC CACAGC | = |
| 67/153 | 192-D11 | 38 | GCAGUG AAAGUAACAUGUCAA-UGAAAGGUAAC CACAGC | < |
| 68/154 | 192-G11 | 38 | GCUGUG AAAGUAACAUGUCAA-UGAAAGGUAAC CACUGC | < |
| 69/155 | 192-H11 | 38 | GCUAUG AAAGUAACAUGUCAA-UGAAAGGUAAC CAUAGC | < |
| 70/156 | 192-D10 | 38 | GCUGCG AAAGCGACAUGUCAA-UGAAAGGUAGC CGCAGC | << |
| 71/157 | 192-E9 | 38 | GCUGUG AAAGCAACAUGUCAA-UGAAAGGUAGC CACAGC | << |
| 72/158 | 192-H9 | 38 | GCUGUG AAAGUAACAUGUCAA-UGAAAGGUAGC CGCAGC | << |
| 73/159 | 191-A6 | 39 | AGCGUG AAAGUAACACGUAAAAUGAAAGGUAAC CACGCU | < | terminal nucleotides that may hybridize to each other (bold)

nucleotides which may mainly comprise a SDF-binding motif nt.:= nucleotides

Comp.:= Clones were tested as aptamers in a competition binding assay vs. 192-A10-001; =:= equal binding affinity as 192-A10-001; <:= weaker binding affinity than 192-A1-001; <<:= much weaker binding affinity than 192-A10-001

Fig. 1

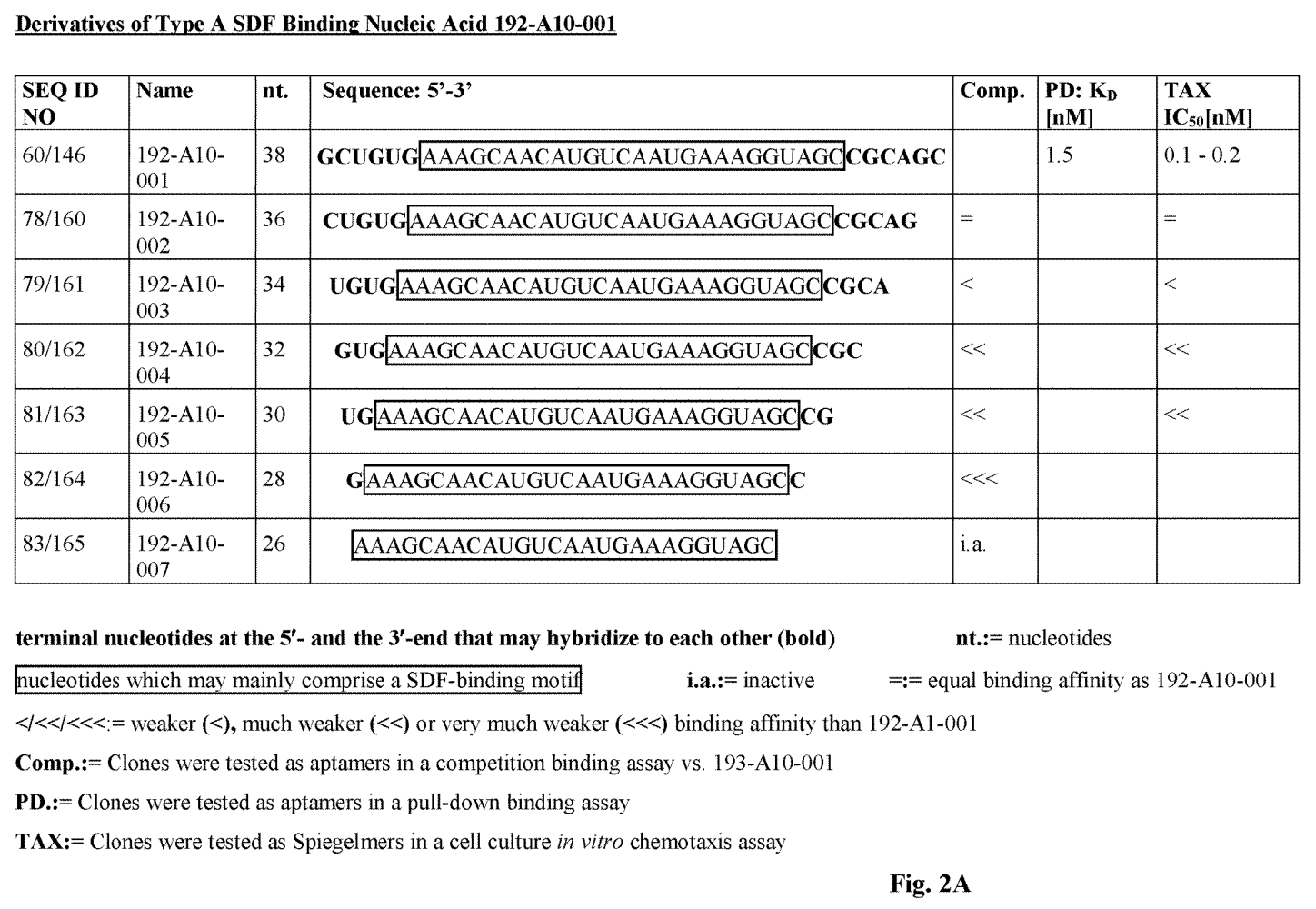

Derivatives of Type A SDF Binding Nucleic Acid 192-A10-001

| SEQ ID NO | Name | nt. | Sequence: 5'-

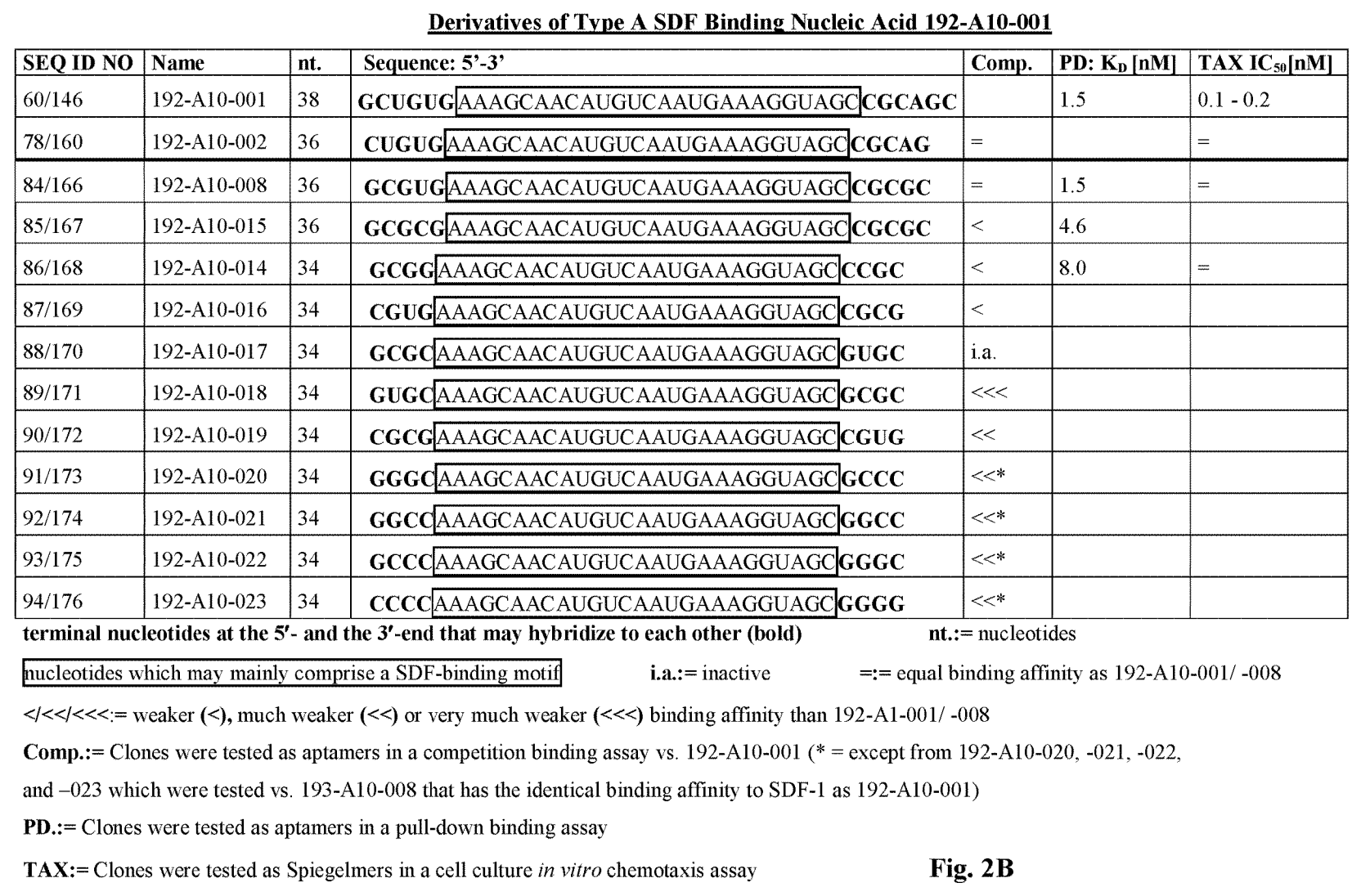

Derivatives of Type A SDF Binding Nucleic Acid 192-A10-001

Type B SDF-1 binding nucleic acids

| SEQ ID NO | Name | nt. | Sequence: 5'-3' | C. |
|---|---|---|---|---|
| 5/29 | 193-C2-001 | 47 | AGCGUGGUGUGAUCUAGAUGUAGUGGCUGAUCCUAGUCAGGUACGCU | + |
| 6/30 | 193-G2-001 | 47 | AGCGUGGUGUGAUCUAGAUGUAUUGGCUGAUCCUAGUCAGGUACGCU | + |
| 7/31 | 193-F2-001 | 47 | AGCGUGGUGUGAUCUAGAUGUAAUGGCUGAUCCUAGUCAGGUGCGCU | + |
| 8/32 | 193-G1-002 | 45 | GCGAGGUGUGAUCUAGAUGUAGUGGCUGAUCCUAGUCAGGUGCGC | << |
| 9/33 | 193-D2-002 | 45 | GCGUGGUGUGAUCUAGAUGUAGUGGCUGAUCCUAGUCAGGUGCGC | < |
| 10/34 | 193-A1-002 | 45 | GCAUGGUGUGAUCUAGAUGUAGUGGCUGAUCCUAGUCAGGUGCCC | <<< |
| 11/35 | 193-D3-002 | 45 | GCGUGGUGUGAUCUAGAUGUAAUGGCUGAUCCUAGUCAGGGACGC | < |
| 12/36 | 193-B3-002 | 45 | GCGUGGUGUGAUCUAGAUGUAGAGGCUGAUCCUAGUCAGGUACGC | << |
| 13/37 | 193-H3-002 | 45 | GCGUGGUGUGAUCUAGAUGUAAAGGCUGAUCCUAGUCAGGUACGC | < |
| 14/38 | 193-E3-002 | 45 | GCGUGGUGUGAUCUAGAUGUAGUGGCUGUUCCUAGUCAGGUAUGC | << |
| 15/39 | 193-D1-002 | 45 | GCGUGGUGUGAUCUAGAUGUAGUGGCUGAUCCUAGUUAGGUACGC | <<< | terminal nucleotides that may hybridize to each other (bold)

nucleotides which may mainly comprise a SDF-binding motif    nt.:= nucleotides

C.:= Clones C2, G2, and F2 were tested as aptamers in a competition binding assay vs. 192-A10-001; all other clones were tested as aptamers in a competition binding assay vs. 193-G2-012 that has the identical binding affinity to SDF-1 as 193-G2-001 (see Fig. 4B)

+:= better binding affinity than 192-A10-001

</<</<<<:= weaker (<), much weaker (<<) or very much weaker (<<<) binding affinity than 193-G2-001/ -012

Fig. 3

Derivatives of Type B SDF Binding Nucleic Acids 193-C2/G2-001

| SEQ ID NO | Name | nt. | Sequence: 5'-3' | Comp. | PD K_D [nM] | Biacore K_D [nM] |
|---|---|---|---|---|---|---|
| 5/29 | 193-G2-001 | 47 | AGCGUG GUGUGAUCUAGAUGUAGUGGCUGAUCCUAGUCAG GUACGCU | | 0.3 | 0.5 |
| 6/30 | 193-C2-001 | 47 | AGCGUG GUGUGAUCUAGAUGUAGUGGCUGAUCCUAGUCAG GUACGCU | = | | 0.6 |
| 16/40 | 193-C2-002 | 45 | GCGUG GUGUGAUCUAGAUGUAGUGGCUGAUCCUAGUCAGG UACGC | = | | 0.8 |
| 17/41 | 193-C2-003 | 43 | CGUG GUGUGAUCUAGAUGUAGUGGCUGAUCCUAGUCAGG U ACG | < | | |
| 18/42 | 193-C2-004 | 41 | GUG GUGUGAUCUAGAUGUAGUGGCUGAUCCUAGUCAGG UA C | << | | |
| 19/43 | 193-C2-005 | 39 | UG GUGUGAUCUAGAUGUAGUGGCUGAUCCUAGUCAGG UA | <<< | | |
| 20/44 | 193-C2-006 | 37 | G GUGUGAUCUAGAUGUAGUGGCUGAUCCUAGUCAGG U | <<< | | |
| 21/45 | 193-C2-007 | 35 | GUGUGAUCUAGAUGUAGUGGCUGAUCCUAGUCAGG | i.a. | | | terminal nucleotides at the 5'- and the 3'-end that may hybridize to each other (bold)  nt.:= nucleotides nucleotides which may mainly comprise a SDF-binding motif    i.a.:= inactive    =:= equal binding affinity as 193-G2-001

</</<<</<<<:= weaker (<), much weaker (<<) or very much weaker (<<<) binding affinity than 193-G2-001

Comp.:= Clones were tested as aptamers in a competition binding assay vs. 193-G2-001

PD.:= Clones were tested as aptamers in a pull-down binding assay

Fig. 4A

Derivatives of Type B SDF Binding Nucleic Acid 193-C2/G2-001

| SEQ ID NO | Name | nt. | Sequence: 5'-3' | Comp. | PD K$_D$ [nM] | Biacore K$_D$ [nM] |
|---|---|---|---|---|---|---|
| 6/30 | 193-G2-001 | 47 | AGCGUG\|GUGUGAUCUAGAUGUAUUGGCUGAUCCUAGUCAGG\|UAC GCU | | 0.3 | 0.5 |
| 22/46 | 193-G2-012 | 45 | GCGUG\|GUGUGAUCUAGAUGUAUUGGCUGAUCCUAGUCAGG\|UAC GC | = | 0.3 | |
| 23/47 | 193-G2-013 | 45 | GCGCG\|GUGUGAUCUAGAUGUAUUGGCUGAUCCUAGUCAGG\|CGC GC | << | 5.3 | |
| 24/48 | 193-G2-014 | 43 | GCGC\|GUGUGAUCUAGAUGUAUUGGCUGAUCCUAGUCAGG\|GCGC | << | 4.7 | |
| 25/49 | 193-G2-015 | 43 | GGGC\|GUGUGAUCUAGAUGUAUUGGCUGAUCCUAGUCAGG\|GCCC | <<* | 4.5 | |
| 26/50 | 193-G2-016 | 43 | GGCC\|GUGUGAUCUAGAUGUAUUGGCUGAUCCUAGUCAGG\|GGCC | <<* | 4.2 | |
| 27/51 | 193-G2-017 | 43 | GCCC\|GUGUGAUCUAGAUGUAUUGGCUGAUCCUAGUCAGG\|GGGC | <<* | 4.2 | | terminal nucleotides at the 5'- and the 3'-end that may hybridize to each other (bold)   nt.:= nucleotides nucleotides which may mainly comprise a SDF-binding motif   =:= equal binding affinity as 193-G2-001/ -012

</ << / <<< := weaker (<), much weaker (<<) or very much weaker (<<<) binding affinity than 193-G2-001 and 193-G2-012, respectively Comp.:= Clones were tested as aptamers in a competition binding assay vs. 193-G2-001 (* = except from 193-G2-015, -016, -017 which were tested in a competition binding assay vs. 193-G2-012 that has the identical binding affinity to SDF-1 as 193-G2-001)

PD.:= Clones were tested as aptamers in a pull-down binding assay

Fig. 4B

Type C SDF-1 binding nucleic acids

| SEQ ID NO | Name | nt. | Sequence: 5'-3' | Comp. |
|---|---|---|---|---|
| 95/177 | 197-B2 | 39 | GUGCUGCGGG GGUUAGGGCUAGAAGUCGG CCUGCAGCAC | < |
| 96/178 | 191-D5-001 | 39 | AGCGUGGCGA GGUUAGGGCUAGAAGUCGG UCGACACGCU | < |
| 97/179 | 197-H1 | 39 | GUGUUGCGGA GGUUAGGGCUAGAAGUCGG UCAGCAGCAC | < |
| 98/180 | 190-D3 | 48 | CGUGCGGCCUAAGAGA GGUUAGGGCUUAAAGUCGG UCUUUGGCCAACACG | << |
| 99/181 | 190-A3-001 | 48 | CGUGCGCUUGAGAUAGG GGUUAGGGCUUAAAGUCGG CUGAUUCUCACG | < |
| 99/181 | 190-A3-001 * | 48 | CGUGCGCUUGAGAUAGG GGUUAGGGCUUAAAGUCGG CUGAUUCUCACG | < |
| 100/182 | 190-A2 | 48 | CGUGAUUGGUGAGG GGUUAGGGCUUGAAGUCGG CCUUGUCCAGUCACG | << |
| 101/183 | 191-A5 | 39 | AGCGUGAAGG GGUUAGGGCUCGAAGUCGG CUGACACGCU | << |
| 102/184 | 197-H3 | 39 | GUGCUGCGGG GGUUAGGGCUCGAAGUCGG CCCGCAGCAC | < |
| 103/185 | 197-B1 | 39 | GUGUUCCCGG GGUUAGGGCUUGAAGUCGG CCCGCAGCAC | << |
| 104/186 | 197-E3 | 39 | GUGUUGCAGG GGUUAGGGCUUGAAGUCGG CCUGCAGCAC | < |
| 105/187 | 197-H2 | 39 | GUGCUGCGGG GGUUAGGGCUCAAAGUCGG CCUGCAGCAC | << |
| 106/188 | 197-D1 | 38 | GUGCUGCCGG GGUUAGGGCUAA-AGUCGG CCGACAGCAC | << |
| 107/189 | 197-D2 | 39 | GUGCUGUGGG GGUCAGGGCUAGAAGUCGG CCUGCAGCAC | << | terminal nucleotides that may hybridize to each other (bold)
nucleotides which may mainly comprise a SDF-binding motif nt.:= nucleotides    Comp.:= Clones were tested as aptamers in a competition binding assay vs. 192-A10-001
=:= equal binding affinity as 192-A10;  <:= weaker binding affinity than 192-A10  <<:= much weaker binding affinity than 192-A10
*:= alternative hybridization

Fig. 5

Derivatives of Type C SDF Binding Nucleic Acid 190-A3-001

| SEQ ID NO | Name | nt. | Sequence: 5'-3' | Comp. |
|---|---|---|---|---|
| 99/181 | 190-A3-001 | 48 | CGUGCGCUUGAGAUAGGGGUUAGGGCUUAAAGUCGGCUGAUUCUCACG | |
| 99/181 | 190-A3-001* | 48 | CGUGCGCUUGAGAUAGGGGUUAGGGCUUAAAGUCGGCUGAUUCUCACG | |
| | | | | |
| 112/190 | 190-A3-003 | 38 | UGAGAUAGGGGUUAGGGCUUAAAGUCGGCUGAUUCUCA | = |
| 113/191 | 190-A3-004 | 36 | GAGAUAGGGGUUAGGGCUUAAAGUCGGCUGAUUCUC | = |
| 114/192 | 190-A3-007 | 29 | GGGGUUAGGGCUUAAAGUCGGCUGAUUCU | <<< | terminal nucleotides at the 5′- and the 3′-end that may hybridize to each other (bold) nt.:= nucleotides nucleotides which may mainly comprise a SDF-binding motif (boxed) =:= equal binding affinity as 190-A3-001

</<</<<<:= weaker (<), much weaker (<<) or very much weaker (<<<) binding affinity than 190-A3-001

Comp.:= Clones were tested as aptamers in a competition binding assay vs. 190-A3-001

*:= alternative hybridization of the terminal nucleotides

Fig. 6

Derivatives of Type C SDF Binding Nucleic Acid 191-D5-001

| SEQ ID NO | Name | nt. | Sequence: 5'-3' | Comp. vs. 191-D5-001 | Comp. vs. 191-D5-007 | Biacore $K_D$ [nM] |
|---|---|---|---|---|---|---|
| 96/178 | 191-D5-001 | 39 | AGCGUGGGCGAGGUUAGGGCUAGAAGUCGGUCGACACGCU | | < | 0.73 |
| 115/193 | 191-D5-002 | 37 | GCGUGGGCGAGGUUAGGGCUAGAAGUCGGUCGACACGC | = | | |
| 116/194 | 191-D5-003 | 35 | CGUGGGCGAGGUUAGGGCUAGAAGUCGGUCGACACG | = | | |
| 117/195 | 191-D5-004 | 33 | CG-GGGCGAGGUUAGGGCUAGAAGUCGGUCGAC-CG | < | | |
| 118/196 | 191-D5-005 | 33 | CG-GGCGAGGUUAGGGCUAGAAGUCGGUCGCC-CG | = | | |
| 119/197 | 191-D5-006 | 31 | CG--GCGAGGUUAGGGCUAGAAGUCGGUCGC--CG | = | | |
| 120/198 | 191-D5-007 | 29 | CG---G-GAGGUUAGGGCUAGAAGUCGGUC-C--CG | + | | 0.75 |
| 121/199 | 191-D5-010 | 27 | G----G-GAGGUUAGGGCUAGAAGUCGGUC-C--C | | < | | terminal nucleotides at the 5'- and the 3'-end that may hybridize to each other (bold)    nt.:= nucleotides nucleotides which may mainly comprise a SDF-binding motif    =:= equal binding affinity as 191-D5-001/-007

</</<<<:= weaker (<), much weaker (<<) or very much weaker (<<<) binding affinity than 191-D5-001/-007

Comp.:= Clones were tested as aptamers in a competition binding assay vs. 191-D5-001 or 191-D5-007 whereas both clones have the identical binding affinity to SDF-1 as 191-D5-001

Fig. 7A

Derivatives of Type C SDF Binding Nucleic Acid 191-D5-001

| SEQ ID NO | Name | nt. | Sequence: 5'-3' | Comp. vs. 191-D5-007 |
|---|---|---|---|---|
| 120/198 | 191-D5-007 | 29 | CG---G-GA\|GUUAGGGCUAGAAGUCGG\|UC-C---CG | |
| 121/199 | 191-D5-010 | 27 | G---G-GA\|GGUUAGGGCUAGAAGUCGG\|UC-C---C | < |
| 122/200 | 191-D5-017 | 27 | CCGC\|GGUUAGGGCUAGAAGUCGG\|GCGG | < |
| 123/201 | 191-D5-029 | 27 | CCCG\|GGUUAGGGCUAGAAGUCGG\|CGGG | < |
| 124/202 | 191-D5-024 | 27 | GGCG\|GGUUAGGGCUAGAAGUCGG\|CGCC | < |
| 125/203 | 191-D5-017-29a | 29 | CCCGC\|GGUUAGGGCUAGAAGUCGG\|GCGGG | < |
| 126/204 | 191-D5-017-29b | 29 | GCCGC\|GGUUAGGGCUAGAAGUCGG\|GCGGC | < |
| 127/205 | 191-D5-019-29a | 29 | CCCCG\|GGUUAGGGCUAGAAGUCGG\|CGGGG | < |
| 128/206 | 191-D5-024-29a | 29 | CGGCG\|GGUUAGGGCUAGAAGUCGG\|CGCCG | = |
| 129/207 | 191-D5-024-29b | 29 | GGGCG\|GGUUAGGGCUAGAAGUCGG\|CGCCC | = | terminal nucleotides at the 5'- and the 3'-end that may hybridize to each other (bold)   nt.:= nucleotides nucleotides which may mainly comprise a SDF-binding motif =:= equal binding affinity as 191-D5-007

</</<<<:= weaker (<), much weaker (<<) or very much weaker (<<<) binding affinity than 191-D5-007

Comp.:= Clones were tested as aptamers in a competition binding assay vs. 191-D5-007

Fig. 7B

Derivatives of Type C SDF Binding Nucleic Acid 197-B2

| SEQ ID NO | Name | nt. | Sequence: 5'-3' | Comp.vs. 197-B2 | Comp. vs. 191-D5-007 | TAX IC$_{50}$[nM] |
|---|---|---|---|---|---|---|
| 95/177 | 197-B2 | 39 | GUGCUGCGGG GGUUAGGGCUAGAAGUCGG CCUGCAGCAC | | = | 0.1-0.2 |
| 130/208 | 197-B2-001 | 37 | UGCUGCGGG GGUUAGGGCUAGAAGUCGG CCUGCAGCA | = | | |
| 131/209 | 197-B2-002 | 35 | GCUGCGGG GGUUAGGGCUAGAAGUCGG CCUGCAGC | = | | |
| 132/210 | 197-B2-003 | 33 | CUGCGGG GGUUAGGGCUAGAAGUCGG CCUGCAG | = | | |
| 133/211 | 197-B2-004 | 31 | UGCGGG GGUUAGGGCUAGAAGUCGG CCUGCA | = | | |
| 134/212 | 197-B2-005 | 29 | GCGGG GGUUAGGGCUAGAAGUCGG CCUGC | = | | |
| 135/213 | 197-B2-006 | 29 | GCCGG GGUUAGGGCUAGAAGUCGG CCGGC | | = | 0.1-0.2 |
| 136/214 | 197-B2-006-31a | 31 | GGCCGG GGUUAGGGCUAGAAGUCGG CCGGCC | | = | |
| 137/215 | 197-B2-006-31b | 31 | CGCCGG GGUUAGGGCUAGAAGUCGG CCGGCG | | = | | terminal nucleotides at the 5'- and the 3'-end that may hybridize to each other (bold)    nt.:= nucleotides nucleotides which may mainly comprise a SDF-binding motif    i.a.:= inactive =:= equal binding affinity as 197-B2 or 191-D5-007

</</<<:= weaker (<), much weaker (<<) or very much weaker (<<<) binding affinity than as 197-B2 or 191-D5-007

Comp.:= Clones were tested as aptamers in a competition binding assay vs. 197-B2 or 191-D5-007 whereas both clones have the identical binding affinity to SDF-1

TAX:= Clones were tested as Spiegelmers in a cell culture *in vitro* chemotaxis assay

Fig. 8

Other SDF-1 Binding Nucleic Acids (Type D SDF-1 Binding Nucleic Acids)

| SEQ ID NO | Name | nt. | Sequence: 5'-3' | PD $K_D$ [nM] |
|---|---|---|---|---|
| 142/216 | 194-A2-001 | 48 | CGUGGUCCGUUGUGUGUCAGGUCUAUUCGCCCGGUUGCAGGGCAUCCGCG | 12.0 |
| 143/217 | 196-B12-003 | 49 | GCAGUGUGACGCGGACGUGAUAGGACACAGAGCUGAUCCCGCUCAGGUGAG | 7.6 |
| 144/218 | 196-B12-004 | 49 | CAACAGCAGUGUGACGCGGACGUGAUAGGACAGAGCUGAUCCCGCUCAG | 5.3 | terminal nucleotides at the 5'- and the 3'-end that may hybridize to each other (bold)     nt.:= nucleotides

PD.:= Clones were tested as aptamers in a pull-down binding assay

Fig. 9

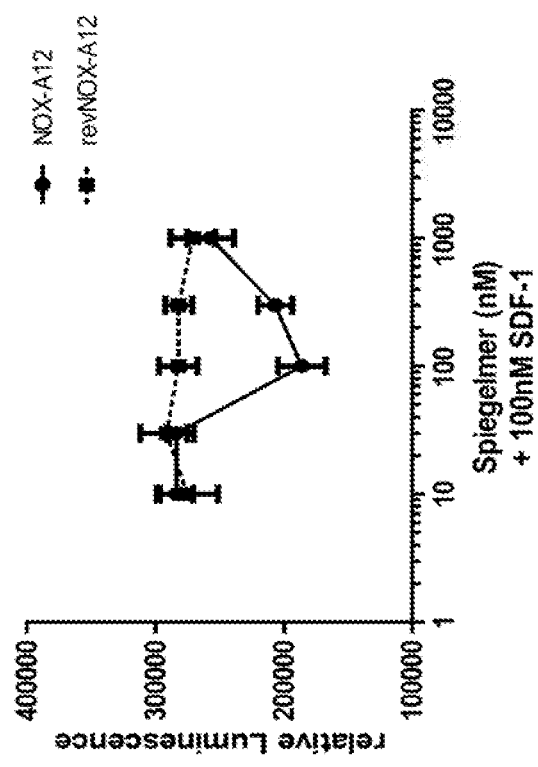
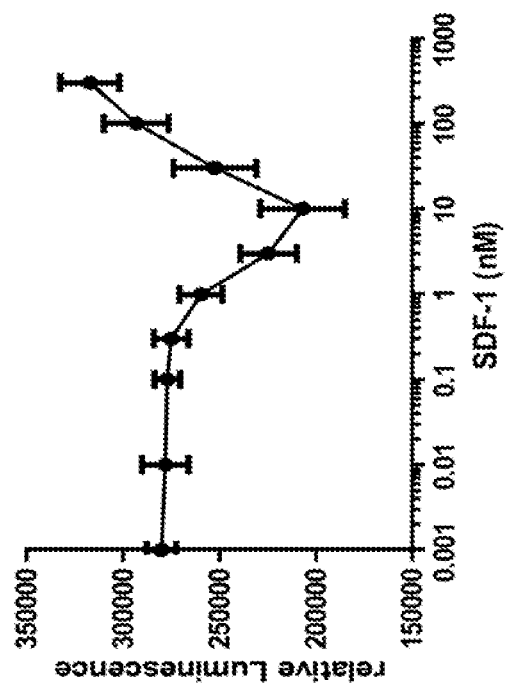
Figure 18B
Figure 18A

SDF-1 BINDING NUCLEIC ACIDS AND THE USE THEREOF IN CANCER TREATMENT

The present invention is related to nucleic acid molecules binding to the CXC chemokine stromal cell-derived factor-1 (SDF-1), methods for the treatment of cancer, and their use in the manufacture of a medicament.

Stromal-cell derived factor-1 (abbr.: SDF-1; synonyms, CXCL12; PBSF [pre-B-cell growth-stimulating factor]; TPAR-1 [TPA repressed gene 1]; SCYB12; TLSF [thymic lymphoma cell stimulating factor]; hIRH [human intercrine reduced in hepatomas]) is an angiogenic CXC chemokine that does not contain the ELR motif typical of the IL-8-like chemokines (Salcedo, Wasserman et al. 1999; Salcedo and Oppenheim 2003) but binds and activates the G-protein coupled receptor CXCR4. As a result of alternative splicing, there are two forms of SDF-1, SDF-1α (68 amino acids, SEQ ID NO: 1) and SDF-1β (SEQ ID NO: 2), which, compared to SDF-1α carries five additional amino acids at the C-terminus (Shirozu, Nakano et al. 1995).

The amino acid sequence conservation between SDF-1 from different species is remarkable: human SDF-1α (SEQ. ID. 1) and murine SDF-1α (SEQ ID NO: 3) are virtually identical. There is only a single conservative change of V to 1 at position 18 (Shirozu, Nakano et al. 1995).

Since the SDF-1 receptor CXCR4 is widely expressed on leukocytes, mature dendritic cells, endothelial cells, brain cells, and megakaryocytes, the activities of SDF-1 are pleiotropic. This chemokine, more than any other identified thus far, exhibits the widest range of biological functions. The most significant functional effects of SDF-1 are:

- Homing and attachment of epithelial cells to neovascular sites in the choroid portion of the retina;
- SDF-1 is required to maintain stem cells and progenitor cells, e.g. hematopoietic progenitor (usually CD34+) cells in the bone marrow of the adult;
- SDF-1 supports proliferation of pre-B cells and augments the growth of bone marrow B cell progenitors and it induces specific migration of pre- and pro-B cells, while not acting as a significant chemoattractant for mature B cells;
- SDF-1 is one of the most efficacious T cell chemoattractants; and
- SDF-1 and its receptor CXCR4 are essential for embryonic development.

Altered expression levels of SDF-1 or its receptor CXCR4 or altered responses towards those molecules are said to be associated with many human diseases, such as retinopathy (Brooks, Caballero et al. 2004; Butler, Guthrie et al. 2005; Meleth, Agron et al. 2005); cancer of breast (Muller, Homey et al. 2001; Cabioglu, Sahin et al. 2005), ovaries (Scotton, Wilson at al. 2002), pancreas (Koshiba, Hosotani et al. 2000), thyroid (Hwang, Chung et al. 2003) andnasopharynx (Wang, Wu et al. 2005); glioma (Zhou, Larsen et al. 2002); neuroblastoma (Geminder, Sagi-Assif et al. 2001); B cell chronic lymphocytic leukemia (Burger, Tsukada et al. 2000); WHIM syndrome (WHIM is an abbreviation for Warts, Hypogammaglobulinemia, Infections, Myelokathexis syndrome) (Gulino, Moratto et al. 2004; Balabanian, Lagane et al. 2005b; Kawai, Choi et al. 2005); immunologic deficiency syndromes (Arya, Ginsberg et al. 1999; Marechal, Arenzana-Seisdedos et al. 1999; Soriano, Martinez et al. 2002); pathologic neovascularization (Salvucci, Yao et al. 2002; Yamaguchi, Kusano et al. 2003; Grunewald, Avraham et al. 2006); inflammation (Murdoch 2000; Fedyk, Jones et al. 2001; Wang, Guan et al. 2001); multiple sclerosis (Krumbholz, Theil et al. 2006); rheumatoid arthritis/osteoarthritis (Buckley, Amft et al. 2000; Kanbe, Takagishi et al. 2002; Grassi, Cristino et al. 2004).

Tumors (including solid and hematological neoplasias and malignancies) are not just masses of cancer cells: infiltration of tumors with immune-cells is a characteristic of cancer. Many human cancers have a complex chemokine network that influences the extent and phenotype of this infiltrate, as well as tumor growth, survival, migration, and angiogenesis. Most solid tumors contain many non-malignant stromal cells. Indeed, stromal cells sometimes outnumber cancer cells. The predominant stromal cells that are found in cancers are macrophages, lymphocytes, endothelial cells and fibroblasts.

Cells from different cancer types have different profiles of chemokine-receptor expression, but the SDF-1 receptor CXCR4 is most commonly found in tumor cells of mouse and man: tumor cells from at least 23 different types of human cancers of epithelial, mesenchymal, and haematopoietic origin express CXCR4 (Balkwill 2004) with SDF-1 being the only known ligand for CXCR4. Apart from the bone marrow and secondary lymphoid tissue, where it is constitutively expressed, SDF-1 is found in primary tumor sites in lymphoma (Corcione, Ottonello et al. 2000) and brain tumors of both neuronal and astrocytic lineage. Furthermore, it is present at high levels in ovarian (Scotton, Wilson et al. 2002) and pancreatic cancer (Koshiba, Hosotani et al. 2000) as well as at sites of metastasis in breast (Muller, Homey et al. 2001) and thyroid cancer (Hwang. Chung et al. 2003), neuroblastoma and haematological malignancies (Geminder, Sagi-Assif et al. 2001).

Besides CXCR4 another SDF-1 receptor was identified: RDC1/CXCR7 (Balabanian, Lagane et al. 2005a, Burns, Summers et al. 2006). In vitro and in vivo studies with prostate cancer cell lines suggest that alterations in CXCR7/RDC1 expression are associated with enhanced adhesive and invasive activities in addition to a survival advantage. In vitro and in vivo studies have shown that both receptors for SDF-1, namely CXCR4 and the CXCR7 promote tumor growth, metastatic potential and resistance to (chemotherapy induced) apoptosis in a number of tumors, e.g. breast cancer, glioblastomas, ovarian cancer, neuroblastoma, lung cancer colorectal and prostate cancer (Burns et al, 2006; Li et al, 2008; Scotton et at, 2002; Yang et al, 2008; Zagzag et al, 2008).

CXCR4 and CXCR7 expression thus seems to be a general characteristic of several tumours.

The problem underlying the present invention is to provide a means which specifically interacts with SDF-1, whereby the means are suitable for the prevention and/or treatment of and/or cancer.

Another problem underlying the present invention is to provide a means which supports the therapy of cancer, whereby such therapy of cancer typically makes use of chemotherapy and/or radiation.

A further problem underlying the present invention is to provide a means which is suitable for use an adjunct therapy in the treatment of cancer.

A still further problem underlying the present invention is to provide a means which is capable of chemosensitizing patient suffering cancer and/or chemosensitizing cells forming or being part of a cancer.

These and other problems underlying the present invention are solved by the subject matter of the attached independent claims. Preferred embodiments may be taken from the dependent claims.

More specifically, the problem underlying the present invention is solved in a first aspect which is also the first embodiment of the first aspect, by a nucleic acid molecule capable of binding to SDF-1, preferably capable of inhibiting SDF-1, whereby the nucleic acid molecule is for use in a method for the treatment and/or prevention of a disease or disorder, for use in a method for the treatment of a subject suffering from a disease or disorder or being at risk of developing a disease or disorder as an adjunct therapy, or for use as a medicament for the treatment and/or prevention of a disease or disorder, whereby the disease or disorder is cancer.

In a second embodiment of the first aspect which is also an embodiment of the first embodiment of the first aspect, the cancer is a cancer selected from the group of hematological cancer, whereby preferably the hematological cancer is selected from the group comprising leukemia and myeloma.

In a third embodiment of the first aspect which is also an embodiment of the second embodiment of the first aspect, leukemia is selected from the group comprising chronic lymphoid leukemia and acute myeloid leukemia.

In a fourth embodiment of the first aspect which is also an embodiment of the second embodiment of the first aspect, myeloma is multiple myeloma.

In a fifth embodiment of the first aspect which is also an embodiment of the first embodiment of the first aspect, the cancer is a cancer selected from the group of solid tumors, whereby preferably the solid tumors are selected from the group comprising glioblastoma, colorectal cancer, breast cancer, lymphoma, prostate cancer, pancreatic cancer, renal cancer, ovarian cancer and lung cancer.

In a sixth embodiment of the first aspect which is also an embodiment of the first, the second, the third, the fourth and the fifth embodiment of the first aspect, the adjunct therapy sensitizes the subject, wherein the sensitized subject is more responsive to a therapy for the treatment and/or prevention of the disease or disorder.

In a seventh embodiment of the first aspect which is also an embodiment of the sixth embodiment of the first aspect, the therapy for the treatment and/or prevention of the diseases or disorder comprises the administration of a further pharmaceutically active agent and/or irradiating the subject and/or surgery and/or cellular therapy.

In an eighth embodiment of the first aspect which is also an embodiment of the seventh embodiment of the first aspect, the further pharmaceutically active agent is selected from the group comprising of an antibody, an alkylating agent, an anti-metabolite, a plant alkaloid, a plant terpenoid, a topoisomerase inhibitor, Leucovorin, Methotrexate, Tamoxifen, Sorafenib, Lenalidomide, Bortezomib, Dexamethasone, Flurouracil, and Prednisone.

In a ninth embodiment of the first aspect which is also an embodiment of the eighth embodiment of the first aspect, the antibody is selected from the group comprising Rituximab, Ofatunumab, Cetuximab, Ibritumomab-Tiuxetan, Tositumomab, Trastuzumab, Bevacizumab, and Alemtuzumab.

In a tenth embodiment of the first aspect which is also an embodiment of the eighth embodiment of the first aspect, the alkylating agent is selected from the group comprising cisplatin, carboplatin, oxaliplatin, mechlorethamine, cyclophosphamide, chlorambucil, doxorubicin, lioposomal doxorubicin, bendamustine, temozolomide and Melphalan.

In an eleventh embodiment of the first aspect which is also an embodiment of the eighth embodiment of the first aspect, the anti-metabolite is selected from the group comprising purineazathioprine, mercaptopurine, fludarabine, pentostatin, and cladribine.

In a twelfth embodiment of the first aspect which is also an embodiment of the eighth embodiment of the first aspect, the plant terpenoid is selected from the group comprising a taxane more preferably selected from the group comprising Docetaxel, Paclitaxel, podophyllotoxin and epothilone.

In a thirteenth embodiment of the first aspect which is also an embodiment of the eighth embodiment of the first aspect, the topoisomerase inhibitor is selected from the group comprising camptothecin, irinotecan, and mitoxantrone.

In a fourteenth embodiment of the first aspect which is also an embodiment of the first, the second, the third, the fourth, the fifth, the sixth, the seventh, the eighth, the ninth, the tenth, the eleventh, the twelfth and the thirteenth embodiment of the first aspect, the nucleic acid molecule is capable of blocking the interaction between SDF-1 and an SDF-1 receptor, whereby the SDF-1 receptor is selected from the group comprising CXCR4 and CXCR7.

In a fifteenth embodiment of the first aspect which is also an embodiment of the first, the second, the third, the fourth, the fifth, the sixth, the seventh, the eighth, the ninth, the tenth, the eleventh, the twelfth, the thirteenth and the fourteenth embodiment of the first aspect, the treatment or prevention of the disease or disorder is caused by the nucleic acid molecule inhibiting the interaction between SDF-1 and an SDF-1 receptor.

In a sixteenth embodiment of the first aspect which is also an embodiment of the first, the second, the third, the fourth, the fifth, the sixth, the seventh, the eighth, the ninth, the tenth, the eleventh, the twelfth, the thirteenth, the fourteenth and the fifteenth embodiment of the first aspect, the nucleic acid molecule is selected from the group comprising an SDF-1 binding nucleic acid molecule of type B, an SDF-1 binding nucleic acid molecule of type C, an SDF-1 binding nucleic acid molecule of type A and an SDF-1 binding nucleic acid molecule of type D.

In a seventeenth embodiment of the first aspect which is also an embodiment of the sixteenth embodiment of the first aspect, the SDF-1 binding nucleic acid molecule of type B comprises a central stretch of nucleotides, whereby the central stretch of nucleotides comprises the following nucleotide sequence:

(SEQ ID NO: 52)
5' GUGUGAUCUAGAUGUADWGGCUGWUCCUAGUYAGG 3'.

In an eighteenth embodiment of the first aspect which is also an embodiment of the seventeenth embodiment of the first aspect, the central stretch of nucleotides comprises the following nucleotide sequence:

(SEQ ID NO: 53)
5' GUGUGAUCUAGAUGUADUGGCUGAUCCUAGUCAGG 3'.

In a nineteenth embodiment of the first aspect which is also an embodiment of the seventeenth and the eighteenth embodiment of the first aspect, the SDF-1 binding nucleic acid molecule of type B comprises in 5'→3' direction a first terminal stretch of nucleotides, the central stretch of nucleotides, and a second terminal stretch of nucleotides.

In a twentieth embodiment of the first aspect which is also an embodiment of the seventeenth and the eighteenth embodiment of the first aspect, the SDF-1 binding nucleic acid molecule of type B comprises in 5'→3' direction a second terminal stretch of nucleotides, the central stretch of nucleotides, and a first terminal stretch of nucleotides.

In a twenty-first embodiment of the first aspect which is also an embodiment of the nineteenth and the twentieth embodiment of the first aspect, the first terminal stretch of nucleotides comprises a nucleotide sequence of 5' $X_1X_2$SVNS 3' and the second terminal stretch of nucleotides comprises a nucleotide sequence of 5' BVBSX$_3$X$_4$ 3', whereby $X_1$ is either absent or is A, $X_2$ is G, $X_3$ is C and $X_4$ is either absent or is U;
or
$X_1$ is absent, $X_2$ is either absent or is G, $X_3$ is either absent or is C and $X_4$ is absent.

In a twenty-second embodiment of the first aspect which is also an embodiment of the nineteenth, the twentieth and the twenty-first, preferably the twenty-first, embodiment of the first aspect, the first terminal stretch of nucleotides comprises a nucleotide sequence of 5' $X_1X_2$CRWG 3' and the second terminal stretch of nucleotides comprises a nucleotide sequence of 5' KRYSX$_3$X$_4$ 3',
whereby $X_c$ is either absent or A, $X_2$ is G, $X_3$ is C and $X_4$ is either absent or U.

In a twenty-third embodiment of the first aspect which is also an embodiment of the nineteenth, the twentieth, the twenty-first and the twenty-second, preferably the twenty-first or the twenty-second embodiment of the first aspect, the first terminal stretch of nucleotides comprises a nucleotide sequence of 5' $X_1X_2$CGUG 3' and the second terminal stretch of nucleotides comprises a nucleotide sequence of 5' UACGX$_3$X$_4$ 3',
whereby $X_1$ is either absent or A, $X_2$ is G, $X_3$ is C, and $X_4$ is either absent or U,
preferably the first terminal stretch of nucleotides comprises a nucleotide sequence of 5' AGCGUG 3' and the second terminal stretch of nucleotides comprises a nucleotide sequence of 5' UACGCU 3'.

In a twenty-fourth embodiment of the first aspect which is also an embodiment of the nineteenth, the twentieth and the twenty-first, preferably the twenty-first embodiment of the first aspect, the first terminal stretch of nucleotides comprises a nucleotide sequence of 5' $X_1X_2$SSBS 3' and the second terminal stretch of nucleotides comprises a nucleotide sequence of 5' BVSSX$_3$X$_4$ 3',
whereby $X_1$ is absent, $X_2$ is either absent or G, $X_3$ is either absent or C, and $X_4$ is absent, preferably the first terminal stretch of nucleotides comprises a nucleotide sequence of 5' GCGUG 3' and the second terminal stretch of nucleotides comprises a nucleotide sequence of 5' UACGC 3'.

In a twenty-fifth embodiment of the first aspect which is also an embodiment of the sixteenth, the seventeenth, the eighteenth, the nineteenth, the twentieth, the twenty-first, the twenty-second, the twenty-third and the twenty-fourth embodiment of the first aspect, the SDF-1 binding nucleic acid molecule of type B comprises a nucleotide sequence according to any one of SEQ ID NO: 5 to SEQ ID NO: 20 and SEQ ID NO: 22 to SEQ ID NO: 28,
preferably any one of SEQ ID NO: 5 to SEQ ID NO: 7, SEQ ID NO: 16, SEQ ID NO: 22 and SEQ ID NO: 28,
more preferably any one of SEQ ID NO: 22 and SEQ ID NO: 28.

In a twenty-sixth embodiment of the first aspect which is also an embodiment of the sixteenth embodiment of the first aspect, the SDF-1 binding nucleic acid molecule of type C comprises a central stretch of nucleotides, whereby the central stretch of nucleotides comprises a nucleotide sequence of GGUYAGGCUHRX$_4$AGUCGG (SEQ ID NO: 108),
whereby $X_4$ is either absent or is A.

In a twenty-seventh embodiment of the first aspect which is also an embodiment of the twenty-sixth embodiment of the first aspect, the central stretch of nucleotides comprises a nucleotide sequence of 5' GGUYAGGGCUHRAAGU-CGG 3' (SEQ ID NO: 109), 5' GGUYAGGGCUHRAGU-CGG 3' (SEQ ID NO: 110) or 5' GGUUAGGGCUHGAA-GUCGG 3' (SEQ ID NO: 111), preferably 5' GGUUAGGGCUHGAAGUCGG 3' (SEQ ID NO: 111).

In a twenty-eighth embodiment of the first aspect which is also an embodiment of the twenty-sixth and the twenty-seventh embodiment of the first aspect, the SDF-1 binding nucleic acid molecule of type C comprises in 5'→3' direction a first terminal stretch of nucleotides, the central stretch of nucleotides, and a second terminal stretch of nucleotides.

In a twenty-ninth embodiment of the first aspect which is also an embodiment of the twenty-sixth and the twenty-seventh embodiment of the first aspect, the SDF-1 binding nucleic acid molecule of type C comprises in 5'→3' direction a second terminal stretch of nucleotides, the central stretch of nucleotides, and a first terminal stretch of nucleotides.

In a thirtieth embodiment of the first aspect which is also an embodiment of the twenty-eighth and the twenty-ninth embodiment of the first aspect, the first terminal stretch of nucleotides comprises a nucleotide sequence of 5' RKS-BUSNVGR 3' (SEQ ID NO: 138) and the second stretch of nucleotides comprises a nucleotide sequence of 5' YYN-RCASSMY 3' (SEQ ID NO: 139),
preferably the first terminal stretch of nucleotides comprises a nucleotide sequence of 5' RKSBUGSVGR 3' (SEQ ID NO: 140) and the second terminal stretch of nucleotides comprises a nucleotide sequence of 5' YCNRCASSMY 3' (SEQ ID NO: 141).

In a thirty-first embodiment of the first aspect which is also an embodiment of the twenty-eighth and the twenty-ninth embodiment of the first aspect, the first terminal stretch of nucleotides comprises a nucleotide sequence of 5' $X_S$SSSV 3' and the second terminal stretch of nucleotides comprises a nucleotide sequence of 5' BSSSX$_S$ 3', whereby $X_S$ is either absent or is S,
preferably the first terminal stretch of nucleotides comprises a nucleotide sequence of 5' SGGSR 3' and the second terminal stretch of nucleotides comprises a nucleotide sequence of 5' YSCCS 3'.

In a thirty-second embodiment of the first aspect which is also an embodiment of the twenty-eighth and the twenty-ninth embodiment of the first aspect,
a) the first terminal stretch of nucleotides comprises a nucleotide sequence of 5' GCCGG 3' and the second terminal stretch of nucleotides comprises a nucleotide sequence of 5' CCGGC 3'; or
b) the first terminal stretch of nucleotides comprises a nucleotide sequence of 5' CGUGCGCUUGA-GAUAGG 3' (SEQ ID NO: 220) and the second terminal stretch of nucleotides comprises a nucleotide sequence of 5' CUGAUUCUCACG 3' (SEQ ID NO: 221); or
c) the first terminal stretch of nucleotides comprises a nucleotide sequence of 5' UGAGAUAGG 3' and the second terminal stretch of nucleotides comprises a nucleotide sequence of 5' CUGAUUCUCA 3' (SEQ ID NO: 222); or
d) the first terminal stretch of nucleotides comprises a nucleotide sequence of 5' GAGAUAGG 3' and the second terminal stretch of nucleotides comprises a nucleotide sequence of 5' CUGAUUCUC 3'.

In a thirty-third embodiment of the first aspect which is also an embodiment of the twenty-sixth, the twenty-seventh, the twenty-eighth, the twenty-ninth, the thirtieth, the thirty-first and the thirty-second embodiment of the first aspect, the type C SDF-1 binding nucleic acid molecule comprises a nucleotide sequence according to any one of SEQ ID NO: 95 to SEQ ID NO: 107, SEQ ID NO: 112 to SEQ ID NO: 137, SEQ ID NO: 223 and SEQ ID NO: 224,
preferably any one of SEQ ID NO: 120, SEQ ID NO: 128, SEQ ID NO: 129, SEQ ID NO:134, SEQ ID NO: 135, SEQ ID NO: 223 and SEQ ID NO: 224.

In a thirty-fourth embodiment of the first aspect which is also an embodiment of the sixteenth embodiment of the first aspect, the SDF-1 binding nucleic acid molecule of type A comprises a central stretch of nucleotides, whereby the central stretch of nucleotides comprises a nucleotide sequence of 5' AAAGYRACAHGUMAAX$_4$ UGAAAGGUARC 3' (SEQ ID NO: 74),
whereby X$_4$ is either absent or is A.

In a thirty-fifth embodiment of the first aspect which is also an embodiment of the thirty-fourth embodiment of the first aspect, the central stretch of nucleotides comprises a nucleotide sequence of
5'AAAGYRACAHGUMAAUGAAAGGUARC 3' (SEQ ID NO: 75), or
5' AAAGYRACAHGUMAAAUGAAAGGUARC 3' (SEQ ID NO: 76), or
5' AAAGYAACAHGUCAAUGAAAGGUARC 3'(SEQ ID NO: 77), preferably the central stretch of nucleotides comprises a nucleotide sequence of 5' AAAGYAACAHGUCAAUGAAAGGUARC 3' (SEQ ID NO: 77).

In a thirty-sixth embodiment of the first aspect which is also an embodiment of the thirty-fourth and thirty-fifth embodiment of the first aspect, the SDF-1 binding nucleic acid molecule of type A comprises in 5'→3' direction a first terminal stretch of nucleotides, the central stretch of nucleotides, and a second terminal stretch of nucleotides.

In a thirty-seventh embodiment of the first aspect which is also an embodiment of the thirty-fourth and the thirty-fifth embodiment of the first aspect, the SDF-1 binding nucleic acid molecule of type A comprises in 5'→3' direction a second terminal stretch of nucleotides, the central stretch of nucleotides, and a first terminal stretch of nucleotides.

In a thirty-eighth embodiment of the first aspect which is also an embodiment of the thirty-sixth and the thirty-seventh embodiment of the first aspect, the first terminal stretch of nucleotides comprises a nucleotide sequence of 5' X$_1$X$_2$NNBV 3' and the second terminal stretch of nucleotides comprises a nucleotide sequence of 5' BNBNX$_3$X$_4$ 3' whereby X$_1$ is either absent or R, X$_2$ is S, X$_3$ is S and X$_4$ is either absent or Y;
or
X$_1$ is absent, X$_2$ is either absent or S, X$_3$ is either absent or S and X$_4$ is absent.

In a thirty-ninth embodiment of the first aspect which is also an embodiment of the thirty-sixth, the thirty-seventh and the thirty-eighth, preferably the thirty-eighth embodiment of the first aspect, the first terminal stretch of nucleotides comprises a nucleotide sequence of 5' RSHRYR 3' and the second terminal stretch of nucleotides comprises a nucleotide sequence of 5' YRYDSY 3',
preferably the first terminal stretch of nucleotides comprises a nucleotide sequence of 5' GCUGUG 3' and the second terminal stretch of nucleotides comprises a nucleotide sequence of 5' CGCAGC 3'.

In a fortieth embodiment of the first aspect which is also an embodiment of the thirty-sixth, the thirty-seventh and the thirty-eighth, preferably the thirty-eighth embodiment of the first aspect, the first terminal stretch of nucleotides comprises a nucleotide sequence of 5' X$_2$BBBS 3' and the second terminal stretch of nucleotides comprises a nucleotide sequence of 5' SBBVX$_3$ 3',
whereby X$_2$ is either absent or is S and X$_3$ is either absent or is S;
preferably the first terminal stretch of nucleotides comprises a nucleotide sequence of 5' CUGUG 3' and the second terminal stretch of nucleotides comprises a nucleotide sequence of 5' CGCAG 3';
or the first terminal stretch of nucleotides comprises a nucleotide sequence of 5' GCGUG 3' and the second terminal stretch of nucleotides comprises a nucleotide sequence of 5' CGCGC 3'.

In a forty-first embodiment of the first aspect which is also an embodiment of the thirty-fourth, the thirty-fifth, the thirty-sixth, the thirty-seventh, the thirty-eighth, the thirty-ninth and the fortieth embodiment of the first aspect, the SDF-1 binding nucleic acid molecule of type A comprises a nucleotide sequence according to any one of SEQ ID NO: 60 to SEQ ID NO: 73, SEQ ID NO: 78 to SEQ ID NO: 82, SEQ ID NO: 84 to SEQ ID NO: 87, SEQ ID NO: 89 to SEQ ID NO: 94, and SEQ ID NO: 145,
preferably any one of SEQ ID NO: 60, SEQ ID NO: 63, SEQ ID NO: 66, SEQ ID NO: 78, SEQ ID NO: 84, and SEQ ID NO: 146,
more preferably any one of SEQ ID NO: 84 and SEQ ID NO: 146.

In a forty-second embodiment of the first aspect which is also an embodiment of the sixteenth embodiment of the first aspect, the SDF-1 binding nucleic acid molecule of type D comprises a nucleotide sequence according to any one of SEQ ID NO: 142 to SEQ ID NO: 144.

In a forty-third embodiment of the first aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first, the thirty-second, the thirty-third, the thirty-fourth, the thirty-fifth, the thirty-sixth, the thirty-seventh, the thirty-eighth, the thirty-ninth, the fortieth, the forty-first and the forty-second embodiment of the first aspect, the SDF-1 is human SDF-1, whereby preferably the human SDF-1 is human SDF-1 alpha or human SDF-1 beta, more preferably the human SDF-1 is human SDF-1 alpha.

In a forty-fourth embodiment of the first aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first, the thirty-second, the thirty-third, the thirty-fourth, the thirty-fifth, the thirty-sixth, the thirty-seventh, the thirty-eighth, the thirty-ninth, the fortieth, the forty-first, the forty-second and the forty-third embodiment of the first aspect, the nucleic acid molecule comprises a modification, whereby the modification is preferably a high molecular weight moiety and/or whereby the modification preferably allows to modify the characteristics of the nucleic acid molecule in terms of residence time in the animal or human body, preferably the human body.

In a forty-fifth embodiment of the first aspect which is also an embodiment of the forty-fourth embodiment of the first aspect, the modification is selected from the group comprising a HES moiety, a PEG moiety, biodegradable modifications and combinations thereof.

In a forty-sixth embodiment of the first aspect which is also an embodiment of the forty-fifth embodiment of the first aspect, the modification is a PEG moiety consisting of a straight or branched PEG, whereby preferably the molecular weight of the straight or branched PEG is from about 20,000 to 120,000 Da, more preferably from about 30,000 to 80,000 Da and most preferably about 40,000 Da.

In a forty-seventh embodiment of the first aspect which is also an embodiment of the forty-fifth embodiment of the first aspect, the modification is a HES moiety, whereby preferably the molecular weight of the HIES moiety is from about 10,000 to 200,000 Da, more preferably from about 30,000 to 170.000 Da and most preferably about 150,000 Da.

In a forty-eighth embodiment of the first aspect which is also an embodiment of the forty-fourth, the forty-fifth, the forty-sixth and the forty-seventh embodiment of the first aspect, the modification is attached to the nucleic acid molecule via a linker, wherein preferably the linker is a biostable or biodegradable linker.

In a forty-ninth embodiment of the first aspect which is also an embodiment of the forty-fourth, the forty-fifth, the forty-sixth, the forty-seventh and the forty-eighth embodiment of the first aspect, the modification is attached to the nucleic acid molecule at the 5'-terminal nucleotide of the nucleic acid molecule and/or the 3'-terminal nucleotide of the nucleic acid molecule and/or to a nucleotide of the nucleic acid molecule between the 5'-terminal nucleotide of the nucleic acid molecule and the 3'-terminal nucleotide of the nucleic acid molecule In a fiftieth embodiment of the first aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first, the thirty-second, the thirty-third, the thirty-fourth, the thirty-fifth, the thirty-sixth, the thirty-seventh, the thirty-eighth, the thirty-ninth, the fortieth, the forty-first, the forty-second, the forty-third, the forty-fourth, the forty-fifth, the forty-sixth, the forty-seventh, the forty-eighth and the forty-ninth embodiment of the first aspect, the nucleotides of the nucleic acid molecule or the nucleotides forming the nucleic acid molecule are L-nucleotides.

In a fifty-first embodiment of the first aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first, the thirty-second, the thirty-third, the thirty-fourth, the thirty-fifth, the thirty-sixth, the thirty-seventh, the thirty-eighth, the thirty-ninth, the fortieth, the forty-first, the forty-second, the forty-third, the forty-fourth, the forty-fifth, the forty-sixth, the forty-seventh, the forty-eighth, the forty-ninth and the fiftieth embodiment of the first aspect, the nucleic acid molecule is an L-nucleic acid molecule.

The problem underlying the present invention is solved in a second aspect which is also the first embodiment of the second aspect, by a pharmaceutical composition comprising as a first pharmaceutically active agent the nucleic acid molecule according to any one of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first, the thirty-second, the thirty-third, the thirty-fourth, the thirty-fifth, the thirty-sixth, the thirty-seventh, the thirty-eighth, the thirty-ninth, the fortieth, the forty-first, the forty-second, the forty-third, the forty-fourth, the forty-fifth, the forty-sixth, the forty-seventh, the forty-eighth, the forty-ninth, the fiftieth and the fifty-first embodiment of the first aspect and optionally a further constituent, whereby the further constituent is selected from the group comprising a pharmaceutically acceptable excipient, a pharmaceutically acceptable carrier and a further pharmaceutically active agent, and whereby the pharmaceutical composition is for use in a method for the treatment and/or prevention of a disease or disorder, or for use in a method for the treatment of a subject suffering from a disease or disorder or being at risk of developing a disease or a disorder as an adjunct therapy, or for the treatment and/or prevention of a disease or disorder, whereby the disease or disorder is cancer.

In a second embodiment of the second aspect which is also an embodiment of the first embodiment of the second aspect, the adjunct therapy sensitizes the subject, wherein the sensitized subject is more responsive to a therapy for the treatment and/or prevention of the disease or disorder.

In a third embodiment of the second aspect which is also an embodiment of the second embodiment of the second aspect, the therapy for the treatment and/or prevention of the diseases or disorder comprises the administration of a further pharmaceutically active agent and/or irradiating the subject and/or surgery and/or cellular therapy.

In a fourth embodiment of the second aspect which is also an embodiment of the first, the second and the third embodiment of the second aspect, the further pharmaceutically active agent is a pharmaceutically active agent selected from the group comprising an antibody, an alkylating agent, an anti-metabolite, a plant alkaloid, preferably vincristine, a plant terpenoid, a topoisomerase inhibitor, Leucovorin, Methotrexate, Tamoxifen, Sorafenib, Lenalidomide, Bortezomib, Dexamethasone, Flurouracil, and Prednisone.

In a fifth embodiment of the second aspect which is also an embodiment of the fourth embodiment of the second aspect, the antibody is selected from the group comprising Rituximab, Ofatumumab, Cetuximab, Ibritumomab-Tiuxetan, Tositumxomab, Trastuzumab, Bevacizumab, and Alemtuzumab.

In a sixth embodiment of the second aspect which is also an embodiment of the fourth embodiment of the second aspect, the alkylating agent is selected from the group comprising cisplatin, carboplatin, oxaliplatin, mechlorethamine, cyclophosphamide, chlorambucil, doxorubicin, lioposomal doxorubicin, bendamustine, temozolomide and Melphalan.

In a seventh embodiment of the second aspect which is also an embodiment of the fourth embodiment of the second aspect, the anti-metabolite is selected from the group comprising purineazathioprine, mercaptopurine, fludarabine, pentostatin, and cladribine.

In an eighth embodiment of the second aspect which is also an embodiment of the fourth embodiment of the second aspect, the plant terpenoid is selected from the group comprising a taxane more preferably selected from the group comprising Docetaxel, Paclitaxel, podophyllotoxin and epothilone.

In a ninth embodiment of the second aspect which is also an embodiment of the fourth embodiment of the second aspect, the topoisomerase inhibitor is selected from the group comprising camptothecin, irinotecan, and mitoxantrone.

In a tenth embodiment of the second aspect which is also an embodiment of the first, the second, the third, the fourth, the fifth, the sixth, the seventh, the eighth and the ninth embodiment of the second aspect, the cancer is a cancer selected from the group of hematological cancer, whereby preferably the hematological cancer is selected from the group of leukemia and myeloma.

In an eleventh embodiment of the second aspect which is also an embodiment of the tenth embodiment of the second aspect, leukemia is selected from the group comprising chronic lymphoid leukemia and acute myeloid leukemia.

In a twelfth embodiment of the second aspect which is also an embodiment of the tenth embodiment of the second aspect, myeloma is multiple myeloma.

In a thirteenth embodiment of the second aspect which is also an embodiment of the first, the second, the third, the fourth, the fifth, the sixth, the seventh, the eighth and the ninth embodiment of the second aspect, the cancer is a cancer selected from the group of solid tumors, whereby preferably the solid tumors are selected from the group comprising glioblastoma, colorectal cancer, breast cancer, lymphoma, prostate cancer, pancreatic cancer, renal cancer, ovarian cancer and lung cancer.

The problem underlying the present invention is solved in a third aspect which is also the first embodiment of the third aspect, by a medicament comprising one or several dosage units of at least a first pharmaceutically active agent, wherein the first pharmaceutically active agent is a nucleic acid molecule capable of binding to SDF-1 as defined in any one of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first, the thirty-second, the thirty-third, the thirty-fourth, the thirty-fifth, the thirty-sixth, the thirty-seventh, the thirty-eighth, the thirty-ninth, the fortieth, the forty-first, the forty-second, the forty-third, the forty-fourth, the forty-fifth, the forty-sixth, the forty-seventh, the forty-eighth, the forty-ninth, the fiftieth and the fifty-first embodiment of the first aspect, whereby the medicament is for use in a method for the treatment and/or prevention of a disease or disorder, or for use in a method for the treatment of a subject suffering from a disease or disorder or being at risk of developing a disease or a disorder as an adjunct therapy, or for the treatment and/or prevention of a disease or disorder, whereby the disease or disorder is cancer.

In a second embodiment of the third aspect which is also an embodiment of the first embodiment of the third aspect, the adjunct therapy sensitizes the subject, wherein the sensitized subject is more responsive to a therapy for the treatment and/or prevention of the disease or disorder.

In a third embodiment of the third aspect which is also an embodiment of the second embodiment of the third aspect, the therapy for the treatment and/or prevention of the diseases or disorder comprises the administration of a further pharmaceutically active agent and/or irradiating the subject and/or surgery and/or cellular therapy.

In a fourth embodiment of the third aspect which is also an embodiment of the first, the second and the third, preferably the first embodiment of the third aspect, the medicament comprises a further pharmaceutically active agent, preferably one or several dosage units of a further pharmaceutically active agent, whereby the further pharmaceutically active agent is selected from the group comprising an antibody, an alkylating agent, an anti-metabolite, a plant alkaloid, preferably vincristine, a plant terpenoid, a topoisomerase inhibitor, Leucovorin, Methotrexate, Tamoxifen, Sorafenib, Lenalidomide, Bortezomib, Dexamethasone and Flurouracil.

In a fifth embodiment of the third aspect which is also an embodiment of the third embodiment of the third aspect, the medicament comprises the further pharmaceutically active agent, preferably one or several dosage units of the further pharmaceutically active agent, whereby the further pharmaceutically active agent is selected from the group comprising an antibody, an alkylating agent, an anti-metabolite, a plant alkaloid, preferably vincristine, a plant terpenoid, a topoisomerase inhibitor, Leucovorin, Methotrexate, Tamoxifen, Sorafenib, Lenalidomide, Bortezomib, Dexamethasone Flurouracil, and Prednisone.

In a sixth embodiment of the third aspect which is also an embodiment of the fourth and the fifth embodiment of the third aspect, the antibody is selected from the group comprising Rituximab, Ofatumumab, Cetuximab, Ibritumomab-Tiuxetan, Tositumomab, Trastuzumab, Bevacizumab, and Alemtuzumab.

In a seventh embodiment of the third aspect which is also an embodiment of the fourth and the fifth embodiment of the third aspect, the alkylating agent is selected from the group comprising cisplatin, carboplatin, oxaliplatin, mechlorethamine, cyclophosphamide, chlorambucil, doxorubicin, lioposomal doxorubicin, bendamustine, temozolomide and Melphalan.

In an eighth embodiment of the third aspect which is also an embodiment of the fourth and the fifth embodiment of the third aspect, the anti-metabolite is selected from the group comprising purineazathioprine, mercaptopurine fludarabine, pentostatin, and cladribine.

In a ninth embodiment of the third aspect which is also an embodiment of the fourth and the fifth embodiment of the third aspect, the plant terpenoid is selected from the group of a taxane, more preferably selected from the group comprising Docetaxel, Paclitaxel, podophyllotoxin and epothilone.

In a tenth embodiment of the third aspect which is also an embodiment of the fourth and the fifth embodiment of the third aspect, the topoisomerase inhibitor is selected from the group comprising camptothecin, irinotecan and mitoxantrone.

In an eleventh embodiment of the third aspect which is also an embodiment of the first, the second, the third, the fourth, the fifth, the sixth, the seventh, the eighth, the ninth and the tenth embodiment of the third aspect, wherein the cancer is a cancer selected from the group of hematological cancer, whereby preferably the hematological cancer is selected from the group comprising leukemia and myeloma.

In a twelfth embodiment of the third aspect which is also an embodiment of the eleventh embodiment of the third aspect, leukemia is selected from the group comprising chronic lymphoid leukemia and acute myeloid leukemia.

In a thirteenth embodiment of the third aspect which is also an embodiment of the eleventh embodiment of the third aspect, myeloma is multiple myeloma.

In a fourteenth embodiment of the third aspect which is also an embodiment of the first, the second, the third, the fourth, the fifth, the sixth, the seventh, the eighth, the ninth and the tenth embodiment of the third aspect, the cancer is a cancer selected from the group of solid tumors, whereby preferably the solid tumors are selected from the group comprising glioblastoma, colorectal cancer, breast cancer, lymphoma, prostate cancer, pancreatic cancer, renal cancer, ovarian cancer and lung cancer.

The problem underlying the present invention is solved in a fourth aspect which is also the first embodiment of the fourth aspect, by use of a nucleic acid molecule as defined in any one of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third, the twenty-fourth, the twenty-fifth, the twenty-sixth, the twenty-seventh, the twenty-eighth, the twenty-ninth, the thirtieth, the thirty-first, the thirty-second, the thirty-third, the thirty-fourth, the thirty-fifth, the thirty-sixth, the thirty-seventh, the thirty-eighth, the thirty-ninth, the fortieth, the forty-first, the forty-second, the forty-third, the forty-fourth, the forty-fifth, the forty-sixth, the forty-seventh, the forty-eighth, the forty-ninth, the fiftieth and the fifty-first embodiment of the first aspect, for the manufacture of a medicament for the treatment and/or prevention of a disease or disorder or for use in a method for the treatment of a subject suffering from a disease or disorder or being at risk of developing a disease or a disorder as an adjunct therapy, whereby the disease or disorder is cancer.

In a second embodiment of the fourth aspect which is also an embodiment of the first embodiment of the fourth aspect, the adjunct therapy sensitizes the subject, wherein the sensitized subject is more responsive to a therapy for the treatment and/or prevention of the disease or disorder.

In a third embodiment of the fourth aspect which is also an embodiment of the second embodiment of the fourth aspect, the therapy for the treatment and/or prevention of the diseases or disorder comprises the administration of a further pharmaceutically active agent and/or irradiating the subject and/or surgery and/or cellular therapy.

In a fourth embodiment of the fourth aspect which is also an embodiment of the first, the second and the third, preferably the first embodiment of the fourth aspect, the medicament is used in combination with a further pharmaceutically active agent, whereby the further pharmaceutically active agent is a pharmaceutically active agent selected from the group comprising an antibody, an alkylating agent, an anti-metabolite, a plant alkaloid, preferably vincristine, a plant terpenoid, a topoisomerase inhibitor, Leucovorin, Methotrexate, Tamoxifen, Sorafenib, Lenalidomide, Bortezomib. Dexamethasone, Flurouracil, and Prednisone.

In a fifth embodiment of the fourth aspect which is also an embodiment of the third embodiment of the fourth aspect, the further pharmaceutically active agent is a pharmaceutically active agent selected from the group comprising an antibody, an alkylating agent, an anti-metabolite, a plant alkaloid, preferably vincristine, a plant terpenoid, a topoisomerase inhibitor, Leucovorin, Methotrexate, Tamoxifen, Sorafenib, Lenalidomide, Bortezomib, Dexamethasone, Flurouracil, and Prednisone.

In a sixth embodiment of the fourth aspect which is also an embodiment of the fourth and the fifth embodiment of the fourth aspect, the antibody is selected from the group comprising Rituximab, Cetuximab, Ibritumomab-Tiuxetan, Tositumomab, Trastuzumab, Bevacizumab, and Alemtuzumab.

In a seventh embodiment of the fourth aspect which is also an embodiment of the fourth and the fifth embodiment of the fourth aspect, the alkylating agent is selected from the group comprising cisplatin, carboplatin, oxaliplatin, mechlorethamine, cyclophosphamide, chlorambucil, doxorubicin, lioposomal doxorubicin, bendamustine, temozolomide and Melphalan.

In an eighth embodiment of the fourth aspect which is also an embodiment of the fourth and the fifth embodiment of the fourth aspect, the anti-metabolite is selected from the group comprising purineazathioprine, mercaptopurine fludarabine, pentostatin, and cladribine.

In a ninth embodiment of the fourth aspect which is also an embodiment of the fourth and the fifth embodiment of the fourth aspect, the plant terpenoid is selected from the group comprising a taxane, more preferably selected from the group of Docetaxel, Paclitaxel, podophyllotoxin and epothilone.

In a tenth embodiment of the fourth aspect which is also an embodiment of the fourth and the fifth embodiment of the fourth aspect, the topoisomerase inhibitor is selected from the group comprising camptothecin, irinotecan, and mitoxantrone.

In an eleventh embodiment of the fourth aspect which is also an embodiment of the fourth and the fifth embodiment of the fourth aspect, the cancer is a cancer selected from the group of hematological cancer, whereby preferably the hematological cancer is selected from the group comprising leukemia and myeloma.

In a twelfth embodiment of the fourth aspect which is also an embodiment of the eleventh embodiment of the fourth aspect, leukemia is selected from the group comprising chronic lymphoid leukemia and acute myeloid leukemia.

In a thirteenth embodiment of the fourth aspect which is also an embodiment of the eleventh embodiment of the fourth aspect, myeloma is multiple myeloma.

In a fourteenth embodiment of the fourth aspect which is also an embodiment of the first, the second, the third, the fourth, the fifth, the sixth, the seventh, the eighth, the ninth and the tenth embodiment of the fourth aspect, the cancer is a cancer selected from the group of solid tumors, whereby preferably the solid tumors are selected from the group comprising glioblastoma, colorectal cancer, breast cancer, lymphoma, prostate cancer, pancreatic cancer, renal cancer, ovarian cancer and lung cancer.

The problem underlying the present invention is solved in a fifth aspect which is also the first embodiment of the fifth aspect, by a method for the treatment of a subject suffering from or being at risk of developing cancer, whereby the method comprises
    a step a) of administering to the subject a pharmaceutically effective amount of a nucleic acid molecule capable of binding to SDF-1 as defined in any one of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty first, the twenty second, the twenty third, the twenty fourth, the twenty fifth, the twenty-sixth, the twenty seventh, the twenty-eighth, the twenty-ninth, the thirtieth, the thirty-first, the thirty-second, the thirty-third, the thirty-fourth, the thirty-fifth, the thirty-sixth, the thirty-seventh, the thirty-eighth, the thirty-ninth, the fortieth, the forty-first, the forty-second, the forty-third, the forty-fourth, the forty-filth, the forty-sixth, the forty-seventh, the forty-eighth, the forty-ninth, the fiftieth and the fifty-first embodiment of the first aspect.

In a second embodiment of the fifth aspect which is also an embodiment of the first embodiment of the fifth aspect, the method comprises
a step b) of irradiating the subject and/or surgery and/or cellular therapy and/or administering a pharmaceutically effective amount of a further pharmaceutically active agent to the subject, whereby the further pharmaceutically active agent is a pharmaceutically active agent selected from the group comprising an antibody, an alkylating agent, an anti-metabolite, a plant alkaloid, preferably vincristine, a plant terpenoid, a topoisomerase inhibitor, Leucovorin, Methotrexate, Tamoxifen, Sorafenib, Lenalidomide, Bortezomib, Dexamethasone, Flurouracil, and Prednisone.

In a third embodiment of the fifth aspect which is also an embodiment of the second embodiment of the fifth aspect, the pharmaceutically effective amount of a nucleic acid molecule capable of binding to SDF-1 as defined in any one of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty first, the twenty second, the twenty third, the twenty fourth, the twenty fifth, the twenty-sixth, the twenty seventh, the twenty-eighth, the twenty-ninth, the thirtieth, the thirty-first, the thirty-second, the thirty-third, the thirty-fourth, the thirty-fifth, the thirty-sixth, the thirty-seventh, the thirty-eighth, the thirty-ninth, the fortieth, the forty-first, the forty-second, the forty-third, the forty-fourth, the forty-fifth, the forty-sixth, the forty-seventh, the forty-eighth, the forty-ninth, the fiftieth and the fifty-first embodiment of the first aspect is administered as an adjunct therapy or part of an adjunct therapy.

In a fourth embodiment of the fifth aspect which is also an embodiment of the third embodiment of the fifth aspect, the adjunct therapy sensitizes the subject, wherein the sensitized subject is more responsive to a therapy for the treatment and/or prevention of the disease or disorder.

In a fifth embodiment of the fifth aspect which is also an embodiment of the fourth embodiment of the fifth aspect, the therapy for the treatment and/or prevention of the disease or disorder comprises the administration of a further pharmaceutically active agent and/or irradiating the subject and/or surgery and/or cellular therapy as performed in step b).

In a sixth embodiment of the fifth aspect which is also an embodiment of the second, the third, the fourth and the fifth embodiment of the fifth aspect, the antibody is selected from the group comprising Rituximab, Cetuximab, Ibritumomab-Tiuxetan, Tositumomab, Trastuzumab, Bevacizumab, and Alemtuzumab.

In a seventh embodiment of the fifth aspect which is also an embodiment of the second, the third, the fourth and the fifth embodiment of the fifth aspect, the alkylating agent is selected from the group comprising cisplatin, carboplatin, oxaliplatin, mechlorethamine, cyclophosphamide, chlorambucil, doxorubicin, lioposomal doxorubicin, bendamustine, temozolomide and Melphalan.

In an eighth embodiment of the fifth aspect which is also an embodiment of the second, the third, the fourth and the fifth embodiment of the fifth aspect, the anti-metabolite is selected from the group comprising purineazathioprine, mercaptopurine, fludarabine, pentostatin, and cladribine.

In a ninth embodiment of the fifth aspect which is also an embodiment of the second, the third, the fourth and the fifth embodiment of the fifth aspect, the plant terpenoid is selected from the group comprising taxanes, more preferably selected from the group of Docetaxel, Paclitaxel, podophyllotoxin and epothilone.

In a tenth embodiment of the fifth aspect which is also an embodiment of the second, the third, the fourth and the fifth embodiment of the fifth aspect, the topoisomerase inhibitor is selected from the group comprising camptothecin, irinotecan, and mitoxantrone.

In an eleventh embodiment of the fifth aspect which is also an embodiment of the first, the second, the third, the fourth, the fifth, the sixth, the seventh, the eighth, the ninth and the tenth embodiment of the fifth aspect, the cancer is a cancer selected from the group of hematological cancer, whereby preferably the hematological cancer is selected from the group comprising leukemia and myeloma.

In a twelfth embodiment of the fifth aspect which is also an embodiment of the eleventh embodiment of the fifth aspect, leukemia is selected from the group comprising chronic lymphoid leukemia and acute myeloid leukemia.

In a thirteenth embodiment of the fifth aspect which is also an embodiment of the eleventh and the twelfth embodiment of the fifth aspect, myeloma is multiple myeloma.

In a fourteenth embodiment of the fifth aspect which is also an embodiment of the first, the second, the third, the fourth, the fifth, the sixth, the seventh, the eighth, the ninth and the tenth embodiment of the fifth aspect, the cancer is a cancer selected from the group of solid tumors, whereby preferably the solid tumors are selected from the group comprising glioblastoma, colorectal cancer, breast cancer, lymphoma, prostate cancer, pancreatic cancer, renal cancer, ovarian cancer and lung cancer.

While not wishing to be bound by any theory, the present inventors have found that the nucleic acid molecules according to the present invention inhibit the binding of SDF-1 to its SDF-1 receptors and thus, either directly or indirectly, are used for the treatment of cancer. Furthermore, the instant inventors have found that the nucleic acid molecules according to the present invention are suitable to block the interaction of SDF-1 with the SDF-1 receptors CXCR4 and CXCR7, respectively. Insofar, the SDF-1 binding nucleic acid molecule according to the present invention can also be viewed as antagonists of CXCR4 and CXCR7, respectively.

As to the various diseases, conditions and disorders which may be treated or prevented by using the nucleic acid molecules according to the present invention or compositions, preferably pharmaceutical compositions comprising the same, it has to be acknowledged that such diseases, conditions and disorders are those which are described herein, including and in particular those described and set forth in the introductory part of the instant application. Insofar, the respective passages form an integral part of the present disclosure teaching the suitability of the nucleic acid molecules for the prevention and treatment, respectively, for said diseases, conditions, and disorders.

As used herein the term SDF-1 refers to any SDF-1 including, but not limited to, mammalian SDF-1. Preferably, the mammalian SDF-1 is selected from the group comprising mice, rat, rabbit, hamster, monkey and human SDF-1. More preferably the SDF-1 is human SDF-1 also referred to as SDF-1α (SEQ ID NO: 1) and/or human SDF-1β (SEQ ID NO: 2), most preferably human SDF-1 also referred to as SDF-1α (SEQ ID NO: 1)

SDF-1 acts through two different receptors, the receptors CXCR4 and RDC1/CXCR7 (Balabanian, Lagane et al. 2005a, Burns, Summers et al. 2006) (see the introductory part of the instant application). Elevated expression of CXCR4 and CXCR7 was shown for several cancer types as described herein.

Because SDF-1 acts through two different receptors, a treatment of an SDF-1 related disease or disorder by a compound specific for one out of the two SDF-1 receptors CXCR4 and CXCR7:
 a) should be less effective due to the two different SDF-1 receptors expressed on cells, preferably cancer cells;
 b) is limited to a distinct population of cells, preferably to a distinct population of cancer cells, due to the individual SDF-1 receptors expressed on the cells.

Cancer is a term for malignant neoplasms, a great and heterogeneous group of diseases in which cells display uncontrolled growth, invasion and often metastasizes, wherein the cancer cells spread to other locations in the body, to regional lymph nodes or distant body sites like brain, bone, liver, or other organs. These three malignant properties of cancer differentiate malignant tumors from benign tumors, whereby, as used herein, the term cancer shall also encompass malignant tumors which in turn are also refereed to herein as tumors. Malignant tumors fall into two categories based on their origin: Hematological and solid tumors.

Hematological tumors are cancer types affecting blood, bone marrow, and lymph nodes. Solid tumors are formed by an abnormal growth of body tissue cells other than blood, bone marrow or lymphatic cells.

Preferred forms of cancer are the following ones:
Adrenocortical Carcinoma
AIDS-Related Cancers such as Kaposi Sarcoma and Lymphoma
Anal Cancer
Appendix Cancer
Atypical Teratoid/Rhabdoid Tumor
Basal Cell Carcinoma
Bile Duct Cancer, Extrahepatic
Bladder Cancer
Bone Cancer
Osteosarcoma
Malignant Fibrous Histiocytoma
Brain Stem Glioma
Brain Tumor such as Astrocytomas, Brain and Spinal Cord Tumors, Brain Stem Glioma, Childhood, Central Nervous System Atypical Teratoid/Rhabdoid Tumor, Central Nervous System Embryonal Tumors, Craniopharyngioma, Ependymoblastoma, Ependymoma, Medulloblastoma, Medulloepithelioma, Pineal Parenchymal Tumors of Intermediate Differentiation, Supratentorial Primitive Neuroectodermal Tumors and Pineoblastoma
Breast Cancer
Bronchial Tumors
Carcinoid Tumor
Carcinoma of Unknown Primary
Cancer of Central Nervous System such as Atypical Teratoid/Rhabdoid Tumor and Lymphoma
Cervical Cancer
Childhood Cancers
Chordoma
Chronic Myeloproliferative Disorders
Colon Cancer
Colorectal Cancer
Craniopharyngioma
Cutaneous T-Cell Lymphoma
Embryonal Tumors
Endometrial Cancer
Ependymoblastoma
Ependymoma,
Esophageal Cancer
Esthesioneuroblastoma
Ewing Sarcoma Family of Tumors
Extracranial Germ Cell Tumor
Extragonadal Germ Cell Tumor
Extrahepatic Bile Duct Cancer
Eye Cancer such as Intraocular Melanoma and Retinoblastoma
Fibrous Histiocytoma of Bone
Osteosarcoma
Gallbladder Cancer
Gastric (Stomach) Cancer
Gastrointestinal Carcinoid Tumor
Gastrointestinal Stromal Tumors (GIST)
Germ Cell Tumor (extracranial, extragonadal or ovarian)
Gestational Trophoblastic Tumor
Glioma
Hairy Cell Leukemia
Head and Neck Cancer
Heart Cancer
Hepatocellular (Liver) Cancer
Histiocytosis
Hypopharyngeal Cancer
Intraocular Melanoma
Islet Cell Tumors (Endocrine Pancreas)
Kaposi Sarcoma
Kidney Cancer
Langerhans Cell Histiocytosis
Laryngeal Cancer
Leukemia such Acute Lymphoblastic Leukemia (abbr. ALL), Acute Myeloid Leukemia (abbr. AML), Chronic Lymphocytic Leukemia (abbr. CLL), Chronic Myelogenous Leukemia (abbr. CML) and Hairy Cell Leukemia
Lip and Oral Cavity Cancer
Liver Cancer (Primary)
Lobular Carcinoma In Situ (LCIS)
Lung Cancer
Lymphoma such as AIDS-Related Lymphoma, Burkitt, Mycosis Fungoides and Sézary Syndrome, Hodgkin, Non-Hodgkin and leukemia of Primary Central Nervous System (abbr. CNS)
Macroglobulinemia
Malignant Fibrous Histiocytoma of Bone and Osteosarcoma
Medulloblastoma
Medulloepithelioma
Melanoma
Merkel Cell Carcinoma
Mesothelioma
Metastatic Squamous Neck Cancer with Occult Primary
Midline Tract Carcinoma Involving NUT Gene
Mouth Cancer
Multiple Endocrine Neoplasia Syndromes
Multiple Myeloma
Mycosis Fungoides
Myelodysplastic Syndromes
Myelodysplastic/Myeloproliferative Neoplasms
Myeloproliferative Disorders
Nasal Cavity and Paranasal Sinus Cancer Nasopharyngeal Cancer
Neuroblastoma
Non-Small Cell Lung Cancer
Oral Cancer
Oral Cavity Cancer
Oropharyngeal Cancer
Osteosarcoma and Malignant Fibrous Histiocytoma of Bone
Ovarian Cancer
Pancreatic Cancer
Papillomatosis
Paraganglioma
Paranasal Sinus and Nasal Cavity Cancer
Parathyroid Cancer
Penile Cancer
Pharyngeal Cancer
Pheochromocytoma
Pineal Parenchymal Tumors of Intermediate Differentiation
Pineoblastoma and Supratentorial Primitive Neuroectodermal Tumors
Pituitary Tumor
Plasma Cell Neoplasm/Multiple Myeloma
Pleuropulmonary Blastoma, Childhood
Primary Central Nervous System (abbr CNS) Lymphoma
Prostate Cancer
Rectal Cancer
Renal Cell (Kidney) Cancer
Renal Pelvis and Ureter, Transitional Cell Cancer
Retinoblastoma
Rhabdomyosarcoma
Salivary Gland Cancer
Sarcoma such as Ewing Sarcoma Family of Tumors, Kaposi Sarcoma, Soft Tissue Sarcoma, Uterine Sarcoma
Skin Cancer such Melanoma, Merkel Cell Carcinoma and Nonmelanoma
Small Cell Lung Cancer
Small Intestine Cancer
Soft Tissue Sarcoma
Squamous Cell Carcinoma
Squamous Neck Cancer Stomach (Gastric) Cancer
Supratentorial Primitive Neuroectodermal Tumors
T-Cell Lymphoma
Testicular Cancer
Throat Cancer
Thymoma and Thymic Carcinoma
Thyroid Cancer
Transitional Cell Cancer of the Renal Pelvis and Ureter
Trophoblastic Tumor, Gestational
Ureter and Renal Pelvis, Transitional Cell Cancer
Urethral Cancer
Uterine Cancer, Endometrial
Uterine Sarcoma
Vaginal Cancer
Vulvar Cancer
Waldenström Macroglobulinemia
Wilms Tumor The SDF-1-CXCR4 axis has been shown to play a role in stem cell mobilization including cancer stem cells, vasculogenesis, tumor growth and metastasis. The SDF-1 receptor CXCR4 is expressed in a variety of cancers and hematological malignancies in vivo as is CXCR7 (Maksym, Tarnowski et al., 2009; Wang, Shiosawa ct al., 2008; Miao, Lucker et al., 2007). The growth and invasion signal for tumor cells is SDF-1, in particular if the cells express the receptors for SDF-1 (Batchelor et al., 2007; Zhu et al., 2009; Xu et al., 2009; Kozin et al., 2010).

CXCR4 as well as SDF-1 are induced by hypoxia (Ceradini et al. 2004). Together with VEGF they represent a potent synergistic axis that initiates and maintains angiogenic/vasculogenic pathways (Kryczek et al. 2005). The role in vasculogenesis is supported by evidence that SDF-1 attracts CXCR4 expressing endothelial progenitor cells from the circulation (Sengupta et al. 2005). SDF-1-CXCR4 mediated recruitment of bone marrow derived cells that support vascularization may also be the reason for recurrence of glioblastoma after irradiation therapy (Kioi et al., 2010). As demonstrated by Kioi et al. in an intracranial glioblastoma multiforme (abbr. GBM) mouse xenograft model the treatment of GBM patients with high dosis of radiation is less effective due to irradiation induced recruitment of bone-marrow derived cells (abbr. BMDCs). The blockade of the interaction of SDF-1 and its receptor CXCR4 by the CXCR4 antagonist AMD3100 prevented the influx of BMDCs in the irradiated tumor (Kioi et al., 2010). In 2010 Tseng et al. presented data with an ENU induced glioblastoma rat model, a model that closely mimics human GBM, that besides CXCR4 also CXCR7 is involved in irradiation induced recruitment of BMDCs. In this study the CXCR7 antagonist CCX2206 prevented the influx of BMDCs in the irradiated tumor (Tseng et al., 2010). In accordance thereof and because the nucleic acid molecules according to the present invention are able to block the interation of both SDF-1 and CXCR4 and SDF-1 and CXCR7 the effect on survival after irradiation is expected to be better than shown for the use of one of the CXCR4 and CXCR7 antagonist alone.

In addition, SDF-1 induces VEGF secretion, while VEGF increases CXCR4 expression (Salcedo et al. 1999) and angiogenesis signals. Therefore inhibition of the SDF-1-CXCR4 axis may reduce or prevent tumor growth by inhibition of angiogenesis/vasculogenesis either with monotherapy or particularly in combination with other antivascular agents such as VEGF inhibitors.

Furthermore it is suggested that 'homing' of CXCR4 expressing cancer cells to SDF-1-expressing organs directs metastatic cells preferentially to the liver, bone marrow, lung and lymph nodes (Alsayed et al. 2007; Burger & Peled 2009) and therefore the SDF-1-CXCR4 axis plays a role in metastasis.

Hence, the inhibition of the SDF-1-CXCR4 axis and the SDF-1-CXCR7 axis with only one compound such as the SDF-1 binding nucleic acid molecule according to the present invention should be effective in treating cancer and/or tumors, in particular a wide range of both haematological and solid tumors either as monotherapy or in combination with other treatments such as, but not limited to, drug therapy, cellular therapy, irradiation and surgery. Moreover, in comparison to a compound that binds and inhibits one out of the two SDF-1 receptors CXCR4 and CXCR7, the inhibition of the SDF-1-CXCR4 axis and the SDF-1-CXCR7 axis with only one compound such as the SDF-1 binding nucleic acid molecule according to the present invention should be more effective in treating cancer and/or tumors, in particular a wide range of both haematological and solid tumors either as monotherapy or in combination with other treatments such as but not limited to drug therapy, cellular therapy, irradiation and surgery.

It is within the present invention that drug therapy comprises the treatment and/or prevention of a disease or disorder by a drug, preferably a pharmaceutically active agent, more preferably a pharmaceutically active agent as defined herein.

As preferably used herein, in cell therapy also referred to as cellular therapy, processed tissue from the organs, embryos, or fetuses of animals such as sheep or cows is injected into a subject suffering from or being at risk of developing a disease or disorder, whereby preferably the disease or disorder is cancer and cell therapy a form of cancer treatment.

In theory, non-hematological cancers can be cured if entirely removed by surgery. When the cancer has metastasized to other sites in the body prior to surgery, complete surgical excision is usually impossible. Examples of surgical procedures or surgery for cancer include mastectomy for breast cancer, prostatectomy for prostate cancer, and lung cancer surgery for non-small cell lung cancer. The goal of the surgery can be either the removal of only the tumor, or of the entire organ. Surgery is often combined with other cancer treatments or therapies, such as chemotherapy and radiation. Cancer surgery may be used to achieve one or more goals. Such goals may include, but are not limited to, cancer prevention, diagnosis, staging, primary treatment, debulking and relieving symptoms or side effects.

Radiotherapy (also referred to X-ray therapy or Irradiation) is the use of ionizing radiation to kill cancer cells. Radiotherapy is used in the medical art to treat almost every type of solid tumor. Irradiation is also used to treat leukemia and lymphoma. Radiotherapy injures or destroys cells in the area being treated by damaging their genetic material, making it impossible for these cells to continue to grow and divide. The effects of radiotherapy are localized and confined to the region being treated. Radiation dose to each site depends on a number of factors, including the radiosensitivity of each cancer type and whether there are tissues and organs nearby that may be damaged by radiation. The goal of radiotherapy is to damage as many cancer cells as possible, while limiting harm to nearby healthy tissue.

Additionally, an SDF-1 binding nucleic molecule according to the present invention is preferred if the physiological effect of the SDF-1-CXCR4 axis and/or SDF-1-CXCR7 axis is related to higher plasma levels of SDF-1. For instance, particular therapeutic agents such as paclitaxel and bevacizumab produce an elevation of plasma SDF-1 levels which can have a negative effect on tumor therapy by releasing more bone marrow derived endothelial progenitor cells or by stimulating growth, invasiveness or metastasis (Shaked, Henke et al., 2008; Xu, Duda at al., 2009). In this case the co-application of an SDF-1 binding nucleic acid will ameliorate the effects of elevated plasma SDF-1 levels.

Moreover, the inhibition of the SDF-1-CXCR4 axis and/or SDF-1-CXCR7 axis by an SDF-1 binding nucleic molecule according to the present invention will enhance the anti-tumor effects of other therapeutic agents by disrupting the adhesive stromal interactions with leukemia and other cancer cells that confer survival and drug resistance to these therapies (Jin et al. 2008; Nervi et al. 2009). Such use of SDF-1 binding nucleic molecule is known as a process known as chemosensitization.

The sensitization of tumor cells to chemotherapy or radiotherapy is known as 'chemosensitization' or 'radiosensitization', respectively. Such 'chemosensitization' or 'radiosensitization', preferably by the nucleic acid molecules according to the present invention, sensitizes the subject suffering from a disease or disorder, whereby the sensitized subject is more responsive to a therapy for the treatment and/or prevention of the disease or disorder, whereby preferably the disease or the disorder is cancer. Such treatment used together with a primary treatment, preferably a cancer treatment, is an adjunct therapy according to the present invention and also referred to as adjunctive therapy. The purpose of such adjunct therapy is to assist a primary treatment, preferably a primary cancer treatment.

Hence, the inhibition of the SDF-1-CXCR4 axis and/or SDF-1-CXCR7 axis will be particularly effective in treating a wide range of both haematological and solid tumors either as monotherapy or in combination with other treatments such as but not limited to drug therapy, cellular therapy, irradiation and surgery.

By these means and in view of the outlined involvement of SDF-1 and SDF-1 receptors—such as CXCR4 and CXCR7-, the SDF-1 binding and the interaction between SDF-1 and SDF-1 receptor inhibiting nucleic acid molecules according to the present invention can help to attenuate such diseases, whereby inhibition of SDF-1 by the SDF-1 binding nucleic acid molecules according to the present invention leads to chemosensitization of malignant cells to be treated by chemotherapy, reduction or inhibition of growth and invasiveness, inhibition of angiogenesis/vasculogenesis, inhibition of metastasis and/or inhibition of elevated plasma SDF-1 levels derived from the response of the host to chemotherapy.

Moreover, the present invention is based on the surprising finding that it is possible to generate nucleic acid molecules binding specifically and with high affinity to SDF-1, thereby inhibiting and antagonizing the effects of SDF-1, in particular the effects of SDF-1 on its receptors such as CXCR4 and CXCR7.

An antagonists to SDF-1 is a molecule that binds to SDF-1—such as the SDF-1 binding nucleic acid molecules according to the present invention—and inhibits the function of SDF-1, preferably in an in vitro assay or in an in vivo model as described in the Examples.

It is within the present invention that the nucleic acid according to the present invention is a nucleic acid molecule. Insofar the terms nucleic acid and nucleic acid molecule are used herein in a synonymous manner if not indicated to the contrary. Moreover, such nucleic acids are preferably also referred to herein as the nucleic acid molecules according to the present invention, the nucleic acids according to the present invention, the inventive nucleic acids or the inventive nucleic acid molecules.

The features of the nucleic acid according to the present invention as described herein can be realised in any aspect of the present invention where the nucleic acid is used, either alone or in any combination.

As outlined in more detail herein, the present inventors have identified a number of different SDF-1 binding nucleic acid molecules, whereby the nucleic acid molecules can be characterised in terms of stretches of nucleotides which are also referred to herein as Boxes (see Example 1). As experimentally shown in examples 5 to 11 the inventors could surprisingly demonstrate in several systems that SDF-1 binding nucleic acid molecules are suitable for the treatment of cancer and actually capable of treating cancer.

The different types of SDF-1 binding nucleic acid molecules comprise three different stretches of nucleotides: the first terminal stretch of nucleotides, the central stretch of nucleotides and second terminal stretch of nucleotides. In general, SDF-1 binding nucleic acid molecules of the present invention comprise at their 5'-end and the 3'-end the terminal stretches of nucleotides: the first terminal stretch of nucleotides and the second terminal stretch of nucleotides (also referred to as 5'-terminal stretch of nucleotides and 3'-terminal stretch of nucleotides). The first terminal stretch of nucleotides and the second terminal stretch of nucleotides can, in principle due to their base complementarity, hybridize to each other, whereby upon hybridization a double-stranded structure is formed. However, such hybridization is not necessarily realized in the molecule under physiological and/or non-physiological conditions. The three stretches of nucleotides of SDF-1 binding nucleic acid molecules—the first terminal stretch of nucleotides, the central stretch of nucleotides and second terminal stretch of nucleotides—are arranged to each other in 5'→3'-direction: the first terminal stretch of nucleotides—the central stretch of nucleotides—the second terminal stretch of nucleotides. However, alternatively, the second terminal stretch of nucleotides, the central stretch of nucleotides and the terminal first stretch of nucleotides are arranged to each other in 5'→3'-direction.

The differences in the sequences of the defined boxes or stretches between the different SDF-1 binding nucleic acid molecules influence the binding affinity to SDF-1. Based on binding analysis of the different SDF-1 binding nucleic acid molecules of the present invention the central stretch and the nucleotides forming the same are individually and more preferably in their entirety essential for binding to human SDF-1.

The terms 'stretch' and 'stretch of nucleotide' are used herein in a synonymous manner if not indicated to the contrary.

In a preferred embodiment the nucleic acid according to the present invention is a single nucleic acid molecule. In a further embodiment, the single nucleic acid molecule is present as a multitude of the single nucleic acid molecule or as a multitude of the single nucleic acid molecule species.

It will be acknowledged by the ones skilled in the art that the nucleic acid molecule in accordance with the invention preferably consists of nucleotides which are covalently linked to each other, preferably though phosphodiester links or linkages.

It is within the present invention that the nucleic acids according to the present invention comprise two or more stretches or part(s) thereof can, in principle, hybridise with each other. Upon such hybridisation a double-stranded structure is formed. It will be acknowledged by the ones skilled in the art that such hybridisation may or may not occur, particularly under in vitro and/or in vivo conditions. Also, in case of such hybridisation, it is not necessarily the case that the hybridisation occurs over the entire length of the two stretches where, at least based on the rules for base pairing, such hybridisation and thus formation of a double-stranded structure may, in principle, occur. As preferably used herein, a double-stranded structure is a part of a nucleic acid molecule or a structure formed by two or more separate strands or two spatially separated stretches of a single strand of a nucleic acid molecule, whereby at least one, preferably two or more base pairs exist which are base pairing preferably in accordance with the Watson-Crick base pairing rules. It will also be acknowledged by the one skilled in the art that other base pairing such as Hoogsten base pairing may exist in or form such double-stranded structure. It is also to be acknowledged that the feature that two stretches hybridize preferably indicates that such hybridization is assumed to happen due to base complementarity of the two stretches.

In a preferred embodiment the term arrangement as used herein, means the order or sequence of structural or functional features or elements described herein in connection with the nucleic acids disclosed herein.

It will be acknowledged by the person skilled in the art that the nucleic acids according to the present invention are capable of binding to SDF-1. Without wishing to be bound by any theory, the present inventors assume that the SDF-1 binding results from a combination of three-dimensional structural traits or elements of the claimed nucleic acid molecule, which are caused by orientation and folding patterns of the primary sequence of nucleotides forming such traits or elements, whereby preferably such traits or elements are the first terminal stretch of nucleotides, the central stretch of nucleotides and the second terminal stretch of nucleotides of SDF-1 binding nucleic acid molecules. It is evident that the individual trait or element may be formed by various different individual sequences the degree of variation of which may vary depending on the three-dimensional structure such element or trait has to form. The overall binding characteristic of the claimed nucleic acid results from the interplay of the various elements and traits, respectively, which ultimately results in the interaction of the claimed nucleic acid with its target, i.e. SDF-1. Again without being wished to be bound by any theory, the central stretch of nucleotides that is characteristic for SDF-1 binding nucleic acids seems to be important for mediating the binding of the claimed nucleic acid molecules with SDF-1. Accordingly, the nucleic acids according to the present invention are suitable for the interaction with SDF-1. Also, it will be acknowledged by the person skilled in the art that the nucleic acids according to the present invention are antagonists to SDF-1. Because of this the nucleic acids according to the present invention are suitable for the treatment and prevention, respectively, of any disease or condition which is associated with or caused by SDF-1. Such diseases and conditions may be taken from the prior art which establishes that SDF-1 is involved or associated with said diseases and conditions, respectively, and which is incorporated herein by reference providing the scientific rationale for the therapeutic use of the nucleic acids according to the invention.

The nucleic acids according to the present invention shall also comprise nucleic acids which are essentially homologous to the particular sequences disclosed herein. The term substantially homologous shall be understood such as the homology is at least 75%, preferably 85%, more preferably 90% and most preferably more that 95%, 96%, 97%, 98% or 99%.

The actual percentage of homologous nucleotides present in the nucleic acid according to the present invention will depend on the total number of nucleotides present in the nucleic acid. The percent modification can be based upon the total number of nucleotides present in the nucleic acid.

The homology between two nucleic acid molecules can be determined as known to the person skilled in the art. More specifically, a sequence comparison algorithm may be used for calculating the percent sequence homology for the test sequence(s) relative to the reference sequence, based on the designated program parameters. The test sequence is preferably the sequence or nucleic acid molecule which is said to be homologous or to be tested whether it is homologous, and if so, to what extent, to a different nucleic acid molecule, whereby such different nucleic acid molecule is also referred to as the reference sequence. In an embodiment, the reference sequence is a nucleic acid molecule as described herein, preferably a nucleic acid molecule having a sequence according to any one of SEQ ID NO: 5 to SEQ ID NO: 225, more preferably a nucleic acid molecule having a sequence according to any one of SEQ ID NO: 22, SEQ ID NO: 28, SEQ ID NO: 120, SEQ ID NO: 128, SEQ ID NO: 129, SEQ ID NO: 134, SEQ ID NO: 135, SEQ ID NO: 223, SEQ ID NO: 224, SEQ ID NO: 84, SEQ ID NO: 146, SEQ ID NO: 142, SEQ ID NO: 143, and SEQ ID NO: 144. Optimal alignment of sequences for comparison can be conducted, e.g., by the local homology algorithm of Smith & Waterman (Smith & Waterman, 1981) by the homology alignment algorithm of Needleman & Wunsch (Needleman & Wunsch, 1970) by the search for similarity method of Pearson &

Lipman (Pearson & Lipman, 1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity is the algorithm used in the basic local alignment search tool (hereinafter "BLAST"), see, e.g. Altschul et al (Altschul et al. 1990 and Altschul et al, 1997). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al (McGinnis et al, 2004).

The nucleic acids according to the present invention shall also comprise nucleic acids which have a certain degree of identity relative to the nucleic acids disclosed herein and defined by their nucleotide sequence. More preferably, the instant invention also comprises those nucleic acid molecules which have an identity of at least 75%, preferably 85%, more preferably 90% and most preferably more than 95%, 96%, 97%, 98% or 99% relative to the nucleic acids disclosed herein and defined by their nucleotide sequence or a part thereof.

The term inventive nucleic acid or nucleic acid according to the present invention shall also comprise those nucleic acids comprising the nucleic acids sequences disclosed herein or part thereof, such as, e.g., a metabolite or derivative of the nucleic acid according to the present invention, preferably to the extent that the nucleic acids or said parts are involved in the or capable of binding to SDF-1. Such a nucleic acid may be derived from the ones disclosed herein, e.g., by truncation. Truncation may be related to either or both of the ends of the nucleic acids as disclosed herein. Also, truncation may be related to the inner sequence of nucleotides, i.e. it may be related to the nucleotide(s) between the 5' and the 3' terminal nucleotide, respectively. Moreover, truncation shall comprise the deletion of as little as a single nucleotide from the sequence of the nucleic acids disclosed herein. Truncation may also be related to more than one stretch of the inventive nucleic acid(s), whereby the stretch can be as little as one nucleotide long. The binding of a nucleic acid according to the present invention can be determined by the ones skilled in the art using routine experiments or by using or adopting a method as described herein, preferably as described herein in the example part.

The nucleic acids according to the present invention may be either D-nucleic acids or L-nucleic acids. Preferably, the inventive nucleic acids are L-nucleic acids. In addition it is possible that one or several parts of the nucleic acid are present as D-nucleic acids or at least one or several parts of the nucleic acids are L-nucleic acids. The term "part" of the nucleic acids shall mean as little as one nucleotide. Such nucleic acids are generally referred to herein as D- and L-nucleic acids, respectively. Therefore, in a particularly preferred embodiment, the nucleic acids according to the present invention consist of L-nucleotides and comprise at least one D-nucleotide. Such D-nucleotide is preferably attached to a part different from the stretches defining the nucleic acids according to the present invention, preferably those parts thereof, where an interaction with other parts of the nucleic acid is involved. Preferably, such D-nucleotide is attached at a terminus of any of the stretches and of any nucleic acid according to the present invention, respectively. In a further preferred embodiment, such D-nucleotides may act as a spacer or a linker, preferably attaching modifications such as PEG and HES to the nucleic acids according to the present invention.

It is also within the present invention that each and any of the nucleic acid molecules described herein in their entirety in terms of their nucleic acid sequence(s) are limited to the particular nucleotide sequence(s). In other words, the terms "comprising" or "comprise(s)" shall be interpreted in such embodiment in the meaning of containing or consisting of.

It is also within the present invention that the nucleic acids according to the present invention are part of a longer nucleic acid whereby this longer nucleic acid comprises several parts whereby at least one such part is a nucleic acid, or a part thereof, according to the present invention. The other part(s) of these longer nucleic acids can be either one or several D-nucleic acid(s) or L-nucleic acid(s). Any combination may be used in connection with the present invention. These other part(s) of the longer nucleic acid can exhibit a function which is different from binding, preferably from binding to SDF-1. One possible function is to allow interaction with other molecules, whereby such other molecules preferably are different from SDF-1, such as, e.g., for immobilization, cross-linking, detection or amplification. In a further embodiment of the present invention the nucleic acids according to the invention comprise, as individual or combined moieties, several of the nucleic acids of the present invention. Such nucleic acid comprising several of the nucleic acids of the present invention is also encompassed by the term longer nucleic acid.

L-nucleic acids as used herein are nucleic acids consisting of L-nucleotides, preferably consisting completely of L-nucleotides.

D-nucleic acids as used herein are nucleic acids consisting of D-nucleotides, preferably consisting completely of D-nucleotides.

The terms nucleic acid and nucleic acid molecule are used herein in an interchangeable manner if not explicitly indicated to the contrary.

Also, if not indicated to the contrary, any nucleotide sequence is set forth herein in 5'→3' direction.

As preferably used herein any position of a nucleotide is determined or referred to relative to the 5' end of a sequence, a stretch or a substretch. Accordingly, a second nucleotide is the second nucleotide counted from the 5' end of the sequence, stretch and substretch, respectively. Also, in accordance therewith, a penultimate nucleotide is the second nucleotide counted from the 3' end of a sequence, stretch and substretch, respectively.

Irrespective of whether the inventive nucleic acid consists of D-nucleotides, L-nucleotides or a combination of both with the combination being e.g. a random combination or a defined sequence of stretches consisting of at least one L-nucleotide and at least one D-nucleic acid, the nucleic acid may consist of desoxyribonucleotide(s), ribonucleotide(s) or combinations thereof.

Designing the inventive nucleic acids as L-nucleic acid is advantageous for several reasons. L-nucleic acids are enantiomers of naturally occurring nucleic acids. D-nucleic acids, however, are not very stable in aqueous solutions and particularly in biological systems or biological samples due to the widespread presence of nucleases. Naturally occurring nucleases, particularly nucleases from animal cells are not capable of degrading L-nucleic acids. Because of this the biological half-life of the L-nucleic acid is significantly increased in such a system, including the animal and human body. Due to the lacking degradability of L-nucleic acid no nuclease degradation products are generated and thus no side effects arising therefrom observed. This aspect delimits the L-nucleic acid of factually all other compounds which are used in the therapy of diseases and/or disorders involving the presence of SDF-1. L-nucleic acids which specifically bind to a target molecule through a mechanism different from Watson Crick base pairing, or aptamers which consists partially or completely of L-nucleotides, particularly with those parts of the aptamer being involved in the binding of the aptamer to the target molecule, are also called spiegelmers. Aptamers and spiegelmers as such are known to a person skilled in the art and are, among others, described in 'The Aptamer Handbook' (eds. Klussmann, 2006).

It is also within the present invention that the inventive nucleic acids, regardless whether they are present as D-nucleic acids, L-nucleic acids or D,L-nucleic acids or whether they are DNA or RNA, may be present as single stranded or double stranded nucleic acids. Typically, the inventive nucleic acids are single stranded nucleic acids which exhibit defined secondary structures due to the primary sequence and may thus also form tertiary structures. The inventive nucleic acids, however, may also be double stranded in the meaning that two strands which are complementary or partially complementary to each other are hybridised to each other.

The inventive nucleic acids may be modified. Such modifications may be related to the single nucleotide of the nucleic acid and are well known in the art. Examples for such modification are described by, among others, Venkatesan et al. (Venkatesan, Kim et al. 2003) and Kusser (Kusser 2000). Such modification can be a H atom, a F atom or O—$CH_3$ group or $NH_3$-group at the 2' position of the individual nucleotide of which the nucleic acid consists. Also, the nucleic acid according to the present invention can comprises at least one LNA nucleotide. In an embodiment the nucleic acid according to the present invention consists of LNA nucleotides.

In an embodiment, the nucleic acids according to the present invention may be a multipartite nucleic acid. A multipartite nucleic acid as used herein, is a nucleic acid which consists of at least two separate nucleic acid strands. These at least two nucleic acid strands form a functional unit whereby the functional unit is a ligand to a target molecule. The at least two nucleic acid strands may be derived from any of the inventive nucleic acids by either cleaving the nucleic acid molecule to generate two strands or by synthesising one nucleic acid corresponding to a first part of the inventive, i.e. overall nucleic acid and another nucleic acid corresponding to the second part of the overall nucleic acid. It is to be acknowledged that both the cleavage and the synthesis may be applied to generate a multipartite nucleic acid where there are more than two strands as exemplified above. In other words, the at least two separate nucleic acid strands are typically different from two strands being complementary and hybridising to each other although a certain extent of complementarity between said at least two separate nucleic acid strands may exist and whereby such complementarity may result in the hybridisation of said separate strands.

Finally it is also within the present invention that a fully closed, i.e. circular structure for the nucleic acids according to the present invention is realized, i.e. that the nucleic acids according to the present invention are closed in an embodiment, preferably through a covalent linkage, whereby more preferably such covalent linkage is made between the 5' end and the 3' end of the nucleic acid sequences as disclosed herein or any derivative thereof.

A possibility to determine the binding constants of the nucleic acid molecules according to the present invention is the use of the methods as described in example 3 and 4 which confirms the above finding that the nucleic acids according to the present invention exhibit a favourable $K_D$ value range. An appropriate measure in order to express the intensity of the binding between the individual nucleic acid molecule and the target which is in the present case SDF-1 is the so-called $K_D$ value which as such as well the method for its determination are known to the one skilled in the art.

Preferably, the $K_D$ value shown by the nucleic acids according to the present invention is below 1 µM. A $K_D$ value of about 1 µM is said to be characteristic for a non-specific binding of a nucleic acid to a target. As will be acknowledged by the ones skilled in the art, the $K_D$ value of a group of compounds such as the nucleic acids according to the present invention is within a certain range. The above-mentioned $K_D$ of about 1 µM is a preferred upper limit for the $K_D$ value. The lower limit for the $K_D$ of target binding nucleic acids can be as little as about 10 picomolar or can be higher. It is within the present invention that the $K_D$ values of individual nucleic acids binding to SDF-1 is preferably within this range. Preferred ranges can be defined by choosing any first number within this range and any second number within this range. Preferred upper $K_D$ values are 250 nM and 100 nM, preferred lower $K_D$ values are 50 nM, 10 nM, 1 nM, 100 µM and 10 µM. The more preferred upper $K_D$ value is 2.5 nM, the more preferred lower $K_D$ value is 100 µM.

In addition to the binding properties of the nucleic acid molecules according to the present invention, the nucleic acid molecules according to the present invention inhibit the function of the respective target molecule which is in the present case SDF-1. The inhibition of the function of SDF-1—for instance the stimulation of the respective receptors as described previously—is achieved by binding of nucleic acid molecules according to the present invention to SDF-1 and forming a complex of a nucleic acid molecule according to the present invention and MCP-1 and SDF-1. Such complex of a nucleic acid molecule and SDF-1 cannot stimulate the receptors that normally are stimulated by SDF-1. Accordingly, the inhibition of receptor function by nucleic acid molecules according to the present invention is independent from the respective receptor that can be stimulated by SDF-1 but results from preventing the stimulation of the receptor by MCP-1 and SDF-1 by the nucleic acid molecules according to the present invention.

A possibility to determine the inhibitory constant of the nucleic acid molecules according to the present invention is the use of the methods as described in example 5 and 6 (for the CXCR4 and CXCR7, respectively) which confirms the above finding that the nucleic acids according to the present invention exhibit a favourable inhibitory constant which allows the use of said nucleic acids in a therapeutic treatment scheme. An appropriate measure in order to express the intensity of the inhibitory effect of the individual nucleic acid molecule on interaction of the target which is in the present case SDF-1 and the respective receptor, is the so-called half maximal inhibitory concentration (abbr. $IC_{50}$) which as such as well the method for its determination are known to the one skilled in the art.

Preferably, the $IC_{50}$ value shown by the nucleic acid molecules according to the present invention is below 1 µM. An $IC_{50}$ value of about 1 µM is said to be characteristic for a non-specific inhibition of target functions by a nucleic acid molecule. As will be acknowledged by the ones skilled in the art, the $IC_{50}$ value of a group of compounds such as the nucleic acid molecules according to the present invention is within a certain range. The above-mentioned $IC_{50}$ of about 1 μM is a preferred upper limit for the $IC_{50}$ value. The lower limit for the $IC_{50}$ of target binding nucleic acid molecules can be as little as about 10 picomolar or can be higher. It is within the present invention that the $IC_{50}$ values of individual nucleic acids binding to SDF-1 is preferably within this range. Preferred ranges can be defined by choosing any first number within this range and any second number within this range. Preferred upper $IC_{50}$ values are 250 nM and 100 nM, preferred lower $IC_{50}$ values are 50 nM, 10 nM, 1 nM, 100 pM and 10 pM. The more preferred upper $IC_{50}$ value is 2.5 nM, the more preferred lower $IC_{50}$ value is 100 pM.

The nucleic acid molecules according to the present invention may have any length provided that they are still able to bind to the target molecule. It will be acknowledged in the art that there are preferred lengths of the nucleic acids according to the present inventions. Typically, the length is between 15 and 120 nucleotides. It will be acknowledged by the ones skilled in the art that any integer between 15 and 120 is a possible length for the nucleic acids according to the present invention. More preferred ranges for the length of the nucleic acids according to the present invention are lengths of about 20 to 100 nucleotides, about 20 to 80 nucleotides, about 20 to 60 nucleotides, about 20 to 50 nucleotides and about 29 to 450 nucleotides.

It is within the present invention that the nucleic acids disclosed herein comprise a moiety which preferably is a high molecular weight moiety and/or which preferably allows to modify the characteristics of the nucleic acid in terms of, among others, residence time in the animal body, preferably the human body. A particularly preferred embodiment of such modification is PEGylation and HESylation of the nucleic acids according to the present invention. As used herein PEG stands for poly(ethylene glycole) and HES for hydroxyethly starch. PEGylation as preferably used herein is the modification of a nucleic acid according to the present invention whereby such modification consists of a PEG moiety which is attached to a nucleic acid according to the present invention. HESylation as preferably used herein is the modification of a nucleic acid according to the present invention whereby such modification consists of a HES moiety which is attached to a nucleic acid according to the present invention. These modifications as well as the process of modifying a nucleic acid using such modifications, is described in European patent application EP 1 306 382, the disclosure of which is herewith incorporated in its entirety by reference.

In the case of PEG being such high molecular weight moiety the molecular weight is preferably about 20,000 to about 120,000 Da, more preferably from about 30,000 to about 80,000 Da and most preferably about 40,000 Da. In the case of HES being such high molecular weight moiety the molecular weight is preferably from about 50 to about 1000 kDa, more preferably from about 100 to about 700 kDa and most preferably from 200 to 500 kDa. HES exhibits a molar substitution of 0.1 to 1.5, more preferably of 1 to 1.5 and exhibits a substitution sample expressed as the C2/C6 ratio of approximately 0.1 to 15, preferably of approximately 3 to 10. The process of HES modification is, e.g., described in German patent application DE 1 2004 006 249.8 the disclosure of which is herewith incorporated in its entirety by reference.

The modification can, in principle, be made to the nucleic acid molecules of the present invention at any position thereof. Preferably such modification is made either to the 5'-terminal nucleotide, the 3'-terminal nucleotide and/or any nucleotide between the 5' nucleotide and the 3' nucleotide of the nucleic acid molecule.

The modification and preferably the PEG and/or HES moiety can be attached to the nucleic acid molecule of the present invention either directly or indirectly, preferably through a linker. It is also within the present invention that the nucleic acid molecule according to the present invention comprises one or more modifications, preferably one or more PEG and/or HES moiety. In an embodiment the individual linker molecule attaches more than one PEG moiety or HES moiety to a nucleic acid molecule according to the present invention. The linker used in connection with the present invention can itself be either linear or branched. This kind of linkers are known to the ones skilled in the art and are further described in patent applications WO2005/074993 and WO2003/035665.

In a preferred embodiment the linker is a biodegradable linker. The biodegradable linker allows to modify the characteristics of the nucleic acid according to the present invention in terms of, among other, residence time in an animal body, preferably in a human body, due to release of the modification from the nucleic acid according to the present invention. Usage of a biodegradable linker may allow a better control of the residence time of the nucleic acid according to the present invention. A preferred embodiment of such biodegradable linker is a biodegradable linker as described in, but not limited to, international patent applications WO2006052790, WO2008/034122, WO2004/092191 and WO2005/099768.

It is within the present invention that the modification or modification group is a biodegradable modification, whereby the biodegradable modification can be attached to the nucleic acid molecule of the present invention either directly or indirectly, preferably through a linker. The biodegradable modification allows to modify the characteristics of the nucleic acid according to the present invention in terms of, among other, residence time in an animal body, preferably in a human body, due to release or degradation of the modification from the nucleic acid according to the present invention. Usage of biodegradable modification may allow a better control of the residence time of the nucleic acid according to the present invention. A preferred embodiment of such biodegradable modification is biodegradable as described in, but not restricted to, international patent applications WO2002/065963, WO2003/070823, WO2004/113394 and WO2000/41647, preferably in WO2000/41647, page 18, line 4 to 24.

Beside the modifications as described above, other modifications can be used to modify the characteristics of the nucleic acids according to the present invention, whereby such other modifications may be selected from the group of proteins, lipids such as cholesterol and sugar chains such as amylase, dextran etc.

Without wishing to be bound by any theory, it seems that by modifying the nucleic acids according to the present invention with high molecular weight moiety such as a polymer and more particularly one or several of the polymers disclosed herein, which are preferably physiologically acceptable, the excretion kinetic is changed. More particularly, it seems that due to the increased molecular weight of such modified inventive nucleic acids and due to the nucleic acids of the invention not being subject to metabolism particularly when in the L form, excretion from an animal body, preferably from a mammalian body and more preferably from a human body is decreased. As excretion typically occurs via the kidneys, the present inventors assume that the glomerular filtration rate of the thus modified nucleic acids is significantly reduced compared to the nucleic acids not having this kind of high molecular weight modification which results in an increase in the residence time in the animal body. In connection therewith it is particularly noteworthy that, despite such high molecular weight modification the specificity of the nucleic acids according to the present invention is not affected in a detrimental manner. Insofar, the nucleic acids according to the present invention have among others, the surprising characteristic—which normally cannot be expected from pharmaceutically active compounds—such that a pharmaceutical formulation providing for a sustained release is not necessarily required to provide for a sustained release of the nucleic acids according to the present invention. Rather the nucleic acids according to the present invention in their modified form comprising a high molecular weight moiety, can as such already be used as a sustained release-formulation as they act, due to their modification, already as if they were released from a sustained-release formulation. Insofar, the modification(s) of the nucleic acid molecules according to the present invention as disclosed herein and the thus modified nucleic acid molecules according to the present invention and any composition comprising the same may provide for a distinct, preferably controlled pharmacokinetics and biodistribution thereof. This also includes residence time in circulation and distribution to tissues. Such modifications are further described in the patent application WO2003/035665.

However, it is also within the present invention that the nucleic acids according to the present invention do not comprise any modification and particularly no high molecular weight modification such as PEGylation or HESylation. Such embodiment is particularly preferred when the nucleic acid according to the present invention shows preferential distribution to any target organ or tissue in the body or when a fast clearance of the nucleic acid according to the present invention from the body after administration is desired. Nucleic acids according to the present invention as disclosed herein with a preferential distribution profile to any target organ or tissue in the body would allow establishment of effective local concentrations in the target tissue while keeping systemic concentration of the nucleic acids low. This would allow the use of low doses which is not only beneficial from an economic point of view, but also reduces unnecessary exposure of other tissues to the nucleic acid agent, thus reducing the potential risk of side effects. Fast clearance of the nucleic acids according to the present invention from the body after administration might be desired, among others, in case of in vivo imaging or specific therapeutic dosing requirements using the nucleic acids according to the present invention or medicaments comprising the same.

The nucleic acids according to the present invention, and/or the antagonists according to the present invention may be used for the generation or manufacture of a medicament. Such medicament or a pharmaceutical composition according to the present invention contains at least one of the inventive nucleic acids selected from the group of SDF-1 binding nucleic acids, optionally together with further pharmaceutically active compounds, whereby the inventive nucleic acid preferably acts as pharmaceutically active compound itself. Such medicaments comprise in preferred embodiments at least a pharmaceutically acceptable carrier. Such carrier may be, e.g., water, buffer, PBS, glucose solution, preferably a 5% glucose salt balanced solution, starch, sugar, gelatine or any other acceptable carrier substance. Such carriers are generally known to the one skilled in the art. It will be acknowledged by the person skilled in the art that any embodiments, use and aspects of or related to the medicament of the present invention is also applicable to the pharmaceutical composition of the present invention and vice versa.

The indication, diseases and disorders for the treatment and/or prevention of which the nucleic acids, the pharmaceutical compositions and medicaments in accordance with or prepared in accordance with the present invention result from the involvement, either direct or indirect, of SDF-1 in the respective pathogenetic mechanism.

Of course, because the SDF-1 binding nucleic acids according to the present invention interact with or bind to human or murine SDF-1, a skilled person will generally understand that the SDF-1 binding nucleic acids according to the present invention can easily be used for the treatment, prevention and/or diagnosis of any disease as described herein of humans and animals. In connection therewith, it is to be acknowledged that the nucleic acid molecules according to the present invention can be used for the treatment and prevention of any of the diseases, disorder or condition described herein, irrespective of the mode of action underlying such disease, disorder and condition.

In the following the rational for the use of the nucleic acid molecules according to the present invention in connection with the various diseases, disorders and conditions is provided, thus rendering the claimed therapeutic, preventive and diagnostic applicability of the nucleic acid molecules according to the present invention plausible. In order to avoid any unnecessary repetition, it should be acknowledged that due to the involvement of the SDF-1-SDF-1 receptor axis as outlined in connection therewith said axis may be addressed by the nucleic acid molecules according to the present invention such that the claimed therapeutic, preventive and diagnostic effect is achieved. It should furthermore be acknowledged that the particularities of the diseases, disorders and conditions, of the patients and any detail of the treatment regimen described in connection therewith, may be subject to preferred embodiments of the instant application.

For haematological malignancies, in particular, there is considerable evidence that leukemia cells may be protected from conventional therapies (chemotherapy combined with various targeted agents such as specific antibodies or kinase inhibitors) within particular tissue microenvironments, referred to as niches. Such niches are found particularly in the bone marrow where they can harbour malignant cells that are then able to expand and produce a relapse following the initial therapy (Burger and Kipps, 2002; Burger and Burkle, 2007; Meads et al., 2008; Burger, Ghia et al., 2009). This preservation of malignant cells during chemotherapy is thought to be largely due to direct contact between the malignant cells and stromal cells (Lagneaux, Delforge et al. 1998; Kurtova, Balakrishman at al., 2009; Damiano, Cress et al., 1999) however in the complexity of this microenvironment there are multiple cellular and molecular signals that may lead to resistance of the malignant cells to chemotherapy. Despite this complexity it is clear that stromal cells produce the chemokine SDF-1 and that both normal and malignant cells that express CXCR4 migrate to and are held in such niches. That this molecular pathway is key for this interaction is demonstrated by the fact that specific inhibition of this interaction is sufficient to release both normal and malignant cells from the niches (Broxmeyer, Orschell at al., 2005; Devine, Flomenberg et al., 2004; Azab, Runnels et al., 2009). In addition to weakening the interaction with the niches it has been shown for numerous hematological malignancies that disruption of the SDF-1-CXCR4 axis results in increasing the vulnerability of the cells to other therapies—so called 'chemosensitization'. This chemosensitization has been described for multiple myeloma (Azab, Runnels at al., 2009) and various acute and chronic leukemias (Dillmann, Veldwijk et al., 2009; Lagneaux, Delforge et al. 1998).

Therefore use of SDF-1 binding nucleic acids according to the present invention to disrupt cross talk between malignant cells and their milieu to sensitize them to other therapies is an attractive strategy for the treatment of haematological malignancies. Examples of therapies that can be enhanced by combination with SDF-1 binding nucleic acids according to the present invention include the following but not limited to Fludarabine, Cyclophosphamide, Rituxan, Chlorambucil, Lenalidomide, Bortezomib, Dexamethasone, Melphalan, Imatinib or Nilotinib.

The foregoing description emphasized the role of bone marrow stromal cells and bone marrow niches in the protection of malignant cells from the effects of chemotherapy or other targeted therapies for haematological malignancies. However there is evidence for similar interactions occurring locally within solid tumors as a large proportion of the cells in solid tumors are not cancer cells but rather stromal, immune or vascular cells derived from the host that interact intimately with the tumor cells. Many different types of solid tumors express CXCR4 (Engl, Relja et al., 2006; Müller, Homey et al., 2001; Koshiba, Hosotani et al., 2000, Ehtesham, Stevenson, et al., 2008; Zeelenberg, Ruuls-Van Stalle et al., 2003; Sauer, Seidler et al., 2005; Su, Zhang et al., 2005) and/or CXCR7 (Burns, Summers et al. 2006; Miao et al., 2007; Wang et al., 2008; Zheng, Li et al., 2010) receptors either constitutively or in response to hypoxia or various treatments. Malignant cells may use this signaling pathway for survival and migration by activation of Akt and Erk. SDF-1 can be produced by the malignant cells themselves or by the stromal cells within the tumor. Once again in this complex environment the exact mechanism by which tumour cells grow and escape from chemotherapy or other therapeutic approaches are not clearly defined. However it is clear that the SDF-1-CXCR4 axis and the SDF-1-CXCR7 play an important role. For example inhibition of CXCR4 sensitizes glioma cell lines to in vitro chemotherapy (Redjal et al., 2006) and high expression of CXCR4 is predictive of poor outcome in breast cancer (Holm, Abreo et al., 2008; Mizell, Smith et al., 2009) and gastro-intestinal cancers (Schimanski et al., 2008). Therefore the use of SDF-1 binding nucleic acids according to the present invention to inhibit the action of SDF-1 on either CXCR4 or CXCR7 receptors in a wide variety of solid tumors will enhance current therapy by making the cells more vulnerable to the therapy either by direct action or by blocking interactions with other cells in the tumor.

In addition to the above aspects CXCR4 also conveys signals that are thought to be critical for recruitment and retention of pro-angiogenic and immunosuppressive bone marrow-derived cells (BMDCs). This pathway may therefore also be used for VEGF-independent angiogenesis. As a consequence, blocking the SDF1-CXCR4 axis to sensitize tumors to anti-VEGF therapy or radiation has emerged as an attractive strategy treatment for solid cancers.

However, there is a concern that CXCR4 blockade may not be sufficient to block the effects of SDF-1, which may also bind to CXCR7 on cancer or stromal cells. For example, CXCR7 has been recently reported to be expressed in brain tumor cells and mediate anti-apoptotic effects, and has also been shown to regulate the invasion, angiogenesis and tumor growth of human hepatocellular carcinomas. In such cases the action of SDF-1 binding nucleic acids to block the action of SDF-1 on both the CXCR7 and CXCR4 receptors in a single agent would provide a particular efficacy compared to specific receptor blockers.

The medicament according to the present invention may be used in combination with a further medicament or a further pharmaceutically active agent, whereby the further medicament or the further pharmaceutically active agent damages, destroys and/or labels (the) cancer cells. If the nucleic acid molecule according to the present invention is used with a further medicament or a further pharmaceutically active agent, the therapy which is based on the nucleic acid molecule is preferably an adjunct therapy to the therapy making use of or being based on the further medicament or further pharmaceutically active agent. Such further medicament or further pharmaceutically active agent are preferably selected from but not restricted to the group comprising a) antibodies such as Rituximab (target: CD20), Cetuximab (target: epidermal growth factor receptor), Ibriumomab-Tiuxetan (target: CD20), Tositumomab (target: CD20), Trastuzumab (target: HER2/neu), Bevacizumab (target: VEGF), Alemtuzumab (target: CD52);

b) alkylating agents such as cisplatin, carboplatin, oxaliplatin, mechlorethamine, cyclophosphamide, chlorambucil, Doxorubicin, liposomal Doxorubicin, bendamustine, Melphalan, temozolomide c) anti-metabolites such as purineazathioprine, mercaptopurine, fludarabine, pentostatin, cladribine;

d) plant alkaloids such vinca alkaloids, plant terpenoids such as taxanes, preferably Docetaxel, Paclitaxel, podophyllotoxin, epothilone;

e) topoisomerase inhibitors such as camptothecins, irinitecan, mitoxantrone;

f) and other such as Leucovorin, Methotrexate, Tamoxifen, Sorafenib, Lenalidomide, Bortezomib, Dexamethasone, Flurouracil and Prendnisone.

Other agents that can be used as further pharmaceutically active agent in the treatment of cancer are well known in the art and include, but are not limited to immunosuppressive drugs, cytokines and cytostatic drugs (for reference: "Allgemeine und Spezielle Pharmakologie und Toxikologie 2011", editor. Thomas Karow; Pulheim, Germany). Such agents well known in the art are used in the treatment of cancer according to the current standard of care for the particular cancer patient population.

It will be acknowledged that the above specified further pharmaceutically active agents can be used in connection with each any aspect of the present invention which makes use of such further pharmaceutically active agent.

The further medicament or pharmaceutically active agent has or may provide the function of a chemotherapy. Alternatively or additionally to chemotherapy radiotherapy can be used.

The medicament according to the present invention, in combination with or without the further medicament or further pharmaceutically active agent, and with or without radiotherapy, can be used for the treatment and/or prevention of cancer, preferably a) hematological cancer, whereby more preferably the hematological cancer is selected from the group of leukemia, and myeloma.

b) solid tumors, whereby more solid tumors are selected from the group of glioblastoma, colorectal cancer, breast cancer, lymphoma, prostate cancer, pancreatic cancer, lung cancer, renal cancer, and ovarian cancer Preferably breast cancer is selected from the group of advanced HER2-negative breast cancer.

Preferably leukemia is selected from the group of chronic lymphoid leukemia and acute myeloid leukemia.

Preferably myeloma is selected from the group of multiple myeloma.

The preferred further medicament or a further pharmaceutically active agent for the treatment of Glioblastoma is radiotherapy or chemotherapy with temozolomide or therapy with bevacizumab. The preferred further medicament or a further pharmaceutically active agent for the treatment of colorectal cancer is selected from the group comprising fluorouracil, Leucovorin, Oxaliplatin, Irinotecan and bevacizumab.

The preferred further medicament or a further pharmaceutically active agent for the treatment of advanced HER2-negative breast cancer is selected from the group of Doxorubicin, Paclitaxel, Docetaxel, Methotrexate, Fluorouracil, Bevacizumab, Tamoxifen, and aromatase inhibitors.

The preferred further medicament or a further pharmaceutically active agent for the treatment of chronic lymphoid leukemia is selected from the group comprising fludarabine, cyclophosphamide, rituximab, Chlorambucil, alemtuzumab, vincristine, pentostatin, mitoxantrone, doxorubicin, cladribine, and bendamustine.

The preferred further medicament or a further pharmaceutically active agent for the treatment of multiple myeloma is selected from the group comprising Lenalidomide, Bortezomib, Dexamethasone, Melphalan, Cyclophosphamide, liposomal doxorubicin, and prednisone.

In one embodiment of the medicament of the present invention, such medicament is for use in combination with other treatments for any of the diseases disclosed herein, particularly those for which the medicament of the present invention is to be used.

"Combination therapy" (or "co-therapy") includes the administration of a medicament of the invention and at least a second or further agent as part of a specific treatment regimen intended to provide the beneficial effect from the co-action of these therapeutic agents, i.e. the medicament of the present invention and said second or further agent. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may be, but generally is not, intended to encompass the administration of two or more of these therapeutic agents as part of separate monotherapy regimens. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to a subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, topical routes, oral routes, intravenous mutes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the therapeutic agents are administered is not narrowly critical unless noted otherwise. "Combination therapy" also can embrace the administration of the therapeutic agents as described above in further combination with other biologically active ingredients. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

As outlined in general terms above, the medicament according to the present invention can be administered, in principle, in any form known to the ones skilled in the art. A preferred route of administration is systemic administration, more preferably by parenteral administration, preferably by injuction. Alternatively, the medicament may be administered locally. Other routes of administration comprise intramuscular, intraperitoneal, and subcutaneous, per orum, intranasal, intratracheal or pulmonary with preference given to the route of administration that is the least invasive, while ensuring efficiancy.

Parenteral administration is generally used for subcutaneous, intramuscular or intravenous injections and infusions. Additionally, one approach for parenteral administration employs the implantation of a slow-release or sustained-released systems, which assures that a constant level of dosage is maintained, that are well known to the ordinary skill in the art.

Furthermore, preferred medicaments of the present invention can be administered in intranasal form via topical use of suitable intranasal vehicles, inhalants, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels.

Subjects that will respond favorably to the method of the invention include medical and veterinary subjects generally, including human beings and human patients. Among other subjects for whom the methods and means of the invention are useful are cats, dogs, large animals, avians such as chickens, and the like.

The medicament of the present invention will generally comprise an effective amount of the active component(s) of the therapy, including, but not limited to, a nucleic acid molecule of the present invention, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the medicament of the present invention.

In a further aspect the present invention is related to a pharmaceutical composition. Such pharmaceutical composition comprises at least one of the nucleic acids according to the present invention and preferably a pharmaceutically acceptable binder. Such binder can be any binder used and/or known in the art. More particularly such binder is any binder as discussed in connection with the manufacture of the medicament disclosed herein. In a further embodiment, the pharmaceutical composition comprises a further pharmaceutically active agent.

The preparation of a medicament and a pharmaceutical composition will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, a medicament will be administered in a manner compatible with the dosage formulation, and in such amount as is pharmacologically effective. The formulations are easily administered in a variety of dosage forms, such as the type of injectable solutions described above, but drug release capsules and the like can also be employed.

The medicament of the invention can also be administered in oral dosage forms as timed release and sustained release tablets or capsules, pills, powders, granules, elixirs, tinctures, suspensions, syrups and emulsions. Suppositories are advantageously prepared from fatty emulsions or suspensions.

The pharmaceutical composition or medicament may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

The medicaments and nucleic acid molecules, respectively, of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, what is well known to the ordinary skill in the art. For example, the nucleic acid molecules described herein can be provided as a complex with a lipophilic compound or non-immunogenic, high molecular weight compound constructed using methods known in the art. Additionally, liposomes may bear such nucleic acid molecules on their surface for targeting and carrying cytotoxic agents internally to mediate cell killing. An example of nucleic-acid associated complexes is provided in U.S. Pat. No. 6,011,020.

The medicaments and nucleic acid molecules, respectively, of the present invention may also be coupled with soluble polymers as targetable drug carriers. Such polymers can include polyvinylpyrrolidone, pyran copolymer, polyhydroxypropyl-methacrylamide-phenol, polyhydroxyethyl-aspanamidephenol, or polyethyleneoxidepolylysine substituted with palmitoyl residues. Furthermore, the medicaments and nucleic acid molecules, respectively, of the present invention may be coupled to a class of biodegradable polymers useful in achieving controlled release of a drag, for example, polylactic acid, polyepsilon capro lactone, polyhydroxy butyric acid, polyorthoesters, polyacetals, polydihydropyrans, polycyanoacrylates and cross-linked or amphipathic block copolymers of hydrogels.

If desired, the pharmaceutical composition and medicament, respectively, to be administered may also contain minor amounts of non-toxic auxiliary substances such as wetting or emulsifying agents, pH buffering agents, and other substances such as for example, sodium acetate, and triethanolamine oleate.

The dosage regimen utilizing the nucleic acid molecules and medicaments, respectively, of the present invention is selected in accordance with a variety of factors including type, species, age, weight, sex and medical condition of the patient; the severity of the condition to be treated; the route of administration; the renal and hepatic function of the patient; and the particular aptamer or salt thereof employed. An ordinarily skilled physician or veterinarian can readily determine and prescribe the effective amount of the drug required to prevent, counter or arrest the progress of the condition.

Effective plasma levels of the nucleic acid according to the present invention preferably range from 500 fM to 200 µM, preferably from 1 nM to 20 µM, more preferably from 5 nM to 20 µM, most preferably 50 nM to 20 µM in the treatment of any of the diseases disclosed herein.

The nucleic acid molecules and medicaments, respectively, of the present invention may preferably be administered in a single daily dose, every second or third day, weekly, every second week, in a single monthly dose or every third month.

It is within the present invention that the medicament as described herein constitutes the pharmaceutical composition disclosed herein.

In a further aspect the present invention is related to a method for the treatment of a subject who is in need of such treatment, whereby the method comprises the administration of a pharmaceutically active amount of at least one of the nucleic acids according to the present invention. In an embodiment, the subject suffers from a disease or is at risk to develop such disease, whereby the disease is any of those disclosed herein, particularly any of those diseases disclosed in connection with the use of any of the nucleic acids according to the present invention for the manufacture of a medicament.

As preferably used herein, the term treatment comprises in a preferred embodiment additionally or alternatively prevention and/or follow-up.

As preferably used herein, the terms disease and disorder shall be used in an interchangeable manner, if not indicated to the contrary.

As used herein, the term comprise is preferably not intended to limit the subject matter followed or described by such term. However, in an alternative embodiment the term comprises shall be understood in the meaning of containing and thus as limiting the subject matter followed or described by such term.

The various SEQ ID NOs:, the chemical nature of the nucleic acid molecules according to the present invention and the target molecules SDF-1 as used herein, the actual sequence thereof and the internal reference number is summarized in the following table. It has to be noticed that the nucleic acids were characterized on the aptamer, i.e. D-nucleic acid level (D-RNA) with the biotinylated human D-SDF-1 (SEQ ID NO: 4) or on the Spiegelmer level, i.e. L-nucleic acid (L-RNA) with the natural configuration of SDF-1, the L-SDF-1 (human SDF-1α, SEQ ID NO: 1). The different nucleic acids share one internal reference name but one SEQ ID Nos: for the D-RNA (Aptamer) molecule and one SEQ ID Nos: for the L-RNA (Spiegelmer) molecule, respectively.

TABLE 1

| SEQ ID NO: | RNA/Peptide | Sequence | Internal Reference |
|---|---|---|---|
| 1 | L-peptide | KPVSLSYRCPCRFFESHVARANVKHLKILNTPNCALQIVARLKNNNR QVCIDPKLKWIQEYLEKLNK | human/monkey/cat SDF-1α<br>human/monkey/cat SDF-1 |
| 2 | L-peptide | KPVSLSYRCPCRFFESHVARANVKHLKILNTPNCALQIVARLKNNNR QVCIDPKLKWIQEYLEKALNKRFKM | human/monkey/cat SDF-1β |
| 3 | L-peptide | KPVSLSYRCRCRFFESHIARANVKHLKILNTPNCALQIVARLKNNNR QVCIDPKLKWIQEYLEKALNK | murine SDF-1α<br>murine SDF-1 |
| 4 | D-peptide | KPVSLSYRCPCRFFESHVARANVKHLKILNTPNCALQIVARLKNNNR QVCIDPKLKWIQEYLEKALNKRFK-Biotin | biotinylated hu D-SDF-1 |
| 5 | L-RNA | AGCGUGGUGUGAUCUAGAUGUAGUGGCUGAUCCUAGUCAGGUACGCU | 193-C2-001 |
| 6 | L-RNA | AGCGUGGUGUGAUCUAGAUGUAUUGGCUGAUCCUAGUCAGGUACGCU | 193-G2-001 |
| 7 | L-RNA | AGCGUGGUGUGAUCUAGAUGUAAUGGCUGAUCCUAGUCAGGUGCGCU | 193-F2-001 |
| 8 | L-RNA | GCGAGGUGUGAUCUAGAUGUAGUGGCUGAUCCUAGUCAGGUGCGC | 193-G1-002 |
| 9 | L-RNA | GCGUGGUGUGAUCUAGAUGUAGUGGCUGAUCCUAGUCAGGUGCGC | 193-D2-002 |
| 10 | L-RNA | GCAUGGUGUGAUCUAGAUGUAGUGGCUGAUCCUAGUCAGGUGCCC | 193-A1-002 |
| 11 | L-RNA | GCGUGGUGUGAUCUAGAUGUAAUGGCUGAUCCUAGUCAGGGACGC | 193-D3-002 |
| 12 | L-RNA | GCGUGGUGUGAUCUAGAUGUAGAGGCUGAUCCUAGUCAGGUACGC | 193-B3-002 |
| 13 | L-RNA | GCGUGGUGUGAUCUAGAUGUAAAGGCUGAUCCUAGUCAGGUACGC | 193-H3-002 |
| 14 | L-RNA | GUGGUGUGAUCUAGAUGUAGUGGCUGUUCCUAGUCAGGUAUGC | 193-E3-002 |
| 15 | L-RNA | GCGUGGUGUGAUCUAGAUGUAGUGGCUGAUCCUAGUUAGGUACGC | 193-D1-002 |
| 16 | L-RNA | GCGUGGUGUGAUCUAGAUGUAGUGGCUCAUCCUAGUCAGGUACGC | 193-C2-002 |
| 17 | L-RNA | CGUGGUGUGAUCUAGAUGUAGUGGCUGAUCCUAGUCAGGUACG | 193-C2-003 |
| 18 | L-RNA | GUGGUGUGAUCUAGAUGUAGUGGCUGAUCCUAGUCAGGUAC | 193-C2-004 |
| 19 | L-RNA | UGGUGUGAUCUAGAUGUAGUAGUGGCUGAUCCUAGUCAGGUA | 193-C2-005 |
| 20 | L-RNA | GGUGUGAUCUAGAUGUAGUGGCUGAUCCUAGUCAGGU | 193-C2-006 |
| 21 | L-RNA | GUGUGAUCUAGAUGUAGUGGCUGAUCCUAGUCAGG | 193-C2-007 |
| 22 | L-RNA | GCGUGGUGUGAUCUAGAUGUAUUGGCUGAUCCUAGUCAGGUACGC | 193-G2-012 |
| 23 | L-RNA | GCGCGGUGUGAUCUAGAUGUAUUGGCUGAUCCUAGUCAGGCGCGC | 193-G2-013 |
| 24 | L-RNA | GCGCGUGUGAUCUAGAUGUAUUGGCUGAUCCUAGUCAGGGCGC | 193-G2-014 |
| 25 | L-RNA | GGGCGUGUGAUCUAGAUGUAUUGGCUGAUCCUAGUCAGGGCCC | 193-G2-015 |
| 26 | L-RNA | GGCCGUGUGAUCUAGAUGUAUUGGCUGAUCGUAGUCAGGGGCC | 193-G2-016 |
| 27 | L-RNA | GCCCGUGUGAUCUAGAUGUAUUGGCUGAUCCUAGUCAGGGGGC | 193-G2-017 |
| 28 | L-RNA | 5'-40 kDa-PEG-GCGUGGUGUGAUGUAGAUGUAUUGGCUGAUCCUAGUCAGGUACGC | 193-G2-012-5'-PEG, NOX-A12 |
| 29 | D-RNA | AGCGUGGUGUGAUCUAGAUGUAGUGGCUGAUCCUAGUCAGGUACGCU | 193-C2-001 |
| 30 | D-RNA | AGCGUGGUGUGAUCUAGAUGUAUUGGCUGAUCCUAGUCAGGUACGCU | 193-G2-001 |

TABLE 1-continued

| SEQ ID NO: | RNA/Peptide | Sequence | Internal Reference |
|---|---|---|---|
| 31 | D-RNA | AGCGUGGUGUGAUCUAGAUGUAAUGGCUGAUCCUAGUCAGGUGCGCU | 193-F2-001 |
| 32 | D-RNA | GCGAGGUGUGAUCUAGAUGUAGUGGCUGAUCCUAGUCAGGUGCGC | 193-G1-002 |
| 33 | D-RNA | GCGUGGUGUGAUCUAGAUGUAGUGGCUGAUCCUAGUCAGGUGCGC | 193-D2-002 |
| 34 | D-RNA | GCAUGGUGUGAUCUAGAUGUAGUGGCUGAUCCUAGUCAGGUGCCC | 193-A1-002 |
| 35 | D-RNA | GCGUGGUGUGAUCUAGAUGUAAUGGCUGAUCCUAGUCAGGGACGC | 193-D3-002 |
| 36 | D-RNA | GCGUGGUGUGAUCUAGAUGUAGAGGCUGAUCCUAGUCAGGUACGC | 193-B3-002 |
| 37 | D-RNA | GCGUGGUGUGAUCUAGAUGUAAAGGCUGAUCCUAGUCAGGUACGC | 193-H3-002 |
| 38 | D-RNA | GUGGUGUGAUCUAGAUGUAGUGGCUGUUCCAUGUCAGGUAUGC | 193-E3-002 |
| 39 | D-RNA | GCGUGGUGUGAUCUAGAUGUAGUGGCUGAUCCUAGUUAGGUACGC | 193-D1-002 |
| 40 | D-RNA | GCGUGGUGUGAUCUAGAUGUAGUGGCUGAUCCUAGUCAGGUACGC | 193-C2-002 |
| 41 | D-RNA | CGUGGUGUGAUCUAGAUGUAGUGGCUGAUCCUAGUCAGGUACG | 193-C2-003 |
| 42 | D-RNA | GUGGUGUGAUCUAGAUGUAGUGGCUGAUCCUAGUCAGGUAC | 193-C2-004 |
| 43 | D-RNA | UGGUGUGAUCUAGAUGUAGUGGCUGAUCCUAGUCAGGUA | 193-02-005 |
| 44 | D-RNA | GGUGUGAUCUAGAUGUAGUGGCUGAUCCUAGUCAGGU | 193-C2-006 |
| 45 | D-RNA | GUGUGAUCUAGAUGUAGUGGCUGAUCCUAGUCAGG | 193-C2-007 |
| 46 | D-RNA | GCGUGGUGUGAUCUAGAUGUAUUGGCUGAUCCUAGUGAGGUACGC | 193-G2-012 |
| 47 | D-RNA | GCGCGGUGUGAUCUAGAUGUAUUGGCUGAUCCUAGUCAGGCGCGC | 193-G2-013 |
| 48 | D-RNA | GCGCGUGUGAUCUAGAUGUAUUGGCUGAUCCUAGUCAGGGCGC | 193-G2-014 |
| 49 | D-RNA | GGGCGUGUGAUCUAGAUGUAUUGGCUGAUCCUAGUCAGGGCCC | 193-G2-015 |
| 50 | D-RNA | GGCCGUGUGAUCUAGAUGUAUUGGCUGAUCCUAGUCAGGGGCC | 193-G2-016 |
| 51 | D-RNA | GCCCGUGUGAUCUAGAUGUAUUGGCUGAUCCUAGUCAGGGGGC | 193-G2-017 |
| 52 | L-RNA | GUGUGAUCUAGAUGUADWGGCUGWUCCUAGUYAGG | Type B Formula-1 |
| 53 | L-RNA | GUGUGAUCUAGAUGUADUGGCUGAUCCUAGUCAGG | Type B Formula-2 |
| 54 | L-RNA | AAAGUAACACGUAAAAUGAAAGGUAAC | |
| 55 | L-RNA | AAAGCAACAUGUCAAUGAAAGGUAGC | |
| 56 | L-RNA | GGUUAGGGGUAAAGUCGG | |
| 57 | L-RNA | GGUUAGGGCUAGAAGUCGG | |
| 58 | L-RNA | GGUUAGGGCUCGAAGUCGG | |
| 59 | L-RNA | GGUUAGGGCUUGAAGUCGG | |
| 60 | L-RNA | GCUGUGAAAGCAACAUGUCAAUGAAAGGUAGCCGCAGC | 192-A10-001 |
| 61 | L-RNA | GCUGUGAAAGUAACAUGUCAAUGAAAGGUAACCACAGC | 192-G10 |
| 62 | LRNA | GCUGUGAAAGUAACACGUCAAUGAAAGGUAACCGCAGC | 192-F10 |
| 63 | L-RNA | GCUGUGAAAGUAACACGUCAAUGAAAGGUAACCACAGC | 192-B11 |
| 64 | L-RNA | GCUGUAAAGUAACAUGUCAAUGAAAGGUAACUACAGC | 192-C9 |
| 65 | L-RNA | GCUGUAAAGUAACAAGUCAAUGAAAGGUAACUACAGC | 192-E10 |
| 66 | L-RNA | GCUGUGAAAGUAACAAGUCAAUGAAAGGUAACCACAGC | 192-C10 |
| 67 | L-RNA | GCAGUGAAAGUAACAUGUCAAUGAAAGGUAACCACAGC | 192-D11 |
| 68 | L-RNA | GCUGUGAAAGUAACAUGUCAAUGAAAGGUAACCACUGC | 192-G11 |
| 69 | L-RNA | GCUAUGAAAGUAACAUGUCAAUGAAAGGUAACCAUAGC | 192-H11 |

TABLE 1-continued

| SEQ ID NO: | RNA/Peptide | Sequence | Internal Reference |
|---|---|---|---|
| 70 | L-RNA | GCUGCGAAAGCGACAUGUCAAUGAAAGGUAGCCGCAGC | 192-D10 |
| 71 | L-RNA | GCUGUGAAAGCAACAUGUCAAUGAAAGGUAGCCACAGC | 192-E9 |
| 72 | L-RNA | GCUGUGAAAGUAACAUGUCAAUGAAAGGUAGCCGCAGC | 192-H9 |
| 73 | L-RNA | AGCGUGAAAGUAACACGUAAAAUGAAAGGUAACCACGCU | 191-A6 |
| 74 | L-RNA | AAAGYRACAHUMAAX$_A$UGAAAGGUARC; X$_A$ = A or absent | Type A Formula-1 |
| 75 | L-RNA | AAGYRACAHGUMAAUGAAAGGUARC | Type A Formula-2 |
| 76 | L-RNA | AAAGYRACAHGUMAUGAAAGGUARC | Type A Formula-3 |
| 77 | L-RNA | AAAGYAACAHGUCAAUGAAAGGUARC | Type A Formula-4 |
| 78 | L-RNA | CUGUGAAAGCAACAUGUCAAUGAAAGGUAGCCGCAG | 192-A10-002 |
| 79 | L-RNA | UGUGAAAGCAACAUGUCAAUGAAAGGUAGCCGCA | 192-A10-003 |
| 80 | L-RNA | GUGAAAGCAACAUGUCAAUGAAAGGUAGCCGC | 192-A10-004 |
| 81 | L-RNA | UGAAAGCAACAUGUCAAUGAAAGGUGCCG | 192-A10-005 |
| 82 | L-RNA | GAAAGCAACAUGUCAAUGAAAGGUAGCC | 192-10-006 |
| 83 | r-RNA | AAAGCAACAUGUCAAUGAAAGGUAGC | 192-A10-007 |
| 84 | L-RNA | GCGUGAAAGCAACAUGUCAAUGAAAGGUAGCCGCGC | 192-A10-008 |
| 85 | L-RNA | GCGCGAAAGCAACAUGUCAAUGAAAGGUAGCCGCGC | 192-A10-015 |
| 86 | L-RNA | GCGGAAAGCAACAUGUCAAUGAAAGGUAGCCGCGC | 192-A10-014 |
| 87 | L-RNA | CGUGAAAGCAACAUGUCAAUGAAAGGUAGCCGCG | 192-A10-016 |
| 88 | L-RNA | GCGCAAAGCAACAUGUCAAUGAAAGGUAGCGUGC | 192-A10-017 |
| 89 | L-RNA | GUGCAAAGCAACAUGUCAAUGAAAGGUAGCGCGC | 192-A10-018 |
| 90 | L-RNA | CGCGAAAGCAACAUGUCAAUGAAAGGUAGCCGUG | 192-A10-119 |
| 91 | L-RNA | GGGCAAAGCAACAUGUCAAGAAAGGUAGCGCCC | 192-A10-020 |
| 92 | L-RNA | GGCCAAAGCAACAUGUCAAUGAAAGGUAGCGGCC | 192-A10-021 |
| 93 | L-RNA | GCCCAAAGCAACAUGUCAAUGAAAGGUAGCGGGC | 192-A10-022 |
| 94 | L-RNA | CCCCAAAGCAACAUGUGAAUGAAAGGUAGCGGGG | 192-A10-023 |
| 95 | L-RNA | GUGCUGCGGGGGUUAGGGCUAGAAGUCGGCCUGCAGCAC | 197-B2 |
| 96 | L-RNA | AGCGUGGCGAGGUUAGGGCUAGAAGUCGGUCGACACGCU | 191-D5-001 |
| 97 | L-RNA | GUGUUGCGGAGGUUAGGGCUAGAAGUCGGUCAGCAGCAC | 197-H1 |
| 98 | L-RNA | CGUGCGGCCUAAGAGGUUAGGGCUUAAAGUCGGUUUUGGCCAACACG | 190-D3 |
| 99 | L-RNA | CGUGCGCUUGAGAUAGGGGUUAGGGCUUAAAGUCGGCUGAUUCUCACG | 190-A3-001 |
| 100 | L-RNA | CGUGAUUGGUGAGGGGUUAGGGCUUGAAGUGGGCCUUGUCCAGUCACG | 190-A2 |
| 101 | L-RNA | AGCGUGAAGGGGUUAGGGCUCGAAGUCGGCUGACACGCU | 191-A5 |
| 102 | L-RNA | GUGCUGCGGGGGUUAGGGCUCGAAGUCGGCCCGCAGCAC | 197-H3 |
| 103 | L-RNA | GUGUUCCGGGGGUUAGGGCUUGAAGUCGGCCGGCAGCAC | 197-B1 |
| 104 | L-RNA | GUGUUGCAGGGGUUAGGGCUUGAAGUCGGCCUGCAGCAC | 197-E3 |
| 105 | L-RNA | GUGCUGCGGGGGUUAGGGCUCAAAGUCGGCCUGCAGCAC | 197-H2 |
| 106 | L-RNA | GUGCUGCCGGGGUUAGGGCUAA-AGUCGGCCGACAGCAC | 197-D1 |

TABLE 1-continued

| SEQ ID NO: | RNA/Peptide | Sequence | Internal Reference |
|---|---|---|---|
| 107 | L-RNA | GUGCUGUGGGGGUCAGGGCUAGAAGUCGGCCUGCAGCAC | 197-D2 |
| 108 | L-RNA | GGUYAGGGCUHRX$_4$AGUCGG; X$_4$ = A or absent | Type C Formula-1 |
| 109 | L-RNA | GGUYAGGGCUHRAAGUCGG | Type C Formula-2 |
| 110 | L-RNA | GGUYAGGGCUHRAGUCGG | Type C Formula-3 |
| 111 | L-RNA | GGUUAGGGCUHGAAGUCGG | Type C Formula-4 |
| 112 | L-RNA | UGAGAUAGGGGUUAGGGCUUAAAGUCGGCUGAUUCUCA | 190-A3-003 |
| 113 | L-RNA | GAGAUAGGGGUUAGGGCUUAAAGUCGGCUGAUUCUC | 190-A3-004 |
| 114 | L-RNA | GGGGUUAGGGCUUAAAGUCGGCUGAUUCU | 190-A3-007 |
| 115 | L-RNA | GCGUGGCGAGGIJUAGGGCUAGAAGUCGGUCGACACGC | 191-D5-002 |
| 116 | L-RNA | CGUGGCGAGGUUAGGGCUAGAAGUCGGUCGACACG | 191-D5-003 |
| 117 | L-RNA | CGGGCGAGGUUAGGGCUAGAAGUCGGUCGACCG | 191-D5-004 |
| 118 | L-RNA | CGGGCGAGGUUAGGGCUAGAAGUCGGUCGCCCG | 191-D5-005 |
| 119 | L-RNA | CGGGGAGGUUAGGGCUAGAAGUCGGUCGCCG | 191-D5-006 |
| 120 | L-RNA | CGGGAGGUUAGGGCUAGAAGUCGGUCCCG | 191-05-007 |
| 121 | L-RNA | GGGAGGUUAGGGCUAGAAGUCGGUCCC | 191-D5-010 |
| 122 | L-RNA | CCGCGGUUAGGGCUAGAAGUCGGGCGG | 191-D5-017 |
| 123 | L-RNA | CCCGGGUUAGGGCUAGAAGUCGGCGGG | 191-D5-029 |
| 124 | L-RNA | GGCGGGUUAGGGCUAGAAGUCGGCGCC | 191-D5-024 |
| 125 | L-RNA | CCCGCGGUUAGGGCUAGAAGUCGGGCGGG | 191-D5-017-29a |
| 126 | L-RNA | GCCGCGGUUAGGGCUAGAAGUCGGGCGGC | 191-D5-017-29b |
| 127 | L-RNA | CCCCGGGUUAGGGCUAGAAGUCGGCGGGG | 191-05-019-29a |
| 128 | L-RNA | CGGCGGGUUAGGGCUAGAAGUCGGCGCCG | 191-D5-024-29a |
| 129 | L-RNA | GGGCGGGUUAGGGCUAGAAGUCGGCGCCC | 191-D5-024-29b |
| 130 | L-RNA | UGCUGCGGGGGUUAGGGCUAGAAGUCGGCCUGCAGCA | 197-B2-001 |
| 131 | L-RNA | GCUGCGGGGGUUAGGGCUAGAAGUCGGCCUGCAGC | 197-B2-002 |
| 132 | L-RNA | CUGCGGGGGUUAGGGCUAGAAGUCGGCCUGCAG | 197-B2-003 |
| 133 | L-RNA | UGCGGGGGUUAGGGCUAGAAGUCGGCCUGCA | 197-B2-004 |
| 134 | L-RNA | GCGGGGGUUAGGGCUAGAAGUCGGCCUGC | 197-B2-005 |
| 135 | L-RNA | GCCGGGGGUUAGGGCUAGAAGUCGGCCGGC | 197-B2-006 |
| 136 | L-RNA | GGCCGGGGUUAGGGCUAGAAGUCGGCCGGCC | 197-B2-006-31a |
| 137 | L-RNA | CGCCGGGGUUAGGGCUAGAAGUCGGCCGGCG | 197-B2-006-31b |
| 138 | L-RNA | RKSBUSNVGR | Type C Formula-5-5' |
| 139 | L-RNA | YYNRCASSMY | Type C Formula-5-3' |
| 140 | L-RNA | RKSBUGSVGR | Type C Formula-6-5' |
| 141 | L-RNA | YCNRCASSMY | Type C Formula-6- |
| 142 | L-RNA | CGUGGUCCGUUGUGUCAGGUCUAUUCGCCCGGGUGCAGGGCAUCCGCG | 194-A2-001 |
| 143 | L-RNA | GCAGUGUGACGCGGACGUGAUAGGACAGAGCUGAUCCCGCUCAGGUGAG | 196-B12-003 |
| 144 | L-RNA | CAACAGCAGUGUGACGCGGACGUGAUAGGACAGAGCUGAUCCCGCUCAG | 196-B12-004 |
| 145 | L-RNA | 5'-40 kDa-PEG-GCGUGAAAGCAACAUGUCAAUGAAAGGUAGCCGCGC | 192-A10-008-5'-PEG |

TABLE 1-continued

| SEQ ID NO: | RNA/Peptide | Sequence | Internal Reference |
|---|---|---|---|
| 146 | D-RNA | GCUGUGAAAGCAACAUGUCAAUGAAAGGUAGCCGCAGC | 192-A10-001 |
| 147 | D-RNA | GCUGUGAAAGUAACAUGUCAAUGAAAGGUAACCACAGC | 192-G10 |
| 148 | D-RNA | GCUGUGAAAGUAACACGUCAAUGAAAGGUAACCGCAGC | 192-F10 |
| 149 | D-RNA | GCUGUGAAAGUAACACGUCAAUGAAAGGUAACCACAGC | 192-B11 |
| 150 | D-RNA | GCUGUAAAGUAACAUGUCAAUGAAAGGUAACUACAGC | 192-C9 |
| 151 | D-RNA | GCUGUAAAGUAACAAGUCAAUGAAAGGUAACUACAGC | 192-E10 |
| 152 | D-RNA | GCUGUGAAAGUAACAAGUCAAUGAAAGGUAACCACAGC | 192-C10 |
| 153 | D-RNA | GCAGUGAAAGUAACAUGUCAAUGAAAGGUAACCACAGC | 192-D11 |
| 154 | D-RNA | GCUGUGAAAGUAACAUGUCAAUGAAAGGUAACCACUGC | 192-G11 |
| 155 | D-RNA | GCUAUGAAAGUAACAUGUCAAUGAAAGGUAACCAUAGC | 192-H11 |
| 156 | D-RNA | GCUGCGAAAGCGACAUGUCAAUGAAAGGUAGCCGCAGC | 192-D10 |
| 157 | D-RNA | GCUGUGAAAGCAACAUGUCAAUGAAAGGUAGCCACAGC | 192-E9 |
| 158 | D-RNA | GCUGUGAAAGUAACAUGUCAAUGAAAGGUAGCCGCAGC | 192-H9 |
| 159 | D-RNA | AGCGUGAAAGUAACACGUAAAAUGAAAGGUAACCACGCU | 191-A6 |
| 160 | D-RNA | CUGUGAAAGCAACAUGUCAAUGMAGGUAGCCGCAG | 192-A10-002 |
| 161 | D-RNA | UGUGAAAGCAACAUCUCAAUGAAAGGUAGCCGCA | 192-A10-003 |
| 162 | D-RNA | GUGAAAGCAACAUGUCAAUGAAAGGUAGCCGC | 192-A10-004 |
| 163 | D-RNA | UGAAAGCAACAUGUCAAUGAAAGGUAGCCG | 192-A10-005 |
| 164 | D-RNA | GAAAGCAACAUGUCAAUGAAAGGUAGCC | 192-A10-006 |
| 165 | D-RNA | AAAGCAACAUGUCAAUGAAAGGUAGC | 192-A10-007 |
| 166 | D-RNA | GCGUGAAAGCAACAUGUCAAUGAAAGGUAGCCGCGC | 192-A10-008 |
| 167 | D-RNA | GCGCGAAAGGAACAUGUCAAUGAAAGGUAGCCGCGC | 192-A10-015 |
| 168 | D-RNA | GCGGAAAGCAACAUGUCAAUGAAAGGUAGCCCGC | 192-A10-014 |
| 169 | D-RNA | CGUGAAAGCAACAUGUCAAUGAAAGGUAGCCGCG | 192-A10-016 |
| 170 | D-RNA | GCGCAAAGCAACAUGUCAAUGAAAGGUAGCGUGC | 192-A10-017 |
| 171 | D-RNA | GUGCAAAGCAACAUGUCAAUGAAAGGUAGCGCGC | 192-A10-018 |
| 172 | D-RNA | CGCGAAAGCAACAUGUCAAUGAAAGGUAGCCGUG | 192-A10-019 |
| 173 | D-RNA | GGGCAAAGCAACAUGUCAAUGAAAGGUAGCGCCC | 192-A10-020 |
| 174 | D-RNA | GGCCAAAGCAACAUGUCAAUGAAAGGUAGCGGCC | 192-A10-021 |
| 175 | D-RNA | GCCCAAAGCAACAUGUCAAUGAAAGGUAGCGGGC | 192-A10-022 |
| 76 | D-RNA | CCCCAAAGCAACAUGUCAAUGAAAGGUAGCGGGG | 192-A10-023 |
| 177 | D-RNA | GUGCUGCGGGGUUAGGGCUAGAAGUCGGCCUGCAGCAC | 197-B2 |
| 178 | D-RNA | AGCGUGGCGAGGUUAGGGCUAGAAGUCGGUCGACACGCU | 191-D5-001 |
| 179 | D-RNA | GUGUUGGGGAGGUUAGGGCUAGAAGUCGGUCAGCAGCAC | 197-H1 |
| 180 | D-RNA | CGUGCGGCCUAAGAGGUUAGGGCUUAAAGUCGGUCUUUGGCCAACACG | 190-D3 |
| 181 | D-RNA | CGUGCGCUUGAGAUAGGGGUUAGGGCUUAAAGUCGGCUGAUUCUCACG | 190-A3-001 |
| 182 | D-RNA | CGUGAUUGGUGAGGGGUUAGGGCUUGAAGUCGGCCUUGUCCAGUCACG | 190-A2 |

TABLE 1-continued

| SEQ ID NO: | RNA/Peptide | Sequence | Internal Reference |
|---|---|---|---|
| 183 | D-RNA | AGCGUGAAGGGGUUAGGGCUCGAAGUCGGCUGACACGCU | 191-A5 |
| 184 | D-RNA | GUGCUGCGGGGUUAGGGCUCGAAGUCGGCCCGCAGCAC | 197-H3 |
| 185 | D-RNA | GUGUUCCCGGGGUUAGGGCUUGAAGUCGGCCGGCAGCAC | 197-B1 |
| 186 | D-RNA | GUGUUGCAGGGGUUAGGGCUUGAAGUCGGCCUGCAGCAC | 197-E3 |
| 187 | D-RNA | GUGCUGCGGGGGUUAGGGCUCAAAGUCGGCCUGCAGCAC | 197-H2 |
| 188 | D-RNA | GUGCUGCCGGGGUUAGGGCUAA-AGUCGGCCGACAGCAC | 197-D1 |
| 189 | D-RNA | GUGCUGUGGGGGUCAGGGCUAGAAGUCGGCCUGCAGCAC | 197-02 |
| 190 | D-RNA | UGAGAUAGGGGUUAGGGCUUAAAGUCGGCUGAUUCUCA | 190-A3-003 |
| 191 | D-RNA | GAGAUAGGGGUUAGGGCUUAAAGUCGGCUGAUUCUC | 190-A3-004 |
| 192 | D-RNA | GGGGUUAGGGCUUAAAGUCGGCUGAUUCU | 190-A3-007 |
| 193 | D-RNA | GCGUGGCGAGGUUAGGGCUAGAAGUCGGUCGACACGC | 191-D5-002 |
| 194 | D-RNA | CGUGGCGAGGUUAGGGCUAGAAGUCGGUCGACACG | 191-D5-003 |
| 195 | D-RNA | CGGGCGAGGU0AGGGCUAGAAGUCGGUCGACCG | 191-D5-004 |
| 196 | D-RNA | CGGGCGAGGUUAGGGCUAGAAGUCGGUCGCCCG | 191-D05-005 |
| 197 | D-RNA | CGGCGAGGUUAGGGCUAGAAGUCGGUCGCCG | 191-D5-006 |
| 198 | D-RNA | CGGGAGGUUAGGGCUAGAAGUCGGUCCCG | 191-D5-007 |
| 199 | D-RNA | GGGAGGUUAGGGCUAGAAGUCGGUCCC | 191-D5-010 |
| 200 | D-RNA | CCGCGGUUAGGGCUAGAAGUCGGGCGG | 191-D5-017 |
| 201 | D-RNA | CCCGGGUUAGGGCUAGAAGUCGGCGGG | 191-D5-029 |
| 202 | D-RNA | GGCGGGUUAGGGCUAGAAGUCGGCGCC | 191-D5-024 |
| 203 | D-RNA | CCCGCGGUUAGGGCUAGAAGUCGGGCGGG | 191-D5-017-29a |
| 204 | D-RNA | GCCGCGGUUAGGGCUAGAAGUCGGGCGGC | 191-D5-017-29b |
| 205 | D-RNA | CCCCGGGUUAGGGCUAGAAGUCGGCGGGG | 191-D5-019-29a |
| 206 | D-RNA | CGGCGGGUUAGGGCUAGAAGUCGGCGCCG | 191-D5-024-29a |
| 207 | D-RNA | GGGCGGGUUAGCGCUAGAAGDCGGCGCCC | 191-D5-024-29b |
| 208 | D-RNA | UGCUGCGGGGUUAGGGCUAGAAGUCGGCCUGCAGCA | 197-B2-001 |
| 209 | D-RNA | GCUGGGGGGUUAGGGCUAGAAGUCGGCCUGCAGC | 197-82-002 |
| 210 | D-RNA | CUGCGGGGUUAGGGCUAGAAGUCGGCCUGCAG | 197-B2-003 |
| 211 | D-RNA | UGCGGGGUUAGGGCUAGAAGUCGGCCUGCA | 197-B2-004 |
| 212 | D-RNA | GCGGGGUUAGGGCUAGAAGUCGGCCUGC | 197-B2-005 |
| 213 | D-RNA | GCCGGGUUAGGGCUAGAAGUCGGCCGGC | 197-B2-006 |
| 214 | D-RNA | GGCCGGGUUAGGGCUAGAAGUCGGCCGGCC | 197-B2-006-31a |
| 215 | D-RNA | CGCCGGGGUUAGGGCUAGAAGUCGGCCGGCG | 197-B2-006-31b |
| 216 | D-RNA | CGUGGUCCGUUGUGUCAGGUCUAUUCGCCCCGGUGCAGGGCAUCCGCG | 194-A2-001 |
| 217 | D-RNA | GCAGUGUGACGCGGACGUGAUAGGACAGAGCUGAUCCCGCUCAGGUGAG | 196-B12-003 |
| 218 | D-RNA | CAACAGCAGUGUGACGCGGACGUGAUAGGACAGAGCUGAUCCCGCUCAG | 196-B12-004 |
| 219 | L-RNA | 5'-40 kDa-PEG-UAAGGAAACUCGGUCUGAUGCGGUAGCGCUGUGCAGAGCU | Control Spiegelmer |
| 220 | L-RNA | CGUGCGCUUGAGAUAGG | |

TABLE 1-continued

| SEQ ID NO: | RNA/Peptide | Sequence | Internal Reference |
|---|---|---|---|
| 221 | L-RNA | CUGAUUCUCACG | |
| 222 | L-RNA | CUGAUUCUCA | |
| 223 | L-RNA | 5'-40 kDa-PEG-GCCGGGGUUAGGGCUAGAAGUCGGCCGGC | 197-B2-006-5'-PEG |
| 224 | L-RNA | 5'-40 kDa-PEG-CGGGAGGUUAGGGCUAGAAGUCGGUCCCG | 191-D5-007-5'PEG |
| 225 | L-RNA | 5'-40 kDa-PEG-CGCAUGGACUGAUCCUAGUCGGUUAUGUAGAUCUAGUGUGGUGCG | revNOX-A12 |

The present invention is further illustrated by the figures, examples and the sequence listing from which further features, embodiments and advantages may be taken, wherein FIG. 1 shows an alignment of sequences of SDF-1 binding nucleic acid molecules of "type A"

FIGS. 2A+B show derivatives of SDF-1 binding nucleic acid molecule 192-A10.001 (SDF-1 binding nucleic acid molecules of "type A");

FIG. 3 shows an alignment of sequences of SDF-1 binding nucleic acid molecules of "type B";

FIGS. 4A+B show derivatives of SDF-1 binding nucleic acid molecules 193-C2-001 and 193-G2-001 (SDF-1 binding nucleic acid molecules of type B);

FIG. 5 shows an alignment of sequences of SDF-1 binding nucleic acid molecules of "type C";

FIG. 6 shows derivatives of SDF-1 binding nucleic acid molecule 190-A3001 (SDF-1 binding nucleic acid molecules of "type C");

Figure 10:
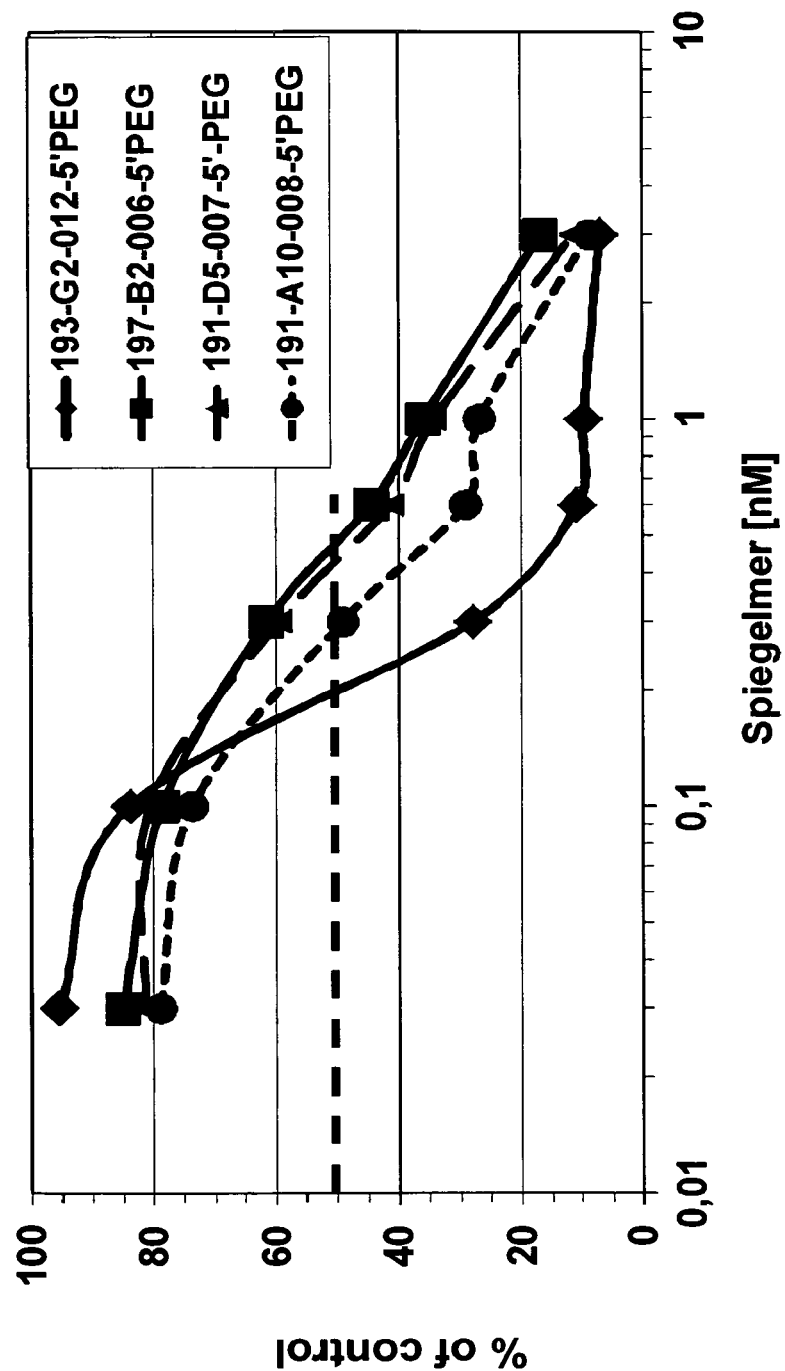
Figure 11A:
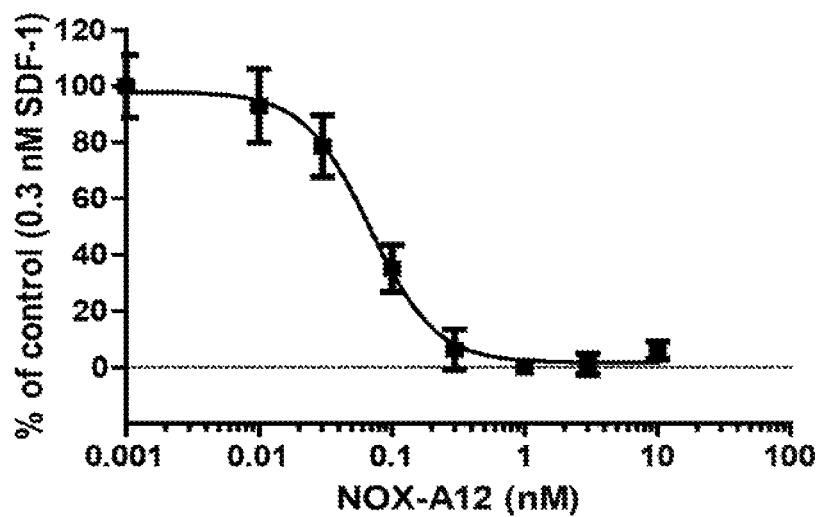
Figure 11B:
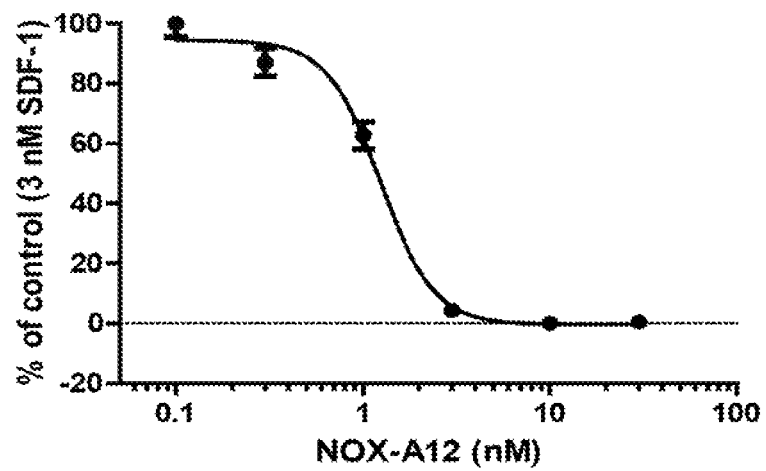
Figure 12:
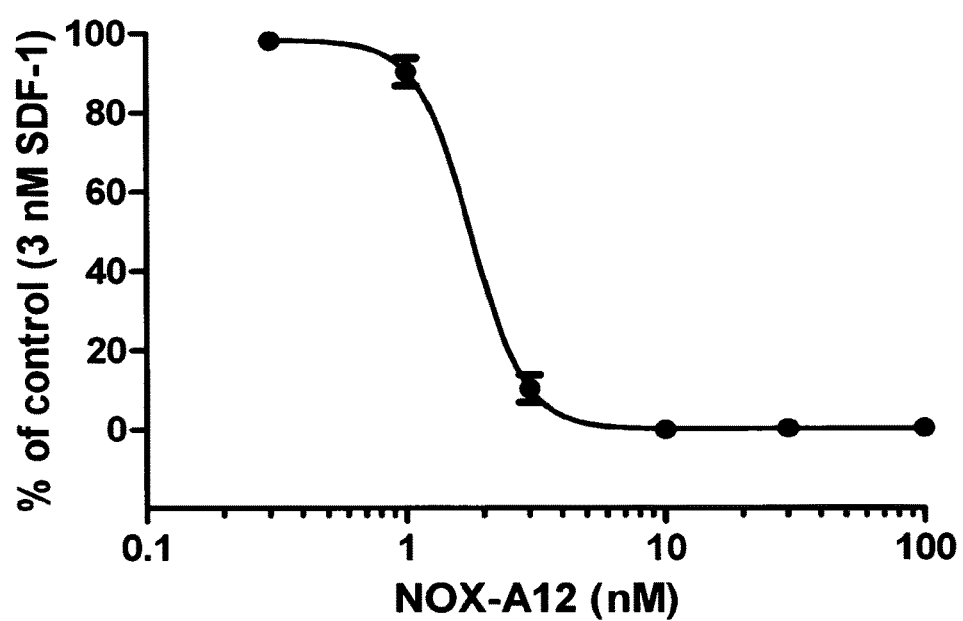
Figure 13:
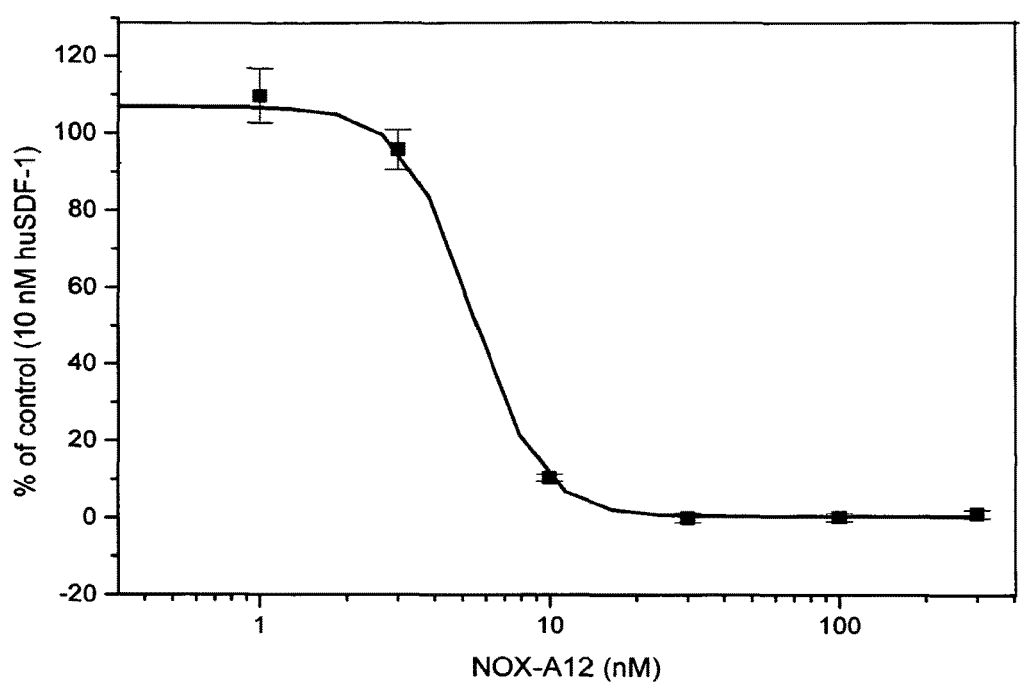
Figure 14:
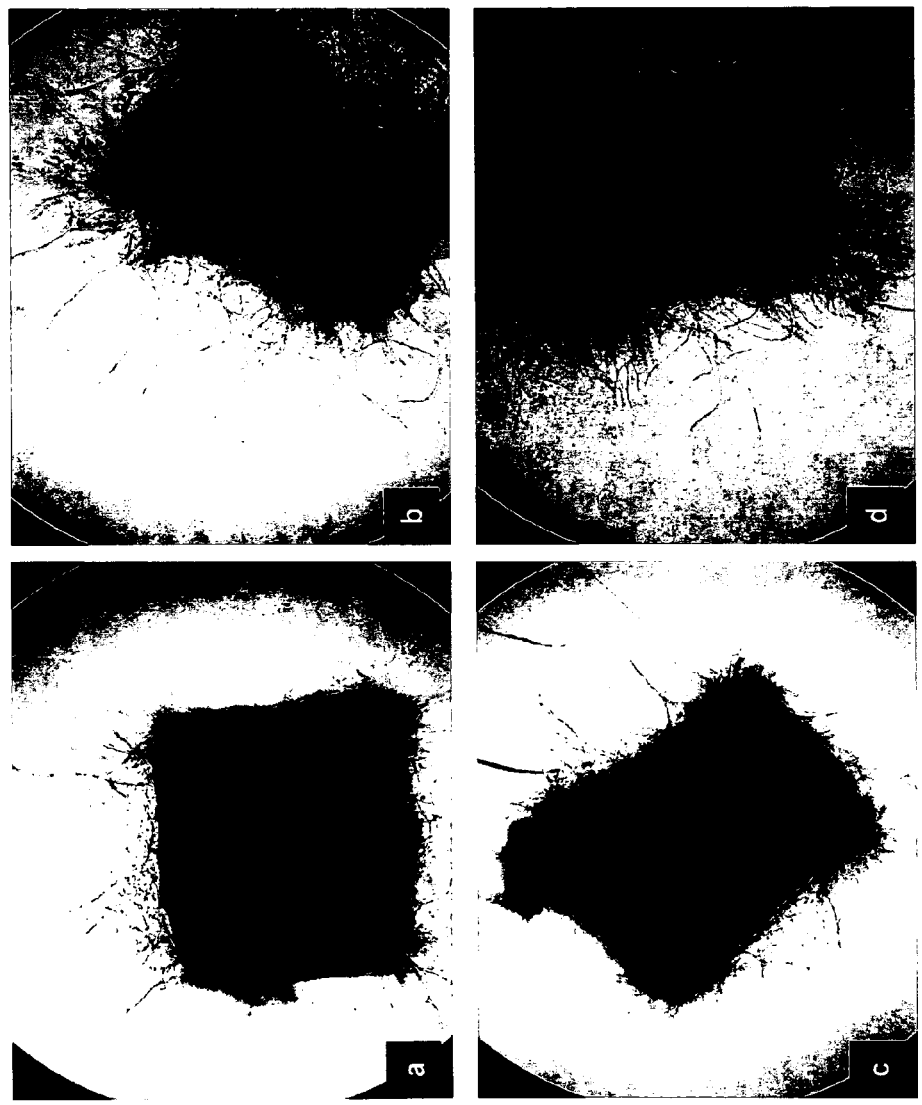
Figure 15:
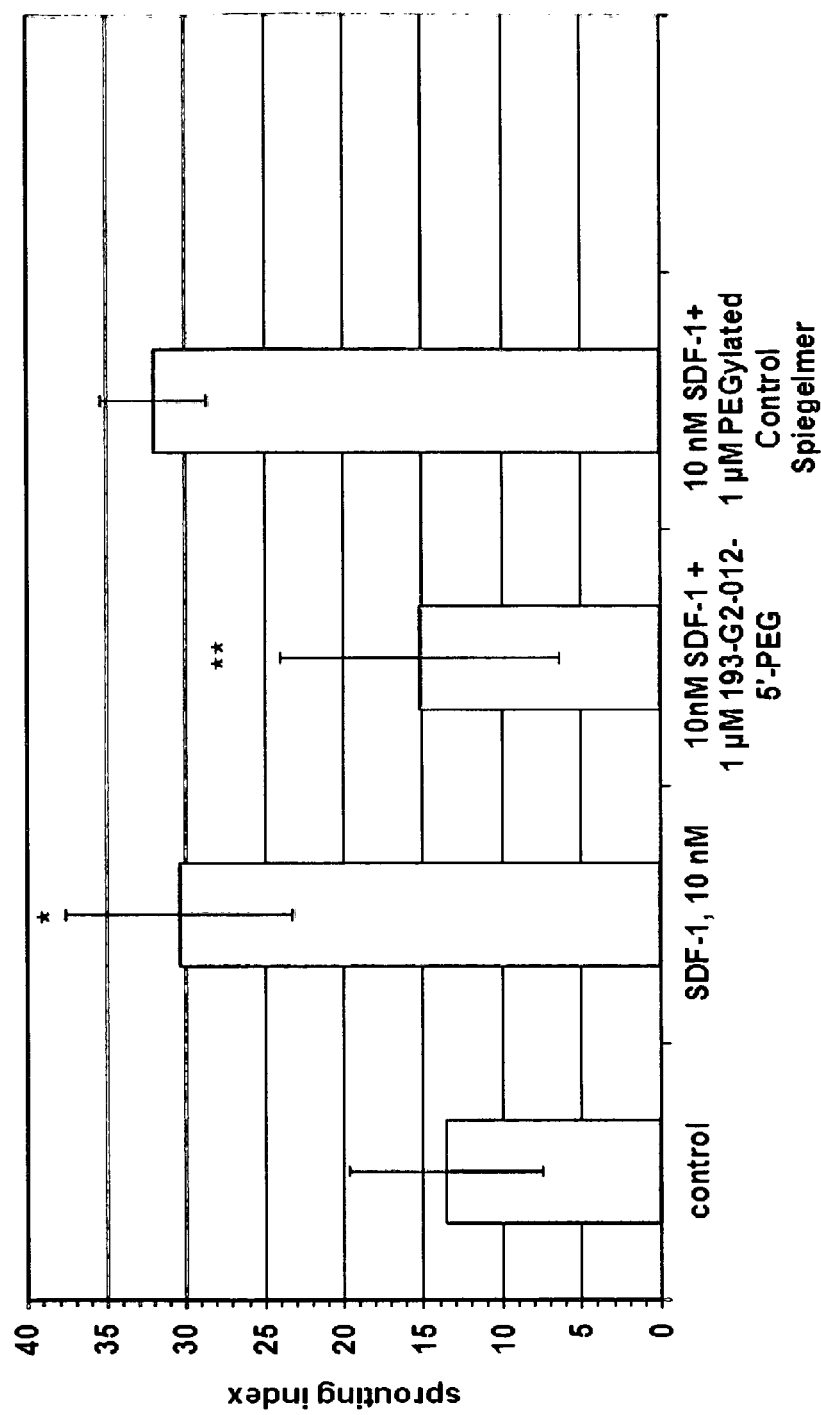

FIGS. 7A+B show derivatives of SDF-1 binding nucleic acid molecules 190-D5-001 (SDF-1 binding nucleic acid molecules of "type C");

FIG. 8 shows derivatives of SDF-1 binding nucleic acid molecule 197-B2 (SDF-1 binding nucleic acid molecule of "type C");

FIG. 9 shows further SDF-1 binding nucleic acid molecules which are, in addition to other SDF-1 binding nucleic acid molecules, also referred to as SDF-1 binding nucleic acid molecules of "type D";

FIG. 10 shows the efficacy of SDF-1 binding Spiegelmers 193-G2-012-5'-PEG (also referred to as NOX-A12), 197-B2-006-5'-PEG, 191-D5-007-5'-PEG and 191-A10-008-5'-PEG in a chemotaxis assay with the human T cell leukemia cell line Jurkat whereby cells were allowed to migrate towards 0.3 nM human SDF-1 preincubated at 37° C. with various amounts of Spiegelmers 193-G2-012-5'-PEG, 197-B2-006-5'-PEG, 191-D5-007-5'-PEG and 191-A10-008-5'-PEG, represented as percentage of control over concentration of Spiegelmers 193-G2-012-5'-PEG, 197-B2-006-5'-PEG, 191-D5-007-5'-PEG and 191-A10-008-5'-PEG;

FIG. 11A shows the efficacy of SDF-1 binding Spiegelmer NOX-A12 in a chemotaxis assay with the human pre-B ALL cell line Nalm-6 whereby cells were allowed to migrate towards 0.3 nM human SDF-1 preincubated at 37° C. with various amounts of Spiegelmer NOX-A12 represented as percentage of control over concentration of Spiegelmer NOX-A12;

FIG. 11B shows the efficacy of SDF-1 binding Spiegelmer NOX-A12 in a chemotaxis assay with the human leukemic monocyte lymphoma cell line U937 whereby cells were allowed to migrate towards 3 nM human SDF-1 preincubated at 37° C. with various amounts of Spiegelmer NOX-A12 represented as percentage of control over concentration of Spiegelmer NOX-A12;

FIG. 12 shows the efficacy of SDF-1 binding Spiegelmer NOX-A12 in a chemotaxis assay with the human pre-B cell leukemia cell line BV-173 whereby cells were allowed to migrate towards 3 nM human SDF-1 preincubated at 37° C. with various amounts of Spiegelmer NOX-A12 represented as percentage of control over concentration of Spiegelmer NOX-A12;

FIG. 13 shows the efficacy of SDF-1 binding Spiegelmer NOX-A12 in a complementation assay with CHO cells stably expressing CXCR7 and β-arrestin both fused to a fragment of β-galactosidase whereby CXCR7 of the cells were activated towards 10 nM human SDF-1 preincubated at 37° C. with various amounts of Spiegelmer NOX-A12 represented as percentage of control over concentration of Spiegelmer NOX-A12;

FIG. 14 shows the inhibition of SDF-1 induced sprouting by human SDF-1 binding Spiegelmer 193-G2-012-5'-PEG (also referred to as NOX-A12) and by PEGylated Control Spiegelmer in aortic ring sprouting assay, whereby rings from rat aorta were embedded in collagen matrix and incubated for 6 days with SDF-1 with or without Spiegelmers (a: control; b: 10 nM SDF-1; c: 10 nM SDF-1+1 µM human SDF-1 binding Spiegelmer 193-G2-012-5'-PEG; d: 10 nM SDF-1+1 M PEGylated Control Spiegelmer);

FIG. 15 shows the inhibition of SDF-1 induced sprouting by human SDF-1 binding Spiegelmer 193-G2-02-5'-PEG (also referred to as NOX-A12) and by PEGylated Control Spiegelmer in aortic ring sprouting assay whereby sprouting indices are shown as mean+/−SD for 5 rings per condition (*: the value for SDF-1 is significantly different from control (Mann-Whitney-test; p=0.009); **: the value for SDF-1+ human SDF-1 binding Spiegelmer 193-G2-012-5'-PEG is significantly different from that for SDF-1 (Mann-Whitney-test; p 0.028)

Figure 16:
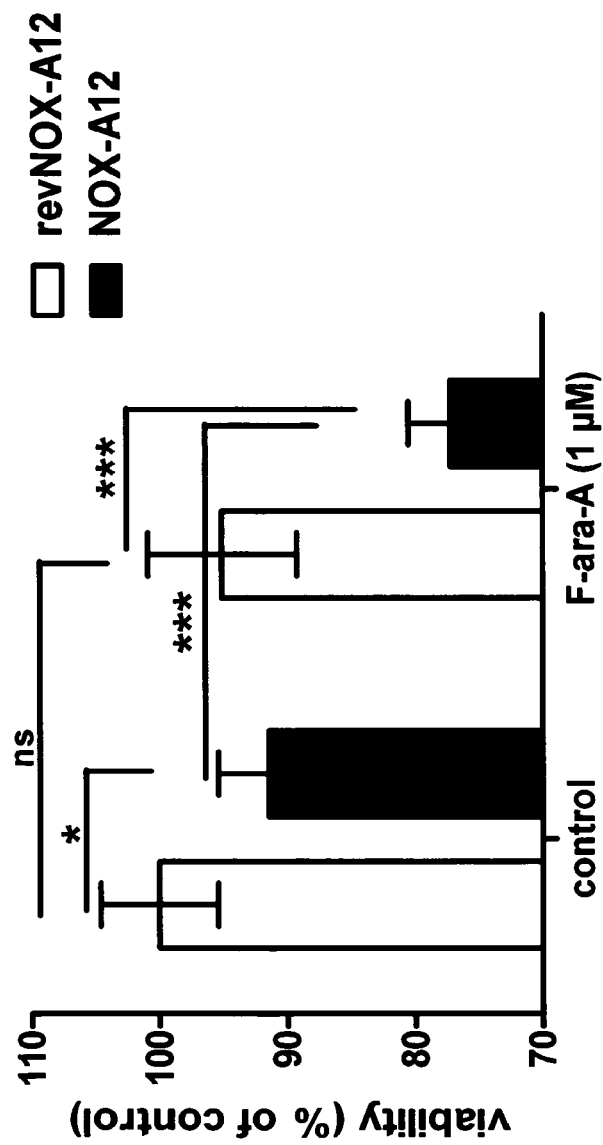
Figure 17:
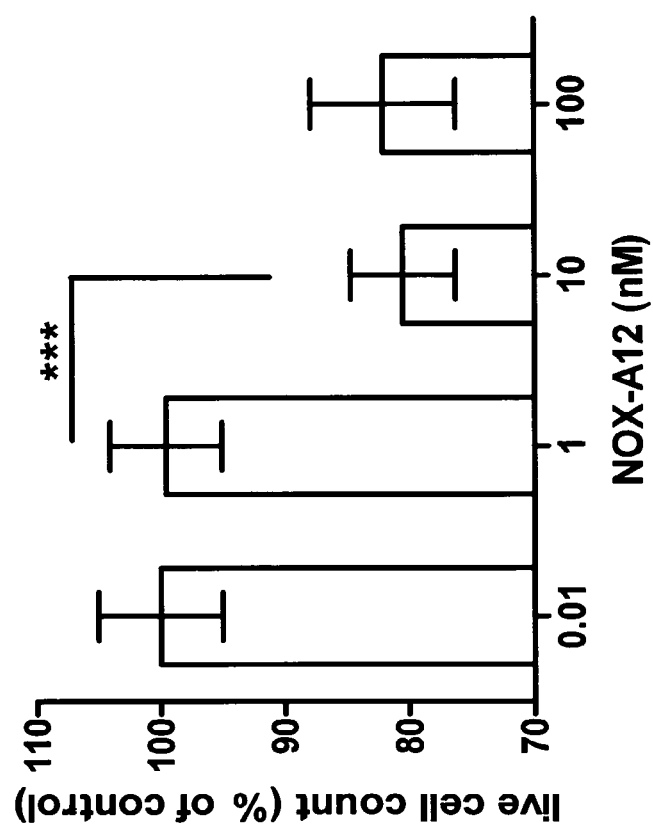

FIG. 16 shows the efficacy of human SDF-1 binding Spiegelmer NOX-A12 to sensitize RPMI-8226 MM cells to F-ara-A (Fludarabine), whereby confluent murine BM stromal MS-5 cells secreting SDF-1 were incubated with human SDF-1 binding Spiegelmer NOX-A12 or the non-functional revNOX-A12 and subsequently cocultured with RPMI-8226 MM cells; cells were treated with 1 µM F-ara-A for 40 hours and cell viability was measured by Flow Cytometry using ViaCount Reagent; Error bars indicate SD, N=5, *p=0.0134, ***p=0.0003 (two-tailed, unpaired t-test);

FIG. 17 shows the efficacy of human SDF-1 binding Spiegelmer NOX-A12 to inhibit the proliferation of Jurkat cells in coculture with stromal MS-5 cells, whereby murine stromal MS-5 cells secreting SDF-1 were incubated with increasing concentrations of human SDF-1 binding Spiegelmer NOX-A12; Jurkat cells were added to the confluent MS-5 cell layer and cell counts were measured after 40 hours by Flow Cytometry using ViaCount Reagent. Error bars indicate SD, N=4, ***p=0.0008 (two-tailed, unpaired t-test);

FIG. 18A+B show the efficacy of human SDF-1 binding Spiegelmer NOX-A12 to reverse SDF-1 dose-dependent adhesion of Jurkat cells to fibronectin, whereby Jurkat cells were incubated with SDF-1 alone (A), with SDF-1 and increasing concentrations of human SDF-1 binding Spiegelmer NOX-A12 or with SDF-1 and increasing concentrations of control Spiegelmer revNOX-A12 (B) for 30 minutes and seeded on fibronectin coated plates for 15 minutes; cells were subsequently washed off with media and attached cells were quantified using Cell Titer Glo Reagent; error bars indicate SD.

EXAMPLE 1: NUCLEIC ACIDS THAT BIND HUMAN SDF-1

In the following the terms 'nucleic acid' and 'nucleic acid molecule' are used herein in a synonymous manner if not indicated to the contrary. Moreover, the terms 'stretch' and 'stretch of nucleotide' are used herein in a synonymous manner if not indicated to the contrary.

L-nucleic acid molecules that bind to human SDF-1 and the respective nucleotide sequences are depicted in FIGS. 1 to 9. The nucleic acids were characterized on the aptamer, i.e. D-nucleic acid level using competitive or direct pull-down binding assays with biotinylated human D-SDF-1 (protocol, see Example 3). Spiegelmers were tested with the natural configuration of SDF-1 (L-SDF-1) by surface plasmon resonance measurement using a Biacore 2000 instrument (protocol, see Example 5) and a cell culture in vitro chemotaxis assay (protocol, see Example 4).

The SDF-1 binding nucleic acid molecules exhibit different sequence motifs, three main types are defined in FIGS. 1, 2A and 2B (Type A), FIGS. 3, 4A and 4B (Type B), FIGS. 5, 4, 7A, 7B and 8 (Type C). The nucleic acid molecules exhibit different sequence motifs. For definition of nucleotide sequence motifs, the IUPAC abbreviations for ambiguous nucleotides is used:

| | | |
|---|---|---|
| S | strong | G or C; |
| W | weak | A or U; |
| R | purine | G or A; |
| Y | pyrimidine | C or U; |
| K | keto | G or U; |
| M | imino | A or C; |
| B | not A | C or U or G; |
| D | not C | A or G or U; |
| H | not G | A or C or U; |
| V | not U | A or C or G; |
| N | all | A or G or C or U |

If not indicated to the contrary, any nucleic acid sequence or sequence of stretches and boxes, respectively, is indicated in the 5'→3' direction.

SDF-1 Binding Nucleic Acid Molecules of Type A

As depicted in FIG. 1 all sequences of SDF-1 binding nucleic acid molecules of type A comprise one central stretch of nucleotides which is flanked by the first (5'-) terminal and the second (3'-) terminal stretch of nucleotides (also referred to as first terminal stretch of nucleotides and second stretch of nucleotides) whereby both stretches can hybridize to each other. However, such hybridization is not necessarily given in the molecule.

In the following the terms 'SDF-1 binding nucleic acid molecules of type A' and 'Type A SDF-1 binding nucleic acids' or Type A SDF-1 binding nucleic acid molecules' are used herein in a synonymous manner if not indicated to the contrary.

The sequences of the defined boxes or stretches of nucleotides may be different between the SDF-1 binding nucleic acids of type A which influences the binding affinity to SDF-1. Based on binding analysis of the different SDF-1 binding nucleic acids summarized as Type A SDF-1 binding nucleic acids, the central stretch of nucleotides and its nucleotide sequences as described in the following are individually and more preferably in their entirety essential for binding to SDF-1.

The central stretch of nucleotides of all identified sequences of Type A SDF-1 binding nucleic acids share the sequence (Type A Formula-1, SEQ ID NO: 74),

AAAGYRACAHGUMAAX$_A$UGAAAGGUARC whereby $X_A$ is either absent or is 'A'. If 'A' is absent, the sequence of the central nucleotide sequence can be summarized as Type A Formula-2

SEQ ID NO: 75.

(AAAGYRACAHGUMAA-UGAAAGGUARC),

Type A SDF-1 binding nucleic acid 191-A6 (central nucleotide sequence:

SEQ ID NO: 54)

AAAGUAACACGUAAAAUGAAAGGAAC, carrying the additional nucleotide 'A' within the central nucleotide sequence and still binding to SDF-1 let conclude an alternative central nucleotide sequence Type A Formula-3, SEQ ID NO: 76).

AAAGYRACAHGUMAAAUGAAAGGUARC,

Exemplarily for all the other nucleic acids of Type A SDF-1 binding nucleic acids, the Type A SDF-1 binding nucleic acid 192-A10-001 was characterized for its binding affinity to human SDF-1. The equilibrium binding constant $K_D$ was determined using the pull-down binding assay ($K_D$=1.5 nM) and by surface plasmon resonance measurement ($K_D$=1.0 nM). The IC$_{50}$ (inhibitory concentration 50%) of 0.12 nM for 192-A10-001 was measured using a cell culture in vitro chemotaxis assay. Consequently, all Type A SDF-1 binding nucleic acids as depicted in FIG. 1 were analyzed in a competitive pull-down binding assay vs. 192-A10-001. The Type A SDF-1 binding nucleic acids 192-B11 and 192-C10 showed equal binding affinities as 192-A10-001 in these competition experiments. Weaker binding affinity was determined for Type A SDF-1 binding nucleic acids 192-G10, 192-F10, 192-C9, 192-E10, 192-D11, 192-G11, 192-H11 and 191-A6. The Type A SDF-1 binding nucleic acids 192-D10, 192-E9 and 192-H9 have much weaker binding affinity than 192-A10-001.

As mentioned above, the Type A SDF-1 binding nucleic acid 192-B11 and 192-C10 exhibit equal binding affinity to SDF-1 as 192-A10-001. However, they show slight differences in the nucleotide sequence of the central stretch of nucleotides. Therefore the consensus sequence of the three molecules binding to SDF-1 with almost the same high affinity can be summarized by the nucleotide sequence (Type A Formula-4, SEQ ID NO:77))

AAAGYAACAHGUCAAUGAAAGGUARC whereby the nucleotide sequence of the central stretch of nucleotides of 192-A10-001 (nucleotide sequence:

SEQ ID NO: 84

AAAGCAACAUGUCAAUGAAAGGUAGC, represents nucleotide sequence with the best binding affinity of Type A SDF-1 binding nucleic acids.

Five or six out of the six nucleotides of the 5'-terminal stretch (also referred to as first terminal stretch) of Type A SDF-1 binding nucleic acids may hybridize to the respective five or six nucleotides out of the six nucleotides of the 3'-terminal stretch (also referred to as second terminal stretch) to form a terminal helix. Although these nucleotides are variable at several positions, the different nucleotides allow for hybridization of five or six out of the six nucleotides of the 5'- and 3'-terminal stretches each. The 5'-terminal and 3'-terminal stretches of Type A SDF-1 binding nucleic acids as shown in FIG. 1 can be summarized in a generic formula for the 5'-terminal stretch ('RSHRYR', Type A Formula-5-5') and for the 3'-terminal stretch ('YRYDSY', Type A Formula-5-3'). Truncated derivatives of Type A SDF-1 binding nucleic acid 192-A10-001 were analyzed in a competitive pull-down binding assay vs. the original molecule 192-A10-001 and 192-A10-008 (FIGS. 2A and 2B). These experiments showed that a reduction of the six terminal nucleotides (5'end: GCUGUG; 3'end: CGCAGC) of 192-A10-001 to five nucleotides (5'end: CUGUG; 3'end: CGCAG) of the derivative 192-A10-002 could be done without reduction of binding affinity. However, the truncation to four terminal nucleotides (5'end: UGUG; 3'end: CGCA; 192-A10-003) or less (192-A10-004/-005/-006/-007) led to reduced binding affinity to SDF-1 (FIG. 2A). The determined 5'-terminal and 3'-terminal stretches with a length of five and four nucleotides of the derivatives of Type A SDF-1 binding nucleic acid 192-A10-001 as shown in FIGS. 2A and 2B can be described in a generic formula for the 5'-terminal stretch ('X₂BBBS', Type A Formula-6-5') and of the 3'-terminal stretch ('SBBVX₃'; Type A Formula-6-3'), whereby X₂ is either absent or is 'S' and X₃ is either absent or is 'S'.

The nucleotide sequence of the 5'- and 3'-terminal stretches has an influence on the binding affinity of Type A SDF-1 binding nucleic acids. This is not only shown by the nucleic acids 192-F10 and 192-E10, but also by derivatives of 192-A10-001 (FIG. 2B). The central stretch of 192-F10 and 192-E10 are identical to 192-B11 and 192-C10, but comprise slight differences at the 3'-end of 5'-terminal stretch and at the 5'-end of V-terminal stretch resulting in reduced binding affinity.

The substitution of 5'- and 3'-terminal nucleotides 'CUGUG' and 'CGCAG' of Type A SDF-1 binding nucleic acid 192-A10-002 by 'GCGCG' and 'CGCGC' (192-A10-015) resulted in a reduced binding affinity whereas substitutions by 'GCGUG' and 'CGCGC' (192-A10-008) resulted in same binding affinity as shown for 192-A100-002 (FIG. 2B). Additionally, nine derivatives of Type A SDF-1 binding nucleic acid 192-A10-001 (192-A10-014/-015/-016/-017/-018/-019/-020/-021/-022/-023) bearing four 5'- and 3'-terminal nucleotides respectively were tested as aptamers for their binding affinity vs. 192-A10-001 or its derivative 192-A10-008 (both have the identical binding affinity to SDF-1). All molecules showed weaker, much weaker or very much weaker binding affinity to SDF-1 as 192-A10-001 (six nucleotides forming a terminal helix) or as 192-A10-008 with five terminal nucleotides, respectively (FIG. 2B). Consequently, the sequence and the number of nucleotides of the 5'- and 3'-terminal stretches are essential for an effective binding to SDF-1. As shown for Type A SDF-1 binding nucleic acids 192-A10-002 and 192-A10-08 the preferred combination of 5'- and 3'-terminal stretches are 'CUGUG' and 'CGCAG' (5'- and 3'-terminal stretches of Type A SDF-1 binding nucleic acid 192-A10-002) and 'GCGUG' and 'CGCGC' (5'- and 3'-terminal stretches of Type A SDF-1 binding nucleic acid 192-A10-008).

However, combining the 5'- and 3'-terminal stretches of all tested Type A SDF-1 binding nucleic acids the generic formula for the 5'-terminal stretch of Type A SDF-1 binding nucleic acids is 'X₁X₂NNBV' (Type A Formula-7-5') and the generic formula for the 3'-terminal stretch of Type A SDF-1 binding nucleic acids is 'BNBNX₃X₄' (Type A Formula-7-3'), whereas X₁ is 'R' or absent, X₂ is 'S', X₃ is 'S' and X₄ is 'Y' or absent;

or

X₁ is absent, X₂ is 'S' or absent, X₃ is 'S' or absent and X₄ is absent.

In order to prolong the Spiegelmer's plasma residence time in vivo, Spiegelmers 192-A10-008 was covalently coupled to a 40 kDa polyethylene glycol (PEG) moiety at the 5'-end as described in chapter 2. The PEG-moiety has no influence on Spiegelmers potency to inhibit SDF-1 induced chemotaxis.

SDF-1 Binding Nucleic Acid Molecules of Type B

As depicted in FIG. 3 all sequences of SDF-1 binding nucleic acids of type B comprise one central stretch of nucleotides which is flanked by 5'- and 3'-terminal stretches (also referred to as first and second terminal stretch of nucleotides) that can hybridize to each other. However, such hybridization is not necessarily given in the molecule.

In the following the terms 'SDF-1 binding nucleic acid molecules of type B' and 'Type B SDF-1 binding nucleic acids' or Type B SDF-1 binding nucleic acid molecules' are used herein in a synonymous manner if not indicated to the contrary.

The sequences of the defined boxes or stretches may be different between the SDF-1 binding nucleic acids which influences the binding affinity to SDF-1. Based on binding analysis of the different SDF-1 binding nucleic acids, the central stretch of nucleotides and its nucleotide sequences as described in the following are individually and more preferably in their entirety essential for binding to SDF-1.

The central stretch of nucleotides of all identified sequences of SDF-1 binding nucleic acids 193-C2-001, 193-G2-001, 193-F2-001, 193-G1-002, 193-D2-002, 193-A1-002, 193-D3-002, 193-B3-002, 193-H3-002, 193-E3-002 and 193-D1-002 share the sequence (Type B Formula-1, SEQ ID NO: 52)

GUGUGAUCUAGAUGUADWGGCUGWUCCUAGUYAGG

The SDF-1 binding nucleic acids 193-G2-001, 193-C2-001 and 193-F2-001 that differ in one position of the central stretch of nucleotides (consensus sequence of central stretch of nucleotides:

(Type B Formula-2, SEQ ID NO: 53)

GUGUGAUCUAGAUGUADUGGCUGAUCCUAGUCAGG were analyzed in a competitive pull-down binding assay vs. the SDF-1 binding nucleic acid 192-A10-001 ($K_D$ of 1.5 nM determined in a pull-down binding assay, $IC_{50}$ of 0.12 nM). Each of the SDF-1 binding nucleic acids 193-G2-001, 193-C2-001 and 193-F2 showed superior binding to human SDF-1 in comparison to SDF-1 binding nucleic acid 192-A10-001 whereby the binding affinity of 193-G2-001 is as good as 193-C2-001 and 193-F2-001 (FIG. 3). The data suggests that the difference in the nucleotide sequence of the central stretch of nucleotides of SDF-1 binding nucleic acids 193-G2-001, 193-C2-001 and 193-F2-001 has no influence on the binding affinity to SDF-1. The SDF-1 binding nucleic acids 193-G1-002, 193-D2-002, 193-A1-002, 193-D3-002, 193-B3-002, 193-H3-002, 193-E3-002 and 193-D1-002 showed reduced binding to human SDF-1 in comparison to SDF-1 binding nucleic acid 193-G2-001. SDF-1 binding nucleic acid 193-G2-001 was characterized for its binding affinity to human SDF-1. The equilibrium binding constant $K_D$ was determined using the pull-down binding assay ($K_D$=0.3 nM). The $IC_{50}$ (inhibitory concentration 50%) of 0.08 nM for 193-G2-001 was measured using a cell culture in vitro chemotaxis assay.

Four, five or six nucleotides out of the six nucleotides of the 5'-terminal stretch of SDF-1 binding nucleic acids may hybridize to the respective four, five or six out of the six nucleotides of the 3'-terminal stretch of SDF-1 binding nucleic acids to form a terminal helix.

Although the nucleotides are variable at several positions, the different nucleotides allow the hybridization for four, five or six nucleotides out of the six nucleotides of the 5'- and 3'-terminal stretches each. The 5'-terminal and 3'-terminal stretches of SDF-1 binding nucleic acids as shown in FIG. 3 can be summarized in a generic formula for the 5'-terminal stretch ('$X_1X_2$GCRWG' whereby $X_1$ is 'A' or absent, $X_2$ is 'G') and of the 3'-terminal stretch ('KRYSC$X_3X_4$' whereby $X_3$ is 'G', $X_4$ is 'U' or absent). SDF-1 binding nucleic acids 193-G01-002, 193-D2-002, 193-A1-002 and 193-D3-002 have weaker binding affinities to SDF-1 although they share the identical central stretch of nucleotides with 193-C2-001, 193-G2-001 and 193-F2-001 (FIG. 3). The unfavorable binding properties of SDF-1 binding nucleic acids 193-G1-002, 193-D2-002, 193-A1-002 and 193-D3-002 may be due to the number of nucleotides and sequence of the 5'- and 3'-terminal stretches.

Truncated derivatives of the SDF-1 binding nucleic acids 193-G2-001 and 193-C2-001 were analyzed in a competitive pull-down binding assay vs. 193-G2-001 and 193-G2-012, respectively (FIGS. 4A and 4B). These experiments showed that a reduction of the six terminal nucleotides (5'end: AGCGUG; 3'end: UACGCU) of SDF-1 binding nucleic acids 193-G2-001 and 193-C2-001 to five nucleotides (5'end: GCGUG; 3'end: UACGC) lead to molecules with similar binding affinity (193-C2-002 and 193-G2-012). The equilibrium dissociation constant $K_D$ was determined using the pull-down binding assay ($K_D$=0.3 nM). A truncation to four (5'end: CGUG; 3'end: UACG; 193-C2-003) or less nucleotides (193-C2-004, 193-C2-005, 193-C2-006, 193-C2-007) resulted in a reduced binding affinity to SDF-1 which was measured by using the competition pull-down binding assay (FIG. 4A). The nucleotide sequence of the five terminal nucleotides at the 5'- and 3'-end, respectively, has an influence on the binding affinity of SDF-1 binding nucleic acids. The substitution of 5'- and 3'-terminal nucleotides 'GCGUG' and 'UACGC' (193-C2-002, 193-G2-12) by 'GCGCG' and 'CGCGC' (193-G2-013) resulted in a reduced binding affinity. Additionally, the four different derivatives of SDF-1 binding nucleic acid 193-G2-001 with a terminal helix with a length of four base-pairing nucleotides (193-G2-014/-015/-016/-017) were tested. All of them showed reduced binding affinity to SDF-1 (FIG. 4B). Therefore the sequence and the length of the 5'- and 3'-terminal nucleotides are essential for an effective binding to SDF-1. The 5'-terminal and 3'-terminal stretches with a length of five and four nucleotides of the derivatives of SDF-1 binding nucleic acids 193-C2-003 and 193-G2-012 as shown in FIGS. 4A and 4B can be described in a generic formula for the 5'-terminal stretch ('$X_1X_2$SSBS'), whereby $X_1$ is absent, $X_2$ is either absent or is 'G', and of the 3'-terminal stretch ('BVSS$X_3X_4$'), and whereby $X_3$ is either absent or is 'C' and $X_4$ is absent. As shown for SDF-1 binding nucleic acids 193-G2-001 and 193-C2-01 and their derivatives 193-G2-012 and 193-C2-002 the preferred combination of 5'- and 3'-terminal stretches are '$X_1X_2$GCGUG' (5'-terminal stretch) and 'UACGC$X_3X_4$' (3'-terminal stretch), whereas $X_1$ is either 'A' or absent, $X_2$ is 'G' and $X_3$ is 'C' and '$X_4$ is 'U' or absent.

However, combining the 5'- and 3'-terminal stretches of all tested SDF-1 binding nucleic acids the generic formula for the 5'-terminal stretch of SDF-1 binding nucleic acids is '$X_1X_2$SVNS' and the generic formula for the 3'-terminal stretch SDF-1 binding nucleic acids is 'BVBS$X_3X_4$', whereas $X_1$ is 'A' or absent, $X_2$ is 'G', $X_3$ is 'C' and $X_4$ is 'U' or absent;

or $X_1$ is absent, $X_2$ is 'G' or absent, $X_3$ is 'C' or absent and $X_4$ is absent.

In order to prolong the Spiegelmer's plasma residence time in viva, Spiegelmers 193-G2-012 was covalently coupled to a 40 kDa polyethylene glycol (PEG) moiety at the 5'-end as described in chapter 2 (PEGylated-nucleic acid molecule: 193-G2-012-5'-PEG also referred to as NOX-A12). The PEGylated Spiegelmer NOX-A12 was analyzed in cell culture in an in vitro chemotaxis-assay and an inhibition of SDF-1 induced chemotaxis was determined ($IC_{50}$ of 0.2 nM). The PEGylated Spiegelmer NOX-A12 was analyzed by Biacore measurement and a binding constant ($K_D$) of 0.2 nM was determined.

SDF-1 Binding Nucleic Acid Molecules of Type C

As depicted in FIG. 12 all sequences of SDF-1 binding nucleic acids of type C comprise one central stretch of nucleotides which is flanked by 5'- and 3'-terminal stretches (also referred to as first terminal stretch and second terminal stretch of nucleotides) that can hybridize to each other. However, such hybridization is not necessarily given in the molecule.

In the following the terms 'SDF-1 binding nucleic acid molecules of type C' and 'Type C SDF-1 binding nucleic acids' or Type C SDF-1 binding nucleic acid molecules' are used herein in a synonymous manner if not indicated to the contrary.

The sequences of the defined boxes or stretches may be different between the SDF-1 binding nucleic acids of Type C which influences the binding affinity to SDF-1. Based on binding analysis of the different SDF-1 binding nucleic acids summarized as Type C SDF-1 binding nucleic acids, the central stretch of nucleotides and its nucleotide sequence as described in the following are individually and more preferably in their entirety essential for binding to SDF-1.

The central stretch of nucleotides of all identified sequences of Type C SDF-1 binding nucleic acids share the sequence (Type C Formula-1, SEQ ID NO: 108)

GGUYAGGGCUHRX$_4$AGUCGG whereby $X_A$ is either absent or is 'A'. With the exception of Type C SDF-1 binding nucleic acid 197-D1 the central stretch of nucleotides of all identified sequences of Type C SDF-1 binding nucleic acids share the nucleotide sequence (Type C Formula-2, SEQ ID NO: 109).

GGUYAGGGCUHRAAGUCGG

Type C SDF-L binding nucleic acid 197-D1 (central stretch of nucleotides:

(SEQ ID NO: 56)

GGUUAGGGCUAA-AGUCGG missing one nucleotide 'A' within the central stretch of nucleotides and still binding to SDF-1 let conclude an alternative central stretch of nucleotides Type C Formula-3, SEQ ID NO: 110).

( GGUYAGGGCUHR-AGUCGG ),

Initially, all Type C SDF-1 binding nucleic acids as depicted in FIG. 5 were analyzed in a competitive pull-down binding assay vs. Type A SDF-1 binding nucleic acid 192-A10-001 ($K_D$=1.5 nM determined by pull-down assay and by surface plasmon resonance measurements; IC$_{50}$=0.12 nM). The Type C SDF-1 binding nucleic acids 191-D5-001, 197-B2, 190-A3-001, 197-H1, 197-H3 and 197-E3 showed weaker binding affinities than 192-A10-001 in competition experiments. Much weaker binding affinity was determined for 191-A5, 197-B1, 197-D1, 197-H2 and 197-D2 (FIG. 5). The molecules or derivatives thereof were further characterized by further competitive pull-down binding assays, plasmon resonance measurements and an in vitro chemotaxis assay. The Type C SDF-1 binding nucleic acid 191-D5-001 was characterized for its binding affinity to human SDF-1 whereas the equilibrium binding constant $K_D$ was determined by surface plasmon resonance measurement ($K_D$=0.8 nM). The IC$_{50}$ (inhibitory concentration 50%) of 0.2 nM for 191-D5-001 was measured using a cell-culture in vitro chemotaxis assay. The binding affinity of Type C SDF-1 binding nucleic acid 197-B2 for human SDF-1 was determined by surface plasmon resonance measurement ($K_D$=0.9 nM), its IC$_{50}$ (inhibitory concentration 50%) of 0.2 nM was analyzed in a cell-culture in vitro chemotaxis assay. These data indicates that Type C SDF-1 binding nucleic acids 191-D5-001 and 197-B2 have the similar binding affinity to SDF-1 (FIGS. 5 and 8).

Type C SDF-1 binding nucleic acid 190-A3-001 comprises a 5'-terminal stretch of 17 nucleotides ('CGUGCGC-UUGAGAUAGG', SEQ ID NO: 220) and a 3'-terminal stretch of 12 nucleotides ('CUGAUUCUCACG', SEQ ID NO: 221) whereby on the one hand the four nucleotides at the 5'-end of the 5'-terminal stretch and the four nucleotides at the 3'-end of the 3'-terminal stretch may hybridize to each other to form a terminal helix. Alternatively the nucleotides 'UGAGA' in the 5'-terminal stretch may hybridize to the nucleotides 'UCUCA' in the 3'-terminal stretch to form a terminal helix. A reduction to nine nucleotides of the 5'-terminal stretch ('UGAGAUAGG') and to ten ('CUGAUU-CUCA', SEQ ID NO: 222) nucleotides of the 3'-terminal stretch ('CUGAUUCUC') of molecule 190-A3-001 does not have an influence on the binding affinity to SDF-1 (190-A3-003; FIG. 13). A reduction to eight nucleotides of the 5'-terminal stretch ('GAGAUAGG') and to nine nucleotides of the 3'-terminal stretch ('CUGAUUCUC') of molecule 190-A3-001 does not have an influence on the binding affinity to SDF-1 (190-A3-004; FIG. 6). The equilibrium binding constant $K_D$ of 190-A3-004 was determined using the pull-down binding assay ($K_D$=4.6 nM) and by surface plasmon resonance measurement ($K_D$=4.7 nM). The ICs, (inhibitory concentration 50%) of 0.1 nM for 190-A3-004 was measured using a cell-culture in vitro chemotaxis assay. However, the truncation to two nucleotides at the 5'-terminal stretch leads to a very strong reduction of binding affinity (190-A3-007; FIG. 6).

The Type C SDF-1 binding nucleic acids 191-D5-001, 197-B2 and 197-H1 (central stretch of nucleotides:

SEQ ID 57,

GGUUAGGGCUAGAAGUCGG ,

197-H3/191-A5 (central stretch of nucleotides.

SEQ ID NO: 58

GGUUAGGGCUCGAAGUCGG , and 197-E3/197-B1 (central stretch of nucleotides

SEQ ID NO: 59

GGUUAGGGCUUGAAGUCGG , share an almost identical central stretch of nucleotides (Type C formula-4; nucleotide sequence:

SEQ ID NO: 111).

GGUUAGGGCUHGAAGUCGG

191-D5-001, 197-B2 and 197-H1 do not share a similar 5'- and 3'-terminal stretch (197-H3 and 197-E3 have the identical 5'- and 3'-terminal stretch as 197-82). However, the respective ten (197-82, 197-E3, 197-13) or nine out of the ten (191-D5-001, 197-H1) nucleotides of the 5'-terminal stretch may hybridize to the respective ten (197-B2, 197-E3, 197-H3) or nine out of the ten (191-D5-001, 197-H1) nucleotides of the 3'-terminal stretch (FIG. 5). Thus, the 5'-terminal stretch of Type C SDF-1 binding nucleic acids 197-B2, 191-D5-001, 197-H1, 197-E3 and 197-H3 as mentioned above plus 191-A5, 197-B1, 197-H2, 197-D1 and 197-D2 comprise a common generic nucleotide sequence of 'RKSBUSNVGR' (Type C Formula-5-5', SEQ ID NO: 138). The 3'-terminal stretch of Type C SDF-1 binding nucleic acids 197-B2, 191-D5-001, 197-H1, 197-E3, and 197-H3 as mentioned above plus 191-A5, 197-B1, 197-H2, 197-D1 and 197-D2 comprise a common generic nucleotide sequence of 'YYNRCASSMY' (Type C Formula-5-3', SEQ ID NO: 139), whereby the 5' and the 3'-terminal stretches of Type C SDF-1 binding nucleic acids 197-B2, 191-D5-001, 197-H1, 197-E3 and 197-H3 are preferred. These preferred 5'- and 3'-terminal stretches of Type C SDF-1 binding nucleic acids 197-B2, 191-D5-001, 197-H1, 197-E3 and 197-H3 can be summarized in the generic formula 'RKSBUGSVGR' (Type C Formula-6-5'; 5'-terminal stretch, SEQ ID NO: 140) and 'YCNRCASSMY' (Type C Formula-6-3'; 3'-terminal stretch, SEQ ID NO: 141).

Truncated derivatives of Type C SDF-1 binding nucleic acid 191-D5-001 were constructed and tested in a competitive pull-down binding assay vs. the original molecule 191-D5-001 (FIG. 7A, FIG. 7B). At first the length of the 5'- and 3'-terminal stretches were shortened from ten nucleotides (191-D5-001) each to seven nucleotides each (191-D5-004) as depicted in FIG. 14A whereby nine out of the ten (191-D5-001) or six out of the seven nucleotides (191-D5-004) of the 5'-terminal stretch and of the 3'-terminal stretch, respectively can hybridize to each other. The reduction to seven nucleotides of the 5'- and 3'-terminal stretch respectively (whereas six out of the seven nucleotides can hybridize to each other) led to reduced binding affinity to SDF-1 (191-D5-004). The terminal stretches of Type C SDF-1 binding nucleic acid 191-D5-004 were modified whereby the non-pairing nucleotide 'A' within the 3'-terminal stretch of 191-D5-004 was substituted by a 'C' (191-D5-005). This modification led to an improvement of binding. This derivative, Type C SDF-1 binding nucleic acid 191-D5-005, showed similar binding to SDF-1 as 191-D5-001. Further truncation of the 5'- and 3'-terminal stretch to five nucleotides respectively led to a molecule with a length of total 29 nucleotides (191-D5-007). Because of the similarities of 191-D5-001 and of the Type C SDF-1 binding nucleic acids 197-B2, 191-D5-001, 197-H1, 191-A5, 197-H3, 197-81, 197-E3, 197-D1, 197-H2 and 197-D2 and because of the data shown for 191-D5-007 it may assume that the 5'- and 3'-terminal stretch can in principle be truncated down to five nucleotides whereby the nucleotide sequence 'CGGGA' for 5'-terminal stretch and 'UCCCG' for the 3'-terminal stretch was successfully tested (Type C SDF-1 binding nucleic acid 191-D5-007). Type C SDF-1 binding nucleic acid 191-D5-007 surprisingly binds somewhat better to SDF-1 than 191-D5-001 (determined on aptamer level using the competition binding assay). The equilibrium binding constant $K_D$ of 191-D5-007 was determined using the pull-down binding assay ($K_D$=2.2 nM) and by surface plasmon resonance measurement ($K_D$=0.8 nM). The $IC_{50}$ (inhibitory concentration 50%) of 0.1 nM for 191-D5-007 was measured using a cell-culture in vitro chemotaxis assay. Further truncation of both terminal stretches to four nucleotides (191-D5-010, FIG. 7A).

Further derivatives of Type C SDF-1 binding nucleic acid 191-D5-001 (191-D5-017/-024/-029) bearing 5'- and 3'-terminal stretches of respectively four nucleotides also showed reduced binding affinity to SDF-1 in the competition pull-down binding assay vs. 191-D5-007 (FIG. 7B). Alternative 5'- and 3'-terminal stretches with a length of respectively five nucleotides were additionally tested, too (191-D5-017-29a, 191-D5-017-29b, 191-D5-019-29a, 191-D5-024-29a, 191-D5-024-29b). The generic formula of these derivatives for the 5'-terminal stretch is '$X_S$SSSV' (Type C Formula-7-5') and for the 3'-stretch is 'BSSS$X_S$' Type C Formula-7-3'), whereby $X_S$ is absent or 'S'. Two out of the five tested variants showed identical binding affinity to SDF-1 as 191-D5-007 (191-D5-024-29a, 191-D5-024-29b; FIG. 7B). The sequences of the 5'-terminal and 3'-terminal stretches of 191-D5-001-derivatives that show the best binding affinity to SDF-1 and comprise a 5'-terminal and 3'-terminal stretch of five nucleotides respectively (191-D5-007, 191-D5-024-29a, 191-D5-024-29b) can be summarized in a generic formula (5'-terminal stretch: 'SGGSR', Type C Formula-8-5'; 3'-terminal stretch: 'YSCCS', Type C Formula-8-3').

Truncated derivatives of Type C SDF-1 binding nucleic acid 197-B2 were analyzed in a competitive pull-down binding assay vs. the original molecule 197-B2 and 191-D5-007 (FIG. 7). Using the competitive pull-down binding assay vs. 191-D5-007 it was shown that 197-B2 has the same binding affinity to SDF-1 as 191-D5-007. The 5'- and 3'-terminal stretches were shortened without loss of binding affinity from ten nucleotides (197-B2) each to five nucleotides each (197-B2-005) whereby the nucleotides of the 5'-terminal stretch and of the 3'-terminal stretch can completely hybridize to each other. If the 5'-terminal ('GCGGG') and 3'-terminal ('CCUGC') stretch of 197-B2-005 was substituted by 'GCCGG' (5'-terminal stretch) and by 'CCGGC' (3'-terminal stretch) of 197-B2-006, the binding affinity to SDF-1 fully persisted. Because 197-B2 and 191-D5-001 (and their derivatives) share the identical core nucleotide sequence and several derivatives of 191-D5 with 5'- and 3'-terminal stretches with a length of respectively four nucleotides were tested, a further truncation of the 5'- and 3'-terminal stretch was omitted. Two further derivatives were designed that comprise six nucleotides at the 5'- and 3'-end (5'- and 3'-terminal stretches) respectively. The binding affinity to SDF-1 of both molecules (197-B2-006-31a and 197-B2-006-31b) is the same as shown for 191-D5-007 and 197-B2-006 (FIG. 15). The sequences of the 5'-terminal and 3'-terminal stretches of 197-B2 derivatives that show the best binding affinity to SDF-1 and comprise a 5'-terminal and 3'-terminal stretch of five nucleotides respectively can be summarized in a generic formula (5'-terminal stretch: 'GCSGG', Type C Formula-9-5'; 3'-terminal stretch: 'CCKGC', Type C Formula-9-3').

Combining the preferred 5'- and 3'-stretches of truncated derivatives of Type C SDF-1 binding nucleic acids 191-D5-001 (5'-terminal stretch: 'SGGSR', Type C Formula-8-5'; 3'-terminal stretch: 'YSCCS', Type C Formula-8-3') and 197-B2 (5'-terminal stretch: 'GCSGG', Type C Formula-9-5'; 3'-terminal stretch: 'CCKGC'. Type C Formula-9-3') the common preferred generic formula for the 5'-terminal and the 3'-terminal stretch is 'SSSSR' (5'-terminal stretch, Type C Formula-10-5') and 'YSBSS' (3'-terminal stretch: Type C Formula-10-3').

In order to prolong the Spiegelmer's plasma residence time in vivo, Spiegelmers 197-B2-006 and 191-D5-007 were covalently coupled to a 40 kDa polyethylene glycol (PEG) moiety at their 5'-ends as described in chapter 2. The PEGylated Spiegelmers 197-B2-006 and 191-D5-007 were analyzed in cell culture in an in vitro chemotaxis. The PEG-moiety has no influence on Spiegelmers potency to inhibit SDF-1 induced chemotaxis.

SDF-1 Binding Nucleic Acid Molecules of Type D

Additionally, further three SDF-1 binding nucleic acids that do not share the SDF-1 binding motifs of 'Type A', 'Type B' and 'Type C' were identified and are referred to herein as "type D". There were analyzed as aptamers using the pull-down binding assay (FIG. 9).

It is to be understood that any of the sequences shown in FIGS. 1 through 9 are nucleic acid molecules according to the present invention, including those truncated forms thereof but also including those extended forms thereof under the proviso, however, that the thus truncated and extended, respectively, nucleic acid molecules are still capable of binding to the target.

EXAMPLE 2: SYNTHESIS AND DERIVATIZATION OF APTAMERS AND SPIEGELMERS

Small Scale Synthesis

Aptamers and Spiegelmers were produced by solid-phase synthesis with an ABI 394 synthesizer (Applied Biosystems, Foster City, Calif., USA) using 2'TBDMS RNA phosphoramidite chemistry (Damha and Ogilvie, 1993). rA(N-Bz)-, rC(Ac)-, rG(N-ibu)-, and rU-phosphoramidites in the D- and L-configuration were purchased from ChemGenes, Wilmington, Mass. Aptamers and Spiegelmers were purified by gel electrophoresis.

Large Scale Synthesis Plus Modification

The Spiegelmers were produced by solid-phase synthesis with an ÄktaPilot100 synthesizer (Amersham Biosciences; General Electric Healthcare, Freiburg) using 2'TBDMS RNA phosphoramidite chemistry (Damha and Ogilvie, 1993). L-rA(N-Bz)-, L-rC(Ac)-, L-rG(N-ibu)-, and L-rU-phosphoramidites were purchased from ChemGenes (Wilmington, Mass., USA). The 5'-amino-modifier was purchased from American International Chemicals Inc. (Framingham, Mass., USA). Synthesis of the Spiegelmers was started on L-riboG; L-riboC, L-riboA, L-riboU respectively modified CPG pore size 1000 Å (Link Technology, Glasgow, UK). For coupling (15 min per cycle), 0.3 M benzylthiotetrazole (American International Chemicals Inc., Framingham, Mass., USA) in acetonitrile, and 3.5 equivalents of the respective 0.2 M phosphoramidite solution in acetonitrile was used. An oxidation-capping cycle was used. Further standard solvents and reagents for oligonucleotide synthesis were purchased from Biosolve (Valkenswaard, NL). The Spiegelmers were synthesized DMT-ON; after deprotection, it was purified via preparative RP-HPLC (Wincott F. et al., 1995) using Source15RPC medium (Amersham). The 5'DMT-group was removed with 80% acetic acid (90 min at RT). Subsequently, aqueous 2 M NaOAc solution was added and the Spiegelmer was desalted by tangential-flow filtration using a 5 K regenerated cellulose membrane (Millipore, Bedford, Mass.).

PEGylation

In order to prolong the Spiegelmer's plasma residence time in vivo, the Spiegelmers were covalently coupled to a 40 kDa polyethylene glycol (PEG) moiety at the 5'-end.

For PEGylation (for technical details of the method for PEGylation see European patent application EP 1 306 382), the purified 5'-amino modified Spiegelmerd were dissolved in a mixture of $H_2O$ (2.5 ml), DMF (5 ml), and buffer A (5 ml; prepared by mixing citric acid.$H_2O$ [7 g], boric acid [3.54 g], phosphoric acid [2.26 ml], and 1 M NaOH [343 ml] and adding water to a final volume of 1 l; pH=8.4 was adjusted with 1 M HCl).

The pH of the Spiegelmer solution was brought to 8.4 with 1 M NaOH. Then, 40 kDa PEG-NHS ester (JenKem Technology USA Inc., Allen, Tex.) was added at 37° C. every 30 min in six portions of 0.25 equivalents until a maximal yield of 75 to 85% was reached. The pH of the reaction mixture was kept at 8-8.5 with 1 M NaOH during addition of the PEG-NHS ester.

The reaction mixture was blended with 4 ml urea solution (8 M), and 4 ml buffer B (0.1 M triethylammonium acetate in $H_2O$) and heated to 95° C. for 15 min. The PEGylated Spiegelmer was then purified by RP-HPLC with Source 15RPC medium (Amersham), using an acetonitrile gradient (buffer B; buffer C: 0.1 M triethylammonium acetate in acetonitrile). Excess PEG eluted at 5% buffer C, PEGylated Spiegelmer at 10-15% buffer C. Product fractions with a purity of >95% (as assessed by HPLC) were combined and mixed with 40 ml 3 M NaOAC. The PEGylated Spiegelmer was desalted by tangential-flow filtration (5 K regenerated cellulose membrane, Millipore, Bedford Mass.).

EXAMPLE 3: DETERMINATION OF BINDING CONSTANTS (PULL-DOWN BINDING ASSAY)

Direct Pull-Down Binding Assay

The affinity of aptamers to biotinlayted human D-SDF-1 was measured in a pull-down binding assay format at 37° C. Aptamers were 5'-phosphate labeled by T4 polynucleotide kinase (Invitrogen, Karlsruhe, Germany) using [$\gamma$-$^{32}$P]-labeled ATP (Hartmann Analytic, Braunschweig, Germany). The specific radioactivity of labeled aptamers was 200,000-800,000 cpm/pmol. Aptamers were incubated after de- and renaturation at 10, 20, 30 or 40 pM concentration at 37° C. in selection buffer (20 mM Tris-HCl pH 7.4; 137 mM NaCl; 5 mM KCl; 1 mM $MgCl_2$; 1 mM $CaCl_2$; 0.1% [w/vol] Tween-20) together with varying amounts of biotinlayted human D-SDF-1 for 4-12 hours in order to reach equilibrium at low concentrations. Selection buffer was supplemented with 10 µg/ml human serum albumin (Sigma-Aldrich, Steinheim, Germany), and 10 µg/ml yeast RNA (Ambion, Austin, USA) in order to prevent adsorption of binding partners with surfaces of used plasticware or the immobilization matrix. The concentration range of biotinlayted human D-SDF-1 was set from 8 pM to 100 nM; total reaction volume was 1 ml. Peptide and peptide-aptamer complexes were immobilized on 1.5 µl Streptavidin Ultralink Plus particles (Pierce Biotechnology, Rockford, USA) which had been preequilibrated with selection buffer and resuspended in a total volume of 6 µl. Particles were kept in suspension for 30 min at the respective temperature in a thermomixer. Immobilized radioactivity was quantitated in a scintillation counter after detaching the supernatant and appropriate washing. The percentage of binding was plotted against the concentration of biotinlayted human D-SDF-1 and dissociation constants were obtained by using software algorithms (GRAFIT; Erithacus Software; Surrey U.K.) assuming a 1:1 stoichiometry.

Competitive Pull-Down Binding Assay

In order to compare different D-SDF-1 binding aptamers, a competitive ranking assay was performed. For this purpose the most affine aptamer available was radioactively labeled (see above) and served as reference. After de- and renaturation it was incubated at 37° C. with biotinlayted human D-SDF-1 in 1 ml selection buffer at conditions that resulted in around 5-10% binding to the peptide after immobilization and washing on NeutrAvidin agarose or Streptavidin Ultralink Plus (both from Pierce) without competition. An excess of de- and renatured non-labeled D-RNA aptamer variants was added to different concentrations (e.g. 2, 10, and 50 nM) with the labeled reference aptamer to parallel binding reactions. The aptamers to be tested competed with the reference aptamer for target binding, thus decreasing the binding signal in dependence of their binding characteristics. The aptamer that was found most active in this assay could then serve as a new reference for comparative analysis of further aptamer variants.

EXAMPLE 4: BINDING ANALYSIS BY SURFACE PLASMON RESONANCE MEASUREMENT

The Biacore 2000 instrument (Biacore AB, Uppsala, Sweden) was used to analyze binding of Spiegelmers to human SDF-1α. When coupling of human SDF-1α was to be achieved via amine groups, human SDF-1α was dialyzed against water for 1-2 h (Millipore VSWP mixed cellulose esters; pore size, 0.025 µM) to remove interfering amines. CM4 sensor chips (Biacore AB, Uppsala, Sweden) were activated before protein coupling by a 35-µl injection of a 1:1 dilution of 0.4 M NHS and 0.1 M EDC at a flow of 5 µl/min. Human MCP-1 or human SDF-1α was then injected in concentrations of 0.1-1.5 µg/ml at a flow of 2 µl/min until the instrument's response was in the range of 1000-2000 RU (relative units). Unreacted NHS esters were deactivated by injection of 35 µl ethanolamine hydrochloride solution (pH 8.5) at a flow of 5 µl/min. The sensor chip was primed twice with binding buffer and equilibrated at 10 µl/min for 1-2 hours until the baseline appeared stable. For all proteins, kinetic parameters and dissociation constants were evaluated by a series of Spiegelmer injections at concentrations of 1000, 500, 250, 125, 62.5, 31.25, and 0 nM in selection buffer (Tris-HCl, 20 mM; NaCl, 137 mM; KCl, 5 mM; $CaCl_2$, 1 mM; $MgCl_2$, 1 mM; Tween20, 0.1% [w/v]; pH 7.4). In all experiments, the analysis was performed at 37° C. using the Kinject command defining an association time of 180 and a dissociation time of 360 seconds at a flow of 10 µl/min. Data analysis and calculation of dissociation constants ($K_D$) was done with the BIAevaluation 3.0 software (BIACORE AB, Uppsala, Sweden) using the Langmuir 1:1 stochiometric fitting algorithm.

EXAMPLE 5: ANALYSIS OF THE INHIBITION OF SDF-1-INDUCED CHEMOTAXIS BY SDF-1-BINDING SPIEGELMERS

The human T cell leukemia cell line Jurkat, the human leukemic monocyte lymphoma cell line U937, the human pre-B cell leukemia cell line BV-173 and human pre-B ALL cell line Nalm-6 express CXCR4. While Jurkat cells do not express CXCR7, the leukemia lines BV-173 and U-937 were tested positive for CXCR7 expression. All cells used were obtained from the DSMZ (Braunschweig). All cell lines were cultivated at 37° C. and 5% CO2 in RPMI 1640 medium with Glutamax (Invitrogen, Karlsruhe, Germany) which contains 10% fetal bovine serum, 100 units/ml penicillin and 100 µg/ml streptomycin (Invitrogen, Karlsruhe, Germany). One day before the experiment, cells were seeded in a new T175 flask with a density of $0.3 \times 10^6$/ml (Jurkat, U937, BV-173) or $0.75 \times 10^6$/ml (Nalm-6), respectively.

For the experiment, cells were centrifuged (5 min at 300 g), resuspended, counted and washed once with 15 ml HBH (Hanks balanced salt solution containing 1 mg/ml bovine serum albumin and 20 mM HEPES; Invitrogen, Karlsruhe, Germany). Then the cells were resuspended at $1.33 \times 10^7$/ml (Jurkat, U937, BV-173) or $2.67 \times 10^6$/ml (Nalm-6), respectively. Cells were then allowed to migrate through the porous membranes of the filter plates for three hours towards a solution containing SDF-1 and various amounts of Spiegelmer. The stimulation solutions (SDF-1+various concentrations of Spiegelmer) were made up as 10× solutions in a 0.2 ml low profile 96-tube plate. 212 µl HBH were pipetted into the lower compartments of the transport plate and 23.5 µl of the stimulation solutions were added. All conditions were made up as triplicates. After 20 to 30 min the filter plate was inserted into the plate containing the stimulation solutions and 75 µl of a cell suspension with $1.33 \times 10^6$/ml or $2.67 \times 10^6$/ml, respectively, were added to the wells of the filter plate ($1 \times 10^5$ or $2 \times 10^5$ cells/well). The cells were then allowed to migrate for 3 h at 37° C. For calibration, 0, 10 and 30 µl of the cell suspension was added to 235, 225 and 205 µl HBH, respectively, in wells of a separate 96-well plate. After 3 hours incubation, the insert plate was removed and 30 µl resazurin working solution (440 µM in PBS) were added to the lower wells and to the wells of the calibration plate. The plates were then incubated at 37° C. for 2.5 h. After incubation, 100 µl of each well were transferred to a black 96 well plate.

For evaluation, fluorescence values were corrected for background fluorescence (no cells in well). Then the difference between experimental conditions with and without SDF-1 was calculated. The value for the sample without Spiegelmer (SDF-1 only) was set 100% and the values for the samples with Spiegelmer were calculated as percent of this. For a dose-response curve the percent-values were plotted against Spiegelmer concentration and the $IC_{50}$-value (concentration of Spiegelmer at which 50% of the activity without Spiegelmer is present) was determined graphically from the resulting curve.

Results

Human SDF-1 was found to stimulate migration of Jurkat cells in a dose dependent manner, with half-maximal stimulation at about 0.3 nM.

Human SDF-1 was found to stimulate migration of cells of the human leukemic monocyte lymphoma cell line U937 in a dose dependent manner, with half-maximal stimulation at about 3 nM.

Human SDF-1 was found to stimulate migration of cells of the human pre-B cell leukemia cell line BV-173 in a dose dependent manner, with half-maximal stimulation at about 3 nM.

Human SDF-1 was found to stimulate migration of cells of the human pre-B ALL cell line Nalm-6 in a dose dependent manner, with half-maximal stimulation at about 0.3 nM.

When cells were allowed to migrate towards a solution containing human SDF-1 plus increasing concentrations of SDF-1 binding Spiegelmers, dose-dependent inhibition was observed. The respective IC50s of the tested Spiegelmers as specified in Example 1 were determined in human T cell leukemia cell line Jurkat cells. For example, for SDF-1 binding Spiegelmer NOX-A12 (also referred to as 193-G2-012-5'-PEG) an IC50 of 0.2 nM was determined (FIG. 10). When an unspecific Control Spiegelmer was used instead of SDF-1 binding Spiegelmers, no inhibitory effect was observed up to 1 μM.

Inhibition of the SDF-1 induced chemotaxis by SDF-1 binding spiegelmer NOX-A12 was also observed in three other different leukemia cell types: the human leukemic monocyte lymphoma cell line U937 (FIG. 11B), the human pre-B cell leukemia cell line BV-173 (FIG. 12) and the human pre-B ALL cell line Nalm-6 (FIG. 11A). Furthermore, we have evidence that primary chronic lymphocytic leukemia cells migrate towards SDF-1 and that SDF-1 dependent chemotaxis is effectively blocked by NOX-A12.

The leukemia lines BV-173 and U-937 were tested positive also for CXCR7 expression. The potency of SDF-binding spiegelmer NOX-A12 to block interaction of SDF-1 and CXCR7 was determined as shown in Example 6.

EXAMPLE 6: INHIBITION OF CXCR7 ACTIVATION BY SDF-1-BINDING SPIEGELMER NOX-A12

Besides CXCR4, SDF-1 also binds to the chemokine receptor CXCR7. The inhibitory potential of SDF-1-binding Spiegelmer NOX-A12 towards CXCR7 was tested in a complementation assay with CHO cells stably expressing CXCR7 and β-arrestin both fused to a fragment of β-galactosidase (PathHunter™—β-arrestin assay, DiscoveRX, CA, USA). Upon SDF-1 binding β-arrestin complexed with CXCR7 and thus led to complementation and activation of the β-galactosidase which was measured with a chemiluminescence substrate.

Method

PathHunter eXpress CHO-K1 Human CXCR7 β-arrestin cells were plated for 48 hours in OCC2 Medium and stimulated with 10 nM SDF-1 and various concentrations of SDF-1-binding Spiegelmer NOX-A12 for 90 minutes. Following stimulation, signal was detected using the PathHUnter Detection Kit and the manufacturer's recommended protocol (DiscoveRX, CA, USA).

Results

Stimulation of β-galactosidase and hence CXCR7 activation with 10 nM human SDF-1 was efficiently blocked by SDF-1-binding Spiegelmer NOX-A12 with an $IC_{50}$ of 5.4 nM (FIG. 13).

EXAMPLE 7: FUNCTIONAL ANALYSIS OF HUMAN SDF-1 BINDING SPIEGELMER 193-G2-012-5'-PEG IN AN AORTIC RING SPROUTING ASSAY

To test whether human SDF-1 binding Spiegelmer 193-G2-012-5'-PEG is functional also in a standard angiogenesis organ culture assay, aortic ring sprouting assays were performed. This assay, in which the length and abundance of vessel-like extensions from the explants are evaluated, has become the most widely used organ culture model for angiogenesis (Auerbach et al. 2003). It has already been shown that SDF-1 induces sprouting in this type of assay (Salcedo et al. 1999).

Rat aortae were cut into rings, embedded in a collagen matrix and incubated with SDF-1 and SDF-1 plus human SDF-1 binding Spiegelmer 193-G2-012-5'-PEG or SDF plus an non-functional PEGylated Control Spiegelmer that does not bind SDF-1. After 6 to 7 days, sprouting (i.e. outgrowth of endothelial cells) was analysed by taking pictures and determining a sprouting index.

Method

Aortae from male rats were obtained from Bagheri Life sciences (Berlin, Germany). The aortae were prepared freshly and transported on ice in MCDB 131-Medium (Invitrogen, Karlsruhe, Germany) containing 50 units/ml penicillin, 50 μg/ml streptomycin (both Invitrogen, Karlsruhe, Germany) and 2.5 μg/ml fungizone (Cambrex, USA).

For an experiment a single aorta was transferred to a cell culture dish together with the medium and residual connective tissue was removed. Then the aorta was cut with a scalpel into rings of about 1 to 2 mm length. The rings were washed intensively (at least five times) in Medium199 (Invitrogen, Karlsruhe, Germany) and then placed in wells of a 24 well plate, containing 450 μl of collagen solution per well. This collagen solution was prepared by mixing 9 ml rat tail collagen (3 mg/ml in 0.1% acetic acid; Sigma, Deisenhofen, Germany) with 1.12 ml 10× Medium 199 (Invitrogen, Karlsruhe, Germany), 1.12 ml 10× Collagen-buffer (0.05 N NaOH, 200 mM HEPES, 260 mM $NaHCO_3$) and 0.6 ml 200 mM Glutamin. The rings were oriented such that the trimmed edges were perpendicular to the bottom of the well. The collagen was allowed to solidify by incubating the plates for at least one hour at 37° C. Thereafter 1 ml MCDB131-medium with additions (SDF-1 and Spiegelmers) was added per well. Rings were then incubated at 37° C. for six to seven days. As control for sprouting the experiments were additionally done with VEGF (Vascular endothelial growth factor).

Sprouting was documented by taking pictures with a digital camera. In some cases rings were fixed by addition of 1 ml 10% paraformaldehyde and stored at 2-8° C. for further documentation. Pictures were analysed with the Scion Image image processing software. After calibration with the help of a picture taken from a stage micrometer, a line was drawn in a distance of 0.33 mm from one edge of a ring. A plot histogram along this line was generated by the software, histograms were printed and peaks (representing sprouts crossing the line) were counted. This number was taken as sprouting index. 4 to 5 rings per condition were evaluated. Statistical analysis was performed with WinSTAT for Excel.

Results

It could be demonstrated that SDF-1 induces sprouting and that this effect could be blocked with human SDF-1 binding Spiegelmer 193-G2-012-5'-PEG No blockage of SDF-1 induced sprouting was observed by the non-functional PEGylated Control Spiegelmer (FIGS. 14 and 15).

EXAMPLE 8: EFFECT OF SDF-1 BINDING SPIEGELMER NOX-A12 ON CHEMOSENSITIZATION OF LEUKEMIA CELLS

There is considerable evidence that leukemia cells may be protected from conventional chemotherapies by interaction between their CXCR4 receptors with SDF-1 secreted by stromal cells within particular tissue microenvironments such as the bone marrow (abbr. BM) niche. Therefore, targeting the CXCR4-SDF-1 axis by using the SDF-1 binding Spiegelmer NOX-A12 is an attractive approach for disrupting the protective effects of SDF-1-secreting stromal cells and for sensitizing leukemia cells towards subsequent chemotherapy.

In order to mimic the in vivo interaction of the BM microenvironment with leukemia cells, an in vitro coculture system with murine BM stromal MS-5 cells and the multiple myeloma (abbr. MM) cell line RPMI 8226 was established. Aim of the experiment was to show whether SDF-1 binding Spiegelmer NOX-A12 sensitizes MM cells in coculture with stromal cells to effects of chemotherapeutic agents. Stromal MS-5 cells secreting SDF 1 were incubated with SDF-1 binding Spiegelmer NOX-A12 or the non-functional revNOX-A12. The MM cell line RPMI-8226 was added to the confluent stromal cell layer. The cells were then incubated with the chemotherapeutic agent F ara A (Fludarabine) for 40 hours. Cell Viability was measured.

Method

The murine stromal cell line MS-5 (ACC 441) was purchased from the DSMZ, the Multiple Myeloma cell line RPMI8226 (CCL-155) was purchased from the ATCC. The Multiple Myeloma cell line RPMI8226 was maintained in RPMI medium 1640 GlutaMAX (Invitrogen) supplemented with 10% FBS (Biochrom) and penicillin-streptomycin, the MS-S cells were cultured in MEM alpha GlutaMAX (Invitrogen) with 10% FBS and penicillin-streptomycin. For chemosensitization coculture experiments stromal MS-5 cells were seeded the day before onto 24-well plates (the inner eight wells) at a concentration of 8×104/mL/well in MEM alpha GlutaMAX medium (+10% FBS) and incubated at 37° C. in 5% CO2. The confluent stromal cell layer was washed and 0.5 mL RPMI medium 1640 (+1% FBS) was added to the wells. SDF-1 binding Spiegelmer NOX-A12 or revNOX-A12 was subsequently added to the wells to a final concentration of 100 nM and incubated for four hours. 3.5×105 RPMI8226 cells in RPMI medium 1640 (+1% FBS) were added to the stromal cell layer. Four hours later, 1 µM F-ara-A (Sigma Aldrich) was added to the cells when indicated. After 40 hours of incubation the cells were collected in 15 mL tubes, first the supernatant was harvested and then the attached cells were trypsinized including MS-5 cells. The collected cells were washed twice with PBS (+1% BSA) and resupended in 2 mL PBS (+1% BSA). 150 µL of the cell suspension was transferred in a u-shape 96-well plate and then incubated with 50 µL of ViaCount Reagent (Millipore) for 15 minutes at room temperature. Cell viability and cell number were determined by Flow Cytometry using the Guava EasyCyte 6HT/2L (Millipore).

Results

Cell viability of RPMI-8226 cells cocultured with stromal MS-S cells was only slightly affected by SDF-1 binding Spiegelmer NOX A12. 1 µM F-ara-A showed no significant effect on the viability of RPMI-8226 cells. However, when NOX-A12 and F-ara-A were combined, a synergistic decrease of cell viability was observed (FIG. 16). Thus, SDF-1 binding Spiegelmer NOX-A12 was shown to sensitize the MM cell line RPMI-8226 towards treatment of the chemotherapeutic agent F-ara-A when cocultured with the BM stromal cell line MS 5. The viability of stromal MS-5 cells is neither affected by F-ara-A nor by NOX-A12 (data not shown). These results demonstrate a proof of principle in the potential of NOX A12 in disrupting to disrupt the protective effects of SDF-1 secreted by BM stromal cells.

EXAMPLE 9: EFFECT OF SDF-1 BINDING SPIEGELMER NOX-A12 ON PROLIFERATION OF LEUKEMIA CELLS

Aim of the experiment was to show whether SDF-1 binding Spiegelmer NOX-A12 has an impact on proliferation of leukemia cells in coculture with bone marrow (abbr. BM) stromal cells. Murine stromal MS-5 cells secreting SDF-1 were incubated with SDF-1 binding Spiegelmer NOX-A12 or the non-functional Spiegelmer revNOX-A12. The leukemic T-cell line Jurkat was added to the confluent stromal cell layer and incubated for 40 hours at 37° C. and 5% CO2. Cell numbers were quantified by Flow Cytometry using the Guava EasyCyte and ViaCount Reagent.

Method

The murine stromal cell line MS-5 (ACC 441) were purchased from the DSMZ and were cultured in MEM alpha GlutaMAX (Invitrogen) with 10% FBS and penicillin-streptomycin. For proliferation coculture experiments stromal MS-5 cells were seeded the day before onto 24-well plates (the inner eight wells) at a concentration of 8×104/mL/well in MEM alpha GlutaMAX medium (+10% FBS) and incubated at 37° C. in 5% C02. The confluent stromal cell layer was washed and 0.5 mL RPMI medium 1640 (+1% FBS) was added to the wells. SDF-1 binding Spiegelmer NOX-A12 or Spiegelmer revNOX A12 was subsequently added to the wells to a final concentration of 100 nM and incubated for four hours. 2×105 Jurkat cells (~logarithmic growth phase; washed once) in RPMI medium 1640 (+1% FBS) were added to the confluent stromal cell layer and incubated for 48 hours at 37° C. with 5% CO2. The cells were then collected in 15 mL tubes, attached cells were trypsinized including MS-S cells. The collected cells were washed twice with PBS (+1% BSA). 150 µL of this cell suspension was transferred in a u-shape 96-well plate and then incubated with 50 µL ViaCount Reagent (Millipore) for 15 minutes at room temperature. Cell viability and cell number were determined by Flow Cytometry using the Guava EasyCyte 6HT/2L.

Results

While 1 nM SDF-1 binding Spiegelmer NOX-A12 showed no effect on the Jurkat cell number after 40 hours of cultivation, the cell number was reduced up to 20% when stromal MS-5 cells were preincubated with 10 or 100 nM SDF-1 binding Spiegelmer NOX-A12 (FIG. 17). Thus, SDF-1 secreted by stromal cells apparently stimulates the proliferation of Jurkat cells. The SDF-1 dependent induction of proliferation can be blocked by SDF-1 binding Spiegelmer NOX-A12 leading to the detection of fewer a lower amount of leukemic cells.

EXAMPLE 10: EFFECT OF SDF-1 BINDING SPIEGELMER NOX-A12 ON ADHESIVE PROPERTIES OF LEUKEMIA CELLS

The interaction of leukemic cells with extracellular matrix (abbr. ECM) proteins plays a crucial role in leukemia pathogenesis. Therefore we tested the effect of SDF-1 binding Spiegelmer NOX-A12 on adhesion of leukemia cells on the ECM protein fibronectin. Stimulation of the Jurkat leukemia T-cell line with SDF-1 led to a dose-dependent modulation of adhesion on to fibronectin.

Methods

The T cell leukemia Jurkat (ACC 282) were purchased from the DSMZ were maintained in RPMI medium 1640 GlutaMAX (Invitrogen) supplemented with 10% FBS (Biochrom) and penicillin-streptomycin. For the adhesion experiments 96-well culture plates were incubated with 10 µg/mL human fibronectin (R&D systems) in PBS for 2 hours at 37° C. The plates were washed twice with 100 µL PBS and subsequently blocked with PBS-BSA (0.1%) for two hours at 37° C. The wells were then washed with RPMI medium. Jurkat cells from logarithmic growth phase were washed with RPMI medium (+0.1% BSA) and incubated with various concentrations of human SDF-1 (R&D systems) and NOX-A12 for 15 minutes at 37° C. NOX-A12 and SDF-1 were preincubated for 30 minutes. 1×105 stimulated Jurkat cells were seeded to the Fibronectin-coated 96-well plates and incubated for 30 minutes. The plates were then washed five times with RPMI medium. Attached cells were quantified by using Cell Titer Glo Reagent (Promega). Therefor, 50 µL RPMI medium was added to each well, followed by 50 µL of Cell Titer Glo Reagent. The plates were mixed for two minutes, followed by incubation at room temperature for 10 minutes. Cell number was quantified by relative luminescence signal.

Results

Low to medium concentrations of SDF-1 (1-10 nM) decreased the adhesion of Jurkat cells to fibronectin, while higher concentrations (30-300 nM) increased the adhesive properties of Jurkat cells (FIG. 18A). SDF-1 binding Spiegelmer NOX-A12 was shown to reverse this effect, the control Spiegelmer revNOX-A12 not (FIG. 18B). Thus SDF-1 binding Spiegelmer NOX-A12 might have an impact on the disruption of leukemic cell interactions with their protective ECM environment. Furthermore, this example might explain SDF-1 binding Spiegelmer NOX-A12 dependent detachment and mobilization of hematopoetic cells from the bone marrow niche.

EXAMPLE 11: DISRUPTION OF THE INTERACTION OF MULTIPLE MYELOMA CELLS WITH THE BONE MARROW ENVIRONMENT IN VIVO THEREBY ENHANCING THE SENSITIVITY OF THE MULTIPLE MYELOMA CELLS TO THERAPY

The SDF-1/CXCR4 axis plays a major role in homing and trafficking of multiple myeloma (abbr. MM) cells to the bone marrow (abbr. BM). Therefore, de-adhesion of MM cells from the surrounding BM milieu through SDF-1 inhibition enhances MM sensitivity to therapeutic agents. Azab et al. published a protocol to test the CXCR4 inhibitor AMD3100 potency to disrupt the interaction of MM cells with the BM environment in vivo that affects localization MM cells [, which in turn enhances the sensitivity of MM cells to chemotherapy. They reported that the blockade of the SDF-1 receptor CXCR4 by the CXCR4 specific antagonist led to a disruption of the interaction of MM cells with the BM environment in vivo, to enhanced sensitivity of the MM cells to therapy, and as a result to enhanced tumor reduction induced by bortezomib (Azab et al. 2009). Based on this protocol (Azab et al. 2009) the SDF-1 binding Spiegelmer NOX-A12 is tested for its potency to disrupt the interaction of MM cells with the BM environment in vivo thereby enhancing the sensitivity of the MM cells to therapy.

For the MM animal model severe combined immunodeficient (SCID) mice are used whereby Luc+/GFP+MM.1S cells ($2\times10^6$/mouse) are injected into the tail vein of SCID mice. After 3 to 4 weeks, sufficient tumor progression is detected by bioluminescence imaging (for protocol see Azab et al. 2009). Mice are randomly divided into 4 groups: group 1, control mice (received vehicle: 5% glucose); group 2, mice treated every other day with 20 mg/kg NOX-A12 subcutaneous injection; group 3, mice treated with intraperitoneal bortezomib injection of 0.5 mg/kg twice a week; group 4, mice treated with intraperitoneal bortezomib injection of 0.5 mg/kg twice a week and every other day with 20 mg/kg NOX-A12 subcutaneous injection.

The localization of the MM tumor cells in the bone marrow is determined in vivo confocal microscopy using a fluorescence labelled anti-SDF antibody (for protocol see Azab et al. 2009), whereby the administration of NOX-A12 leads to MM cell mobilization from bone marrow to the blood (as determined by ex vivo flow cytometry; for protocol see Azab et al. 2009) and to a reduction of tumor growth when administered together with bortezomib (by in vivo bioluminescence detection; for protocol see Mitsiades et al., 2003; Mitsiades et al. 2004). The stronger effects on tumor growth by bortezomib plus NOX-A12 in comparison to a treatment with bortezomib alone support the data of Example 8 showing positive effects of NOX-12 on chemosensitization of MM cells.

REFERENCES

The complete bibliographic data of the documents recited herein are, if not indicated to the contrary, as follows, whereby the disclosure of said references is incorporated herein by reference.

Alsayed Y., Ngo H., et al. (2007) Mechanisms of regulation of CXCR4/SDF-1 (CXCL12)-dependent migration and homing in multiple myeloma. Blood 109(7): 2708-17.

Altschul S. F., Gish W., et al. (1990) Basic local alignment search tool. J Mol Biol. 215(3):403-10.

Altschul S. F., Madden T. L., et al. (1997) Gapped BLAST and PSI-BLAST: a new generation of protein database search programs. Nucleic Acids Res. 25(17):3389-402.

Arya S. K., Ginsberg C. C., et al. (1999) In vitro phenotype of SDF1 gene mutant that delays the onset of human immunodeficiency virus disease in vivo. J Hum Virol 2(3): 133-8.

Auerbach R., Lewis R., et al. (2003) Angiogenesis assays: a critical overview. Clin Chem. 49(1):32-40. Review.

Azab A. K., Runnels J. M., et al. (2009) CXCR4 inhibitor AMD3100 disrupts the interaction of multiple myeloma cells with the bone marrow microenvironment and enhances their sensitivity to therapy. Blood. 113(18): 4341-51.

Batchelor T. T., Sorensen A. G., et al. (2007) AZD2171, a pan-VEGF receptor tyrosine kinase inhibitor, normalizes tumor vasculature and alleviates edema in glioblastoma patients. Cancer Cell. 11(1):83-95.

Balabanian K., Lagane B., et al. (2005) The chemokine SDF-1/CXCL12 binds to and signals through the orphan receptor RDC1 in T lymphocytes. J Biol Chem 280(42): 35760-35766

Balabanian, K., Lagane B, et al. (2005) WHIM syndromes with different genetic anomalies are accounted for by impaired CXCR4 desensitization to CXCL12. Blood 105 (6): 2449-57.

Balkwill F. (2004) Cancer and the chemokine network. Nat Rev Cancer 4(7): 540-50.

Brooks H. L. Jr., Caballero S. Jr., et al. (2004) Vitreous levels of vascular endothelial growth factor and stromal-derived factor 1 in patients with diabetic retinopathy and cystoid macular edema before and after intraocular injection of triamcinolone. Arch Ophthalmol 122(12): 1801-7.

Broxmeyer H. E., Orschell C. M., (2005) Rapid mobilization of murine and human hematopoietic stem and progenitor cells with AMD3100, a CXCR4 antagonist. J Exp Med. 201(8):1307-18.

Buckley C. D., Amft N., et al. (2000) Persistent induction of the chemokine receptor CXCR4 by TGF-beta 1 on synovial T cells contributes to their accumulation within the rheumatoid synovium. J Immunol 165(6): 3423-9.

Burger J. A., Bürkle A, et al. (2007) The CXCR4 chemokine receptor in acute and chronic leukaemia: a marrow homing receptor and potential therapeutic target. Br J Haematol. 137(4):288-96.

Burger J. A., Ghia P., et al. (2009) The microenvironment in mature B-cell malignancies: a target for new treatment strategies. Blood. 114(16):3367-75. Review Burger J. A., Kipps T. J. et al. (2002) Chemokine receptors and stromal cells in the homing and homeostasis of chronic lymphocytic leukemia B cells. Leuk Lymphoma. 43(3):461-6

Burger J. A. and Peled A. (2009) CXCR4 antagonists: targeting the microenvironment in leukemia and other cancers. Leukemia 23(1): 43-52.

Burger J. A., Tsukada N., et al. (2000) Blood-derived nurse-like cells protect chronic lymphocytic leukemia B cells from spontaneous apoptosis through stromal cell-derived factor-1. Blood. 96(8):2655-63.

Burns J. M., Summers B. C., et al. (2006) A novel chemokine receptor for SDF-1 and 1-TAC involved in cell survival, cell adhesion, and tumor development. J Exp Med 203(9): 2201-2213

Butler J. M., Guthrie S. M., et al. (2005) SDF-1 is both necessary and sufficient to promote proliferative retinopathy. J Clin Invest 115(1): 86-93

Cabioglu, N., Sahin A., et al. (2005) Chemokine receptor CXCR4 expression in breast cancer as a potential predictive marker of isolated tumor cells in bone marrow. Clin Exp Metastasis 22(1): 39-46.

Ceradini D. J., Kulkarni A. R., et al. (2004) Progenitor cell trafficking is regulated by hypoxic gradients through HIF-1 induction of SDF-1. Nat Med. 10(8):858-64.

Corcione A., Ottonello L., et al. (2000) Stromal cell-derived factor-1 as a chemoattractant for follicular center lymphoma B cells. J Natl Cancer Inst 92(8): 628-35.

Damha M. J., Ogilvie K. K., et al. (1993) Oligoribonucleotide synthesis. The silyl-phosphoramidite method. Methods Mol Biol. 20:81-114.

Damiano J. S., Cress A. E., et al. (1999) Cell adhesion mediated drug resistance (CAM-DR): role of integrins and resistance to apoptosis in human myeloma cell lines. Blood. 93(5): 1658-67

Devine S. M., Flomenberg N., et al. (2004) Rapid mobilization of CD34+ cells following administration of the CXCR4 antagonist AMD3100 to patients with multiple myeloma and non-Hodgkin's lymphoma. J Clin Oncol. 22(6):1095-102.

Dillmann F., Veldwijk M. R, et al. (2009) Plerixafor inhibits chemotaxis toward SDF-1 and CXCR4-mediated stroma contact in a dose-dependent manner resulting in increased susceptibility of BCR-ABL+ cell to Imatinib and Nilotinib. Leuk Lymphoma. 50(10):16

Ehtesham M., Stevenson C. B., et al. (2008) Preferential expression of chemokine receptor CXCR4 by highly malignant human gliomas and its association with poor patient survival. Neurosurgery. 63(4):E820

Engl T., Relja B., et al. (2006) CXCR4 chemokine receptor mediates prostate tumor cell adhesion through alpha5 and beta3 integrins. Neoplasia. 8(4):290-301.

Fedyk E. R., Jones D., et al. (2001) Expression of stromal-derived factor-1 is decreased by IL-1 and TNF and in dermal wound healing. J Immunol. 166(9):5749-54.

Geminder H., Sagi-Assif O., et al. (2001) A possible role for CXCR4 and its ligand, the CXC chemokine stromal cell-derived factor-1, in the development of bone marrow metastases in neuroblastoma. J Immunol 167(8): 4747-57.

Grassi F., Cristino S., et al. (2004) CXCL12 chemokine up-regulates bone resorption and MMP-9 release by human osteoclasts: CXCL12 levels are increased in synovial and bone tissue of rheumatoid arthritis patients. J Cell Physiol 199(2): 244-51.

Grunewald M., Avraham I., et al. (2006) VEGF-induced adult neovascularization: recruitment, retention, and role of accessory cells. Cell 124(1): 175-89.

Gulino, A. V., Moratto D., et al. (2004) Altered leukocyte response to CXCL2 in patients with warts hypogammaglobulinemia, infections, myelokathexis (WHIM) syndrome. Blood 104(2): 444-52.

Holm N. T., Abreo F., et al. (2009) Elevated chemokine receptor CXCR4 expression in primary tumors following neoadjuvant chemotherapy predicts poor outcomes for patients with locally advanced breast cancer (LABC). Breast Cancer Res Treat. 113(2):293-9. Epub 2008 Feb. 13

Hwang J. H., Chung H. K., et al. (2003) CXC chemokine receptor 4 expression and function in human anaplastic thyroid cancer cells. J Clin Endocrinol Metab 88(1): 408-16.

Jin L., Tabe Y., et al. (2008) CXCR4 up-regulation by imatinib induces chronic myelogenous leukemia (CML) cell migration to bone marrow stroma and promotes survival of quiescent CML cells. Mol Cancer Ther 7(1): 48-58

Kanbe K., Takagishi K., et al. (2002) Stimulation of matrix metalloprotease 3 release from human chondrocytes by the interaction of stromal cell-derived factor 1 and CXC chemokine receptor 4. Arthritis Rheum 46(1): 130-7.

Kawai T., Choi U., et al. (2005) Enhanced function with decreased internalization of carboxy-terminus truncated CXCR4 responsible for WHIM syndrome. Exp Hematol 33(4): 460-8.

Kioi M., Vogel H., et al. (2010) Inhibition of vasculogenesis, but not angiogenesis, prevents the recurrence of glioblastoma after irradiation in mice. J Clin Invest 120(3): 694-705.

Klussmann S. (2006). The Aptamer Handbook—Functional Oligonucleotides and their Applications. Edited by S. Klussmann. WILEY-VCH, Weinheim, Germany, ISBN 3-527-31059-2

Koshiba T., Hosotani R., et al. (2000) Expression of stromal cell-derived factor 1 and CXCR4 ligand receptor system in pancreatic cancer: a possible role for tumor progression. Clin Cancer Res 6(9): 3530-5.

Kozin S. V., Kamoun W. S., et al. (2010) Recruitment of myeloid but not endothelial precursor cells facilitates tumor regrowth after local irradiation. Cancer Res 70(14): 5679-85.

Krumbholz M., Theil D., et al. (2006) Chemokines in multiple sclerosis: CXCL12 and CXCL13 up-regulation is differentially linked to CNS immune cell recruitment. Brain 129: 200-211.

Kryczek I., Lange A., et al. (2005) CXCL12 and vascular endothelial growth factor synergistically induce neoangiogenesis in human ovarian cancers. Cancer Res 65(2): 465-72.

Kurtova A. V., Balakrishnan K., et al. (2009) Diverse marrow stromal cells protect CLL cells from spontaneous and drug-induced apoptosis: development of a reliable and reproducible system to assess stromal cell adhesion-mediated drug resistance. Blood. 114(20):4441-50.

Kusser W. (2000) Chemically modified nucleic acid aptamers for in vitro selections: evolving evolution. J Biotechnol 74(1): 27-38.

Lagneaux L., Delforge A., et al. (1998) Chronic lymphocytic leukemic B cells but not normal B cells are rescued from apoptosis by contact with normal bone marrow stromal cells. Blood. 91(7):2387-96.

Li J. K., Yu L., et al. (2008) Inhibition of CXCR4 activity with AMD3100 decreases invasion of human colorectal cancer cells in vitro. World J Gastroenterol 14(15): 2308-2313

Maksym R. B., Tarnowski M., et al. (2009) The role of stromal-derived factor-1—CXCR7 axis in development and cancer. Eur J Pharmacol. 625(1-3):31-40. Review.

Marechal V., Arenzana-Seisdedos F., et al. (1999) Opposite effects of SDF-1 on human immunodeficiency virus type 1 replication. J Viral 73(5): 3608-15.

McGinnis S., Madden T. L. et al. (2004) BLAST: at the core of a powerful and diverse set of sequence analysis tools. Nucleic Acids Res. 32(Web Server issue):W20-5.

Meads M. B., Hazlehurst L. A., et al. (2008) The bone marrow microenvironment as a tumor sanctuary and contributor to drug resistance. Clin Cancer Res. 14(9): 2519-26. Review.

Meleth A. D., Agron E., et al. (2005) Serum inflammatory markers in diabetic retinopathy. Invest Ophthalmol Vis Sci 46(11): 4295-301.

Miao, Z., Luker K. E., et al. (2007) CXCR7 (RDC1) promotes breast and lung tumor growth in vivo and is expressed on tumor-associated vasculature. Proc Natl Acad Sci USA 104(40): 15735-40.

Mitsiades C. S., Mitsiades N. S., et al. (2003) Fluorescence imaging of multiple myeloma cells in a clinically relevant SCID/NOD in vivo model: biologic and clinical implications. Cancer Res. 63(20):6689-96.

Mitsiades C. S., Mitsiades N., et al. (2004) Focus on multiple myeloma. Cancer Cell. 6(5):439-44. Review.

Mizell J., Smith M., et al. (2009) Overexpression of CXCR4 in primary tumor of patients with HER-2 negative breast cancer was predictive of a poor disease-free survival: a validation study. Ann Surg Oncol. 16(10):2711-6.

Muller, A., Homey B., et al. (2001) Involvement of chemokine receptors in breast cancer metastasis. Nature 410(6824): 50-6.

Murdoch, C. (2000) CXCR4: chemokine receptor extraordinaire. Immunol Rev 177: 175-84.

Needleman and Wunsch (1970) A general method applicable to the search for similarities in the amino acid sequence of two proteins. J Mol Biol. 48(3):443-53.

Nervi B., Ramirez P., et al. (2009) Chemosensitization of acute myeloid leukemia (AML) following mobilization by the CXCR4 antagonist AMD3100. Blood. 113(24): 6206-14. Epub 2008 Dec. 2

Pearson and Lipman (1988) Improved tools for biological sequence comparison. Proc. Nat'l. Acad. Sci. USA 85: 2444

Redjal N., Chan J. A., et al. (2006) CXCR4 inhibition synergizes with cytotoxic chemotherapy in gliomas. Clin Cancer Res. 12(22):6765-71.

Salcedo R., Wasserman K., et al. (1999) Vascular endothelial growth factor and basic fibroblast growth factor induce expression of CXCR4 on human endothelial cells: in vivo neovascularization induced by stromal-derived factor-1alpha. Am J Pathol 154(4): 1125-1135

Salcedo, R. and Oppenheim J. J. (2003) Role of chemokines in angiogenesis: CXCL12/SDF-1 and CXCR4 interaction, a key regulator of endothelial cell responses. Microcirculation 10(3-4): 359-70.

Salvucci O., Yao L., et al. (2002) Regulation of endothelial cell branching morphogenesis by endogenous chemokine stromal-derived factor-1. Blood 99(8): 2703-11.

Saur D., Seidler B., at al. (2005) CXCR4 expression increases liver and lung metastasis in a mouse model of pancreatic cancer. Gastroenterology. 129(4):1237-50.

Schimanski C. C., Galle P. R., et al. (2008) Chemokine receptor CXCR4-prognostic factor for gastrointestinal tumors. World J Gastroenterol. 14(30):4721.4.

Scotton C. J., Wilson J. L., et al. (2002) Multiple actions of the chemokine CXCL12 on epithelial tumor cells in human ovarian cancer. Cancer Res. 62(20):5930-8

Sengupta N, Caballero S., at al. (2005) Preventing stem cell incorporation into choroidal neovascularization by targeting homing and attachment factors. Invest Ophthalmol Vis Sci. 46(1):343-8.

Shaked Y., Henke E., et al. (2008) Rapid chemotherapy-induced acute endothelial progenitor cell mobilization: implications for antiangiogenic drugs as chemosensitizing agents. Cancer Cell. 14(3):263-73

Shirozu M., Nakano T., et al. (1995) Structure and chromosomal localization of the human stromal cell-derived factor 1 (SDF1) gene. Genomics 28(3): 495-500.

Smith and Waterman (1981), Adv. Appl. Math. 2: 482

Soriano A., Martinez C., et al. (2002) Plasma stromal cell-derived factor (SDF)-1 levels, SDF-3'A genotype, and expression of CXCR4 on T lymphocytes: their impact on resistance to human immunodeficiency virus type 1 infection and its progression. J Infect Dis 186(7): 922-31.

Su L., Zhang J. et al. (2005) Differential expression of CXCR4 is associated with the metastatic potential of human non-small cell lung cancer cells. Clin Cancer Res. 11(23):8273-80.

Tseng D., Lartey F. et al. (2010) J. K., Yu L., et al. (2008) (MS108) Inhibition of SDF-1/CXCR7 radiosensitizes ENU induced glioblastomas in the rat. 56th Annual Meeting Radiation Research Society, Sep. 25-29, 2010, Grand Wailea Resort Hotel and Spa, Maui, Hi., USA Venkatesan N., Kim S. J., et al. (2003) Novel phosphoramidite building blocks in synthesis and applications toward modified oligonucleotides. Curr Med Chem 10(19): 1973-91.

Wang J., Shiozawa Y., at al. (2008) The role of CXCR7/RDC1 as a chemokine receptor for CXCL12/SDF-1 in prostate cancer. J Biol Chem 283(7): 4283-4294. Epub 2007 Dec. 5.

Wang J., Guan E., et al. (2001) Role of tyrosine phosphorylation in ligand-independent sequestration of CXCR4 in human primary monocytes-macrophages. J Biol Chem 276(52): 49236-43.

Wang N., Wu Q. L., et al. (2005) Expression of chemokine receptor CXCR4 in nasopharyngeal carcinoma: pattern of expression and correlation with clinical outcome. J Transl Med 3: 26.

Xu L., Duda D. G., et al. (2009) Direct evidence that bevacizumab, an anti-VEGF antibody, up-regulates SDF1alpha, CXCR4, CXCL6, and neuropilin 1 in tumors from patients with rectal cancer. Cancer Res. 69(20): 7905-10.

Yamaguchi J., Kusano K. F., et al. (2003) Stromal cell-derived factor-1 effects on ex vivo expanded endothelial progenitor cell recruitment for ischemic neovascularization. Circulation 107(9): 1322-8.

Yang J., Zhang B. et al. (2008) Breast cancer metastasis suppressor 1 inhibits SDF-1alpha-induced migration of non-small cell lung cancer by decreasing CXCR4 expression. Cancer Lett 269(1):46-56

Zagzag D., Esencay M., at al. (2008) Hypoxia- and vascular endothelial growth factor-induced stromal cell-derived factor-1alpha/CXCR4 expression in glioblastomas: one plausible explanation of Scherer's structures. Am J Pathol 173(2): 545-560

Zeelenberg I. S., Ruuls-Van Stalle L., et al. (2003) The chemokine receptor CXCR4 is required for outgrowth of colon carcinoma micrometastases. Cancer Res. 63(13): 3833-9.

Zheng K., Li H. Y., et al. (2010) Chemokine receptor CXCR7 regulates the invasion, angiogenesis and tumor growth of human hepatocellular carcinoma cells. J Exp Clin Cancer Res. 29:31.

Zhou Y., Larsen P. H., et al. (2002) CXCR4 is a major chemokine receptor on glioma cells and mediates their survival. J Biol Chem 277(51): 49481-7.

Zhu A. X., Sahani D. V., et al. (2009) Efficacy, safety, and potential biomarkers of sunitinib monotherapy in advanced hepatocellular carcinoma: a phase II study. J Clin Oncol 27(18): 3027-35.

The features of the present invention disclosed in the specification, the claims and/or the drawings may both separately and in any combination thereof be material for realizing the invention in various forms thereof.

The invention claimed is:

1. A method for the treatment of a subject suffering from cancer, wherein the method comprises a) administering to the subject a pharmaceutically effective amount of a type B L-nucleic acid, or a homolog thereof, that binds SDF-1, wherein said type B L-nucleic acid comprises, in order, a 5' flanking sequence, SEQ ID NO:52 and a 3' flanking sequence, wherein said 5' and 3' flanking sequences can hybridize to each other.

2. The method according to claim 1, wherein the method further comprises b) irradiating the subject, conducting surgery on said subject, exposing said subject to a cellular therapy and/or administering a pharmaceutically effective amount of a further pharmaceutically active agent to the subject.

3. The method of claim 1, wherein the cancer comprises a hematological cancer or a solid tumor.

4. The method of claim 2, wherein said L-nucleic acid is administered as an adjunct therapy or part of an adjunct therapy, with a primary treatment.

5. The method of claim 3, wherein said hematological cancer comprises leukemia or myeloma.

6. The method of claim 3, wherein said solid tumor comprises glioblastoma, colorectal cancer, breast cancer, lymphoma, prostate cancer, pancreatic cancer, renal cancer, ovarian cancer or lung cancer.

7. The method of claim 4, wherein the adjunct therapy sensitizes the subject to said primary treatment.

8. The method of claim 4, wherein said primary treatment comprises administrating a further pharmaceutically active agent to said subject, irradiating the subject, conducting surgery on said subject and/or exposing said subject to a cellular therapy.

9. The method of claim 8, wherein the further pharmaceutically active agent is selected from the group consisting of an antibody, an alkylating agent, an anti-metabolite, a plant alkaloid, a plant terpenoid, and a topoisomerase inhibitor.

10. The method of claim 8, wherein said further pharmaceutically active agent is selected from the group consisting of leucovorin, methotrexate, tamoxifen, sorafenib, lenalidomide, bortezomib, dexamethasone, flurouracil and prednisone.

11. The method of claim 9, wherein the antibody is selected from the group consisting of Rituximab, Ofatumumab, Cetuximab, Ibritumomab-Tiuxetan, Tositumomab, Trastuzumab, Bevacizumab, and Alemtuzumab.

12. The method of claim 9, wherein the alkylating agent is selected from the group consisting of cisplatin, carboplatin, oxaliplatin, mechlorethamine, cyclophosphamide, chlorambucil, doxorubicin, lioposomal doxorubicin, bendamustine, temozolomide and melphalan.

13. The method of claim 9, wherein the anti-metabolite is selected from the group consisting of purineazathioprine, mercaptopurine, fludarabine, pentostatin, and cladribine.

14. The method of claim 9, wherein the plant terpenoid comprises a taxane.

15. The method of claim 9, wherein the topoisomerase inhibitor is selected from the group consisting of camptothecin, irinotecan, and mitoxantrone.

16. The method of claim 1, wherein the L-nucleic acid comprises a modification.

17. The method of claim 16, wherein the modification is selected from the group consisting of an HES moiety, a PEG moiety, biodegradable modifications and combinations thereof.

18. The method of claim 16, wherein said modification enhances residence time in an animal or human host.

* * * * *

SEQUENCE LISTING

```
<160> NUMBER OF SEQ ID NOS: 225

<210> SEQ ID NO 1
<211> LENGTH: 68
<212> TYPE: PRT
<213> ORGANISM: Homo sapiens
<220> FEATURE:
<221> NAME/KEY: misc_feature
<223> OTHER INFORMATION: L-peptide

<400> SEQUENCE: 1

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 2
<211> LENGTH: 72
<212> TYPE: PRT
<213> ORGANISM: Homo sapiens
<220> FEATURE:
<221> NAME/KEY: misc_feature
<223> OTHER INFORMATION: L-peptide

<400> SEQUENCE: 2

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys Arg Phe Lys Met
65                  70

<210> SEQ ID NO 3
<211> LENGTH: 68
<212> TYPE: PRT
<213> ORGANISM: Mus musculus
<220> FEATURE:
<221> NAME/KEY: misc_feature
<223> OTHER INFORMATION: L-peptide
```

<400> SEQUENCE: 3

Lys Pro Val Ser Leu Ser Tyr Arg Cys Pro Cys Arg Phe Phe Glu Ser
1               5                   10                  15

His Ile Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 4
<211> LENGTH: 71
<212> TYPE: PRT
<213> ORGANISM: Homo sapiens
<220> FEATURE:
<221> NAME/KEY: misc_feature
<223> OTHER INFORMATION: D-peptide
<220> FEATURE:
<221> NAME/KEY: misc_feature
<223> OTHER INFORMATION: biotinylated at C-terminus

<400> SEQUENCE: 4

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys Arg Phe Lys
65                  70

<210> SEQ ID NO 5
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 5
agcguggugu gaucuagaug uaguggcuga uccuagucag guacgcu      47

<210> SEQ ID NO 6
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 6
agcguggugu gaucuagaug uauuggcuga uccuagucag guacgcu      47

<210> SEQ ID NO 7
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 7
agcguggugu gaucuagaug uaauggcuga uccuagucag gugcgcu             47

<210> SEQ ID NO 8
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 8
gcgaggugug aucuagaugu aguggcugau ccuagucagg ugcgc              45

<210> SEQ ID NO 9
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 9
gcguggugug aucuagaugu aguggcugau ccuagucagg ugcgc              45

<210> SEQ ID NO 10
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 10
gcauggugug aucuagaugu aguggcugau ccuagucagg ugccc              45

<210> SEQ ID NO 11
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 11
gcguggugug aucuagaugu aauggcugau ccuagucagg gacgc              45

<210> SEQ ID NO 12
<211> LENGTH: 45
<212> TYPE: DNA
<213> ORGANISM: artificial

<220> FEATURE:
<223> OTHER INFORMATION: synthetic
<220> FEATURE:
<221> NAME/KEY: misc_feature
<223> OTHER INFORMATION: L-RNA

<400> SEQUENCE: 12
gcguggugug aucuagaugu agaggcugau ccuagucagg uacgc         45

<210> SEQ ID NO 13
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 13
gcguggugug aucuagaugu aaaggcugau ccuagucagg uacgc         45

<210> SEQ ID NO 14
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 14
gcguggugug aucuagaugu aguggcuguu ccuagucagg uaugc         45

<210> SEQ ID NO 15
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 15
gcguggugug aucuagaugu aguggcugau ccuaguuagg uacgc         45

<210> SEQ ID NO 16
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 16
gcguggugug aucuagaugu aguggcugau ccuagucagg uacgc         45

<210> SEQ ID NO 17
<211> LENGTH: 43
<212> TYPE: DNA
<213> ORGANISM: artificial
<220> FEATURE:
<223> OTHER INFORMATION: synthetic

```
<220> FEATURE:
<221> NAME/KEY: misc_feature
<223> OTHER INFORMATION: L-RNA

<400> SEQUENCE: 17
cgugguguga ucuagaugua guggcugauc cuagucaggu acg         43

<210> SEQ ID NO 18
<211> LENGTH: 41
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 18
guggugugau cuagauguag uggcugaucc uagucaggua c           41

<210> SEQ ID NO 19
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 19
uggugugauc uagauguagu ggcugauccu agucaggua              39

<210> SEQ ID NO 20
<211> LENGTH: 37
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 20
ggugugaucu agauguagug gcugauccua gucaggu                37

<210> SEQ ID NO 21
<211> LENGTH: 35
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 21
gugugaucua gauguagugg cugauccuag ucagg                  35

<210> SEQ ID NO 22
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
```

```
<400> SEQUENCE: 22
gcguggugug aucuagaugu auuggcugau ccuagucagg uacgc           45

<210> SEQ ID NO 23
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 23
gcgcggugug aucuagaugu auuggcugau ccuagucagg cgcgc           45

<210> SEQ ID NO 24
<211> LENGTH: 43
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 24
gcgcguguga ucuagaugua uuggcugauc cuagucaggg cgc             43

<210> SEQ ID NO 25
<211> LENGTH: 43
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 25
gggcguguga ucuagaugua uuggcugauc cuagucaggg ccc             43

<210> SEQ ID NO 26
<211> LENGTH: 43
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 26
ggccguguga ucuagaugua uuggcugauc cuagucaggg gcc             43

<210> SEQ ID NO 27
<211> LENGTH: 43
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 27
gcccguguga ucuagaugua uuggcugauc cuagucaggg ggc             43
```

```
<210> SEQ ID NO 28
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (1)..(1)
<223> OTHER INFORMATION: 40 kDa-PEG-moiety attached to 5'-end

<400> SEQUENCE: 28
gcguggugug aucuagaugu auuggcugau ccuagucagg uacgc            45

<210> SEQ ID NO 29
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 29
agcguggugu gaucuagaug uaguggcuga uccuagucag guacgcu          47

<210> SEQ ID NO 30
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 30
agcguggugu gaucuagaug uauuggcuga uccuagucag guacgcu          47

<210> SEQ ID NO 31
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 31
agcguggugu gaucuagaug uaauggcuga uccuagucag gugcgcu          47

<210> SEQ ID NO 32
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 32
gcgaggugug aucuagaugu aguggcugau ccuagucagg ugcgc            45
```

<210> SEQ ID NO 33
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 33
gcguggugug aucuagaugu aguggcugau ccuagucagg ugcgc             45

<210> SEQ ID NO 34
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 34
gcauggugug aucuagaugu aguggcugau ccuagucagg ugccc             45

<210> SEQ ID NO 35
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 35
gcguggugug aucuagaugu aauggcugau ccuagucagg gacgc             45

<210> SEQ ID NO 36
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 36
gcguggugug aucuagaugu agaggcugau ccuagucagg uacgc             45

<210> SEQ ID NO 37
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 37
gcguggugug aucuagaugu aaaggcugau ccuagucagg uacgc             45

<210> SEQ ID NO 38
<211> LENGTH: 45
<212> TYPE: DNA
<213> ORGANISM: artificial

```
<220> FEATURE:
<223> OTHER INFORMATION: synthetic
<220> FEATURE:
<221> NAME/KEY: misc_feature
<223> OTHER INFORMATION: D-RNA

<400> SEQUENCE: 38
gcguggugug aucuagaugu aguggcuguu ccuagucagg uaugc            45

<210> SEQ ID NO 39
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 39
gcguggugug aucuagaugu aguggcugau ccuaguuagg uacgc            45

<210> SEQ ID NO 40
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 40
gcguggugug aucuagaugu aguggcugau ccuagucagg uacgc            45

<210> SEQ ID NO 41
<211> LENGTH: 43
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 41
cgugguguga ucuagaugua guggcugauc cuagucaggu acg              43

<210> SEQ ID NO 42
<211> LENGTH: 41
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 42
guggugugau cuagauguag uggcugaucc uagucaggua c                41

<210> SEQ ID NO 43
<211> LENGTH: 39
<212> TYPE: DNA
<213> ORGANISM: artificial
<220> FEATURE:
<223> OTHER INFORMATION: synthetic
```

```
<220> FEATURE:
<221> NAME/KEY: misc_feature
<223> OTHER INFORMATION: D-RNA

<400> SEQUENCE: 43
uggugugauc uagauguagu ggcugauccu agucaggua                           39

<210> SEQ ID NO 44
<211> LENGTH: 37
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 44
ggugugaucu agauguagug gcugauccua gucaggu                             37

<210> SEQ ID NO 45
<211> LENGTH: 35
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 45
gugugaucua gauguagugg cugauccuag ucagg                               35

<210> SEQ ID NO 46
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 46
gcguggugug aucuagaugu auuggcugau ccuagucagg uacgc                    45

<210> SEQ ID NO 47
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 47
gcgcggugug aucuagaugu auuggcugau ccuagucagg cgcgc                    45

<210> SEQ ID NO 48
<211> LENGTH: 43
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA
```

```
<400> SEQUENCE: 48
gcgcguguga ucuagaugua uuggcugauc cuagucaggg cgc          43

<210> SEQ ID NO 49
<211> LENGTH: 43
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 49
gggcguguga ucuagaugua uuggcugauc cuagucaggg ccc          43

<210> SEQ ID NO 50
<211> LENGTH: 43
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 50
ggccguguga ucuagaugua uuggcugauc cuagucaggg gcc          43

<210> SEQ ID NO 51
<211> LENGTH: 43
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 51
gcccguguga ucuagaugua uuggcugauc cuagucaggg ggc          43

<210> SEQ ID NO 52
<211> LENGTH: 35
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 52
gugugaucua gauguadwgg cugwuccuag uyagg                   35

<210> SEQ ID NO 53
<211> LENGTH: 35
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 53
gugugaucua gauguadugg cugauccuag ucagg                   35
```

```
<210> SEQ ID NO 54
<211> LENGTH: 27
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 54
aaaguaacac guaaaaugaa agguaac                                           27

<210> SEQ ID NO 55
<211> LENGTH: 26
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 55
aaagcaacau gucaaugaaa gguagc                                            26

<210> SEQ ID NO 56
<211> LENGTH: 18
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 56
gguuagggcu aaagucgg                                                     18

<210> SEQ ID NO 57
<211> LENGTH: 19
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 57
gguuagggcu agaagucgg                                                    19

<210> SEQ ID NO 58
<211> LENGTH: 19
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 58
gguuagggcu cgaagucgg                                                    19

<210> SEQ ID NO 59
<211> LENGTH: 19
<212> TYPE: DNA
<213> ORGANISM: artificial
```

```
<220> FEATURE:
<223> OTHER INFORMATION: synthetic
<220> FEATURE:
<221> NAME/KEY: misc_feature
<223> OTHER INFORMATION: L-RNA

<400> SEQUENCE: 59
gguuagggcu ugaagucgg                                                      19

<210> SEQ ID NO 60
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 60
gcugugaaag caacauguca augaaaggua gccgcagc                                 38

<210> SEQ ID NO 61
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 61
gcugugaaag uaacauguca augaaaggua accacagc                                 38

<210> SEQ ID NO 62
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 62
gcugugaaag uaacacguca augaaaggua accgcagc                                 38

<210> SEQ ID NO 63
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 63
gcugugaaag uaacacguca augaaaggua accacagc                                 38

<210> SEQ ID NO 64
<211> LENGTH: 38
<212> TYPE: DNA
<213> ORGANISM: artificial
<220> FEATURE:
<223> OTHER INFORMATION: synthetic
```

```
<220> FEATURE:
<221> NAME/KEY: misc_feature
<223> OTHER INFORMATION: L-RNA

<400> SEQUENCE: 64
gcuguaaaag uaacauguca augaaaggua acuacagc                              38

<210> SEQ ID NO 65
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 65
gcuguaaaag uaacaaguca augaaaggua acuacagc                              38

<210> SEQ ID NO 66
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 66
gcugugaaag uaacaaguca augaaaggua accacagc                              38

<210> SEQ ID NO 67
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 67
gcagugaaag uaacauguca augaaaggua accacagc                              38

<210> SEQ ID NO 68
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 68
gcugugaaag uaacauguca augaaaggua accacugc                              38

<210> SEQ ID NO 69
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
```

```
<400> SEQUENCE: 69
gcuaugaaag uaacauguca augaaaggua accauagc                              38

<210> SEQ ID NO 70
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 70
gcugcgaaag cgacauguca augaaaggua gccgcagc                              38

<210> SEQ ID NO 71
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 71
gcugugaaag caacauguca augaaaggua gccacagc                              38

<210> SEQ ID NO 72
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 72
gcugugaaag uaacauguca augaaaggua gccgcagc                              38

<210> SEQ ID NO 73
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 73
agcgugaaag uaacacguaa aaugaaaggu aaccacgcu                             39

<210> SEQ ID NO 74
<211> LENGTH: 27
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (16)..(16)
<223> OTHER INFORMATION: a or absent
```

```
<400> SEQUENCE: 74
aaagyracah gumaaaugaa agguarc                               27

<210> SEQ ID NO 75
<211> LENGTH: 26
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 75
aaagyracah gumaaugaaa gguarc                                26

<210> SEQ ID NO 76
<211> LENGTH: 27
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 76
aaagyracah gumaaaugaa agguarc                               27

<210> SEQ ID NO 77
<211> LENGTH: 26
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 77
aaagyaacah gucaaugaaa gguarc                                26

<210> SEQ ID NO 78
<211> LENGTH: 36
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 78
cugugaaagc aacaugucaa ugaaagguag ccgcag                     36

<210> SEQ ID NO 79
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 79
ugugaaagca acaugucaau gaaagguagc cgca                       34
```

```
<210> SEQ ID NO 80
<211> LENGTH: 32
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 80
gugaaagcaa caugucaaug aaagguagcc gc                                    32

<210> SEQ ID NO 81
<211> LENGTH: 30
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 81
ugaaagcaac augucaauga aagguagccg                                       30

<210> SEQ ID NO 82
<211> LENGTH: 28
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 82
gaaagcaaca ugucaaugaa agguagcc                                         28

<210> SEQ ID NO 83
<211> LENGTH: 26
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 83
aaagcaacau gucaaugaaa gguagc                                           26

<210> SEQ ID NO 84
<211> LENGTH: 36
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 84
gcgugaaagc aacaugucaa ugaaagguag ccgcgc                                36

<210> SEQ ID NO 85
<211> LENGTH: 36
<212> TYPE: DNA
<213> ORGANISM: artificial
```

<220> FEATURE:
<223> OTHER INFORMATION: synthetic
<220> FEATURE:
<221> NAME/KEY: misc_feature
<223> OTHER INFORMATION: L-RNA

<400> SEQUENCE: 85
gcgcgaaagc aacaugucaa ugaaagguag ccgcgc        36

<210> SEQ ID NO 86
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 86
gcggaaagca acaugucaau gaaagguagc ccgc        34

<210> SEQ ID NO 87
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 87
cgugaaagca acaugucaau gaaagguagc cgcg        34

<210> SEQ ID NO 88
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 88
gcgcaaagca acaugucaau gaaagguagc gugc        34

<210> SEQ ID NO 89
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 89
gugcaaagca acaugucaau gaaagguagc gcgc        34

<210> SEQ ID NO 90
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 90
cgcgaaagca acaugucaau gaaagguagc cgug					34

<210> SEQ ID NO 91
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 91
gggcaaagca acaugucaau gaaagguagc cccc					34

<210> SEQ ID NO 92
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 92
ggccaaagca acaugucaau gaaagguagc ggcc					34

<210> SEQ ID NO 93
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 93
gcccaaagca acaugucaau gaaagguagc gggc					34

<210> SEQ ID NO 94
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 94
ccccaaagca acaugucaau gaaagguagc gggg					34

<210> SEQ ID NO 95
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 95
gugcugcggg gguuagggcu agaagucggc cugcagcac         39

<210> SEQ ID NO 96
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 96
agcguggcga gguuagggcu agaagucggu cgacacgcu         39

<210> SEQ ID NO 97
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 97
guguugcgga gguuagggcu agaagucggu cagcagcac         39

<210> SEQ ID NO 98
<211> LENGTH: 48
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 98
cgugcggccu aagagguuag ggcuuaaagu cggucuuugg ccaacacg         48

<210> SEQ ID NO 99
<211> LENGTH: 48
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 99
cgugcgcuug agauaggggu uagggcuuaa agucggcuga uucucacg         48

<210> SEQ ID NO 100
<211> LENGTH: 48
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 100
cgugauuggu gaggggguuag ggcuugaagu cggccuuguc cagucacg         48

```
<210> SEQ ID NO 101
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 101
agcgugaagg gguuagggcu cgaagucggc ugacacgcu                    39

<210> SEQ ID NO 102
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 102
gugcugcggg gguuagggcu cgaagucggc ccgcagcac                    39

<210> SEQ ID NO 103
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 103
guguucccgg gguuagggcu ugaagucggc cggcagcac                    39

<210> SEQ ID NO 104
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 104
guguugcagg gguuagggcu ugaagucggc cugcagcac                    39

<210> SEQ ID NO 105
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 105
gugcugcggg gguuagggcu caaagucggc cugcagcac                    39

<210> SEQ ID NO 106
<211> LENGTH: 38
<212> TYPE: DNA
<213> ORGANISM: artificial
```

```
<220> FEATURE:
<223> OTHER INFORMATION: synthetic
<220> FEATURE:
<221> NAME/KEY: misc_feature
<223> OTHER INFORMATION: L-RNA

<400> SEQUENCE: 106
gugcugccgg gguuagggcu aaagucggcc gacagcac                          38

<210> SEQ ID NO 107
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 107
gugcuguggg ggucagggcu agaagucggc cugcagcac                         39

<210> SEQ ID NO 108
<211> LENGTH: 19
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (13)..(13)
<223> OTHER INFORMATION: A or absent

<400> SEQUENCE: 108
gguyagggcu hraagucgg                                               19

<210> SEQ ID NO 109
<211> LENGTH: 19
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 109
gguyagggcu hraagucgg                                               19

<210> SEQ ID NO 110
<211> LENGTH: 18
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 110
gguyagggcu hragucgg                                                18

<210> SEQ ID NO 111
<211> LENGTH: 19
<212> TYPE: DNA
<213> ORGANISM: artificial
```

```
<220> FEATURE:
<223> OTHER INFORMATION: synthetic
<220> FEATURE:
<221> NAME/KEY: misc_feature
<223> OTHER INFORMATION: L-RNA

<400> SEQUENCE: 111
gguuagggcu hgaagucgg                                                      19

<210> SEQ ID NO 112
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 112
ugagauaggg guuagggcuu aaagucggcu gauucuca                                 38

<210> SEQ ID NO 113
<211> LENGTH: 36
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 113
gagauagggg uuagggcuua aagucggcug auucuc                                   36

<210> SEQ ID NO 114
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 114
ggggguuagg cuuaaagucg gcugauucu                                           29

<210> SEQ ID NO 115
<211> LENGTH: 37
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 115
gcguggcgag guuagggcua gaagucgguc gacacgc                                  37

<210> SEQ ID NO 116
<211> LENGTH: 35
<212> TYPE: DNA
<213> ORGANISM: artificial
<220> FEATURE:
<223> OTHER INFORMATION: synthetic
```

```
<220> FEATURE:
<221> NAME/KEY: misc_feature
<223> OTHER INFORMATION: L-RNA

<400> SEQUENCE: 116
cguggcgagg uuagggcuag aagucggucg acacg                               35

<210> SEQ ID NO 117
<211> LENGTH: 33
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 117
cgggcgaggu uagggcuaga agucggucga ccg                                 33

<210> SEQ ID NO 118
<211> LENGTH: 33
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 118
cgggcgaggu uagggcuaga agucggucgc ccg                                 33

<210> SEQ ID NO 119
<211> LENGTH: 31
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 119
cggcgagguu agggcuagaa gucggucgcc g                                   31

<210> SEQ ID NO 120
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 120
cgggagguua gggcuagaag ucggucccg                                      29

<210> SEQ ID NO 121
<211> LENGTH: 27
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
```

```
<400> SEQUENCE: 121
gggagguuag ggcuagaagu cgguccc                                              27

<210> SEQ ID NO 122
<211> LENGTH: 27
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 122
ccgcgguuag ggcuagaagu cgggcgg                                              27

<210> SEQ ID NO 123
<211> LENGTH: 27
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 123
cccggguuag ggcuagaagu cggcggg                                              27

<210> SEQ ID NO 124
<211> LENGTH: 27
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 124
ggcggguuag ggcuagaagu cggcgcc                                              27

<210> SEQ ID NO 125
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 125
cccgcgguua gggcuagaag ucgggcggg                                            29

<210> SEQ ID NO 126
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 126
gccgcgguua gggcuagaag ucgggcggc                                            29
```

```
<210> SEQ ID NO 127
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 127 ccccgggguua gggcuagaag ucggcgggg                                           29

<210> SEQ ID NO 128
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 128 cggcgggguua gggcuagaag ucggcgccg                                           29

<210> SEQ ID NO 129
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 129 gggcgggguua gggcuagaag ucggcgccc                                           29

<210> SEQ ID NO 130
<211> LENGTH: 37
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 130
ugcugcgggg guuagggcua gaagucggcc ugcagca                                   37

<210> SEQ ID NO 131
<211> LENGTH: 35
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 131
gcugcggggg uuagggcuag aagucggccu gcagc                                     35

<210> SEQ ID NO 132
<211> LENGTH: 33
<212> TYPE: DNA
<213> ORGANISM: artificial
```

<220> FEATURE:
<223> OTHER INFORMATION: synthetic
<220> FEATURE:
<221> NAME/KEY: misc_feature
<223> OTHER INFORMATION: L-RNA

<400> SEQUENCE: 132
cugcgggggu uagggcuaga agucggccug cag                33

<210> SEQ ID NO 133
<211> LENGTH: 31
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 133
ugcggggguu agggcuagaa gucggccugc a                  31

<210> SEQ ID NO 134
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 134
gcggggguua gggcuagaag ucggccugc                     29

<210> SEQ ID NO 135
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 135 gccggggguua gggcuagaag ucggccggc                    29

<210> SEQ ID NO 136
<211> LENGTH: 31
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 136
ggccgggguu agggcuagaa gucggccggc c                  31

<210> SEQ ID NO 137
<211> LENGTH: 31
<212> TYPE: DNA
<213> ORGANISM: artificial
<220> FEATURE:
<223> OTHER INFORMATION: synthetic

```
<220> FEATURE:
<221> NAME/KEY: misc_feature
<223> OTHER INFORMATION: L-RNA

<400> SEQUENCE: 137
cgccgggguu agggcuagaa gucggccggc g                                          31

<210> SEQ ID NO 138
<211> LENGTH: 10
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (7)..(7)
<223> OTHER INFORMATION: n is a, c, g, t or u

<400> SEQUENCE: 138 rksbusnvgr                                                                  10

<210> SEQ ID NO 139
<211> LENGTH: 10
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (3)..(3)
<223> OTHER INFORMATION: n is a, c, g, t or u

<400> SEQUENCE: 139 yynrcassmy                                                                  10

<210> SEQ ID NO 140
<211> LENGTH: 10
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 140 rksbugsvgr                                                                  10

<210> SEQ ID NO 141
<211> LENGTH: 10
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (3)..(3)
<223> OTHER INFORMATION: n is a, c, g, t or u

<400> SEQUENCE: 141 ycnrcassmy                                                                  10
```

```
<210> SEQ ID NO 142
<211> LENGTH: 48
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 142
cgugguccgu ugugucaggu cuauucgccc cggugcaggg cauccgcg                    48

<210> SEQ ID NO 143
<211> LENGTH: 49
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 143
gcagugugac gcggacguga uaggacagag cugaucccgc ucaggugag                   49

<210> SEQ ID NO 144
<211> LENGTH: 49
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 144
caacagcagu gugacgcgga cgugauagga cagagcugau cccgcucag                   49

<210> SEQ ID NO 145
<211> LENGTH: 36
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (1)..(1)
<223> OTHER INFORMATION: 40 kDa-PEG-moiety attached to 5'-end

<400> SEQUENCE: 145
gcgugaaagc aacaugucaa ugaaagguag ccgcgc                                 36

<210> SEQ ID NO 146
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 146
gcugugaaag caacauguca augaaaggua gccgcagc                               38
```

```
<210> SEQ ID NO 147
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 147
gcugugaaag uaacauguca augaaaggua accacagc                              38

<210> SEQ ID NO 148
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 148
gcugugaaag uaacacguca augaaaggua accgcagc                              38

<210> SEQ ID NO 149
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 149
gcugugaaag uaacacguca augaaaggua accacagc                              38

<210> SEQ ID NO 150
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 150
gcuguaaaag uaacauguca augaaaggua acuacagc                              38

<210> SEQ ID NO 151
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 151
gcuguaaaag uaacaaguca augaaaggua acuacagc                              38

<210> SEQ ID NO 152
<211> LENGTH: 38
<212> TYPE: DNA
<213> ORGANISM: artificial
```

```
<220> FEATURE:
<223> OTHER INFORMATION: synthetic
<220> FEATURE:
<221> NAME/KEY: misc_feature
<223> OTHER INFORMATION: D-RNA

<400> SEQUENCE: 152
gcugugaaag uaacaaguca augaaaggua accacagc                              38

<210> SEQ ID NO 153
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 153
gcagugaaag uaacauguca augaaaggua accacagc                              38

<210> SEQ ID NO 154
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 154
gcugugaaag uaacauguca augaaaggua accacugc                              38

<210> SEQ ID NO 155
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 155
gcuaugaaag uaacauguca augaaaggua accauagc                              38

<210> SEQ ID NO 156
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 156
gcugcgaaag cgacauguca augaaaggua gccgcagc                              38

<210> SEQ ID NO 157
<211> LENGTH: 38
<212> TYPE: DNA
<213> ORGANISM: artificial
<220> FEATURE:
<223> OTHER INFORMATION: synthetic
```

```
<220> FEATURE:
<221> NAME/KEY: misc_feature
<223> OTHER INFORMATION: D-RNA

<400> SEQUENCE: 157
gcugugaaag caacauguca augaaaggua gccacagc                                   38

<210> SEQ ID NO 158
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 158
gcugugaaag uaacauguca augaaaggua gccgcagc                                   38

<210> SEQ ID NO 159
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 159
agcgugaaag uaacacguaa aaugaaaggu aaccacgcu                                  39

<210> SEQ ID NO 160
<211> LENGTH: 36
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 160
cugugaaagc aacaugucaa ugaaagguag ccgcag                                     36

<210> SEQ ID NO 161
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 161
ugugaaagca acaugucaau gaaagguagc cgca                                       34

<210> SEQ ID NO 162
<211> LENGTH: 32
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA
```

<400> SEQUENCE: 162
gugaaagcaa caugucaaug aaagguagcc gc          32

<210> SEQ ID NO 163
<211> LENGTH: 30
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 163
ugaaagcaac augucaauga aagguagccg          30

<210> SEQ ID NO 164
<211> LENGTH: 28
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 164
gaaagcaaca ugucaaugaa agguagcc          28

<210> SEQ ID NO 165
<211> LENGTH: 26
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 165
aaagcaacau gucaaugaaa gguagc          26

<210> SEQ ID NO 166
<211> LENGTH: 36
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 166
gcgugaaagc aacaugucaa ugaaagguag ccgcgc          36

<210> SEQ ID NO 167
<211> LENGTH: 36
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 167
gcgcgaaagc aacaugucaa ugaaagguag ccgcgc          36

```
<210> SEQ ID NO 168
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 168
gcggaaagca acaugucaau gaaaggaugc ccgc                              34

<210> SEQ ID NO 169
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 169
cgugaaagca acaugucaau gaaaggaugc cgcg                              34

<210> SEQ ID NO 170
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 170
gcgcaaagca acaugucaau gaaaggaugc gugc                              34

<210> SEQ ID NO 171
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 171
gugcaaagca acaugucaau gaaaggaugc gcgc                              34

<210> SEQ ID NO 172
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 172
cgcgaaagca acaugucaau gaaaggaugc cgug                              34

<210> SEQ ID NO 173
<211> LENGTH: 34
<212> TYPE: DNA
<213> ORGANISM: artificial
```

```
<220> FEATURE:
<223> OTHER INFORMATION: synthetic
<220> FEATURE:
<221> NAME/KEY: misc_feature
<223> OTHER INFORMATION: D-RNA

<400> SEQUENCE: 173
gggcaaagca acaugucaau gaaagguagc gccc                          34

<210> SEQ ID NO 174
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 174
ggccaaagca acaugucaau gaaagguagc ggcc                          34

<210> SEQ ID NO 175
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 175
gcccaaagca acaugucaau gaaagguagc gggc                          34

<210> SEQ ID NO 176
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 176
ccccaaagca acaugucaau gaaagguagc gggg                          34

<210> SEQ ID NO 177
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 177
gugcugcggg gguuagggcu agaagucggc cugcagcac                     39

<210> SEQ ID NO 178
<211> LENGTH: 39
<212> TYPE: DNA
<213> ORGANISM: artificial
<220> FEATURE:
<223> OTHER INFORMATION: synthetic
```

<220> FEATURE:
<221> NAME/KEY: misc_feature
<223> OTHER INFORMATION: D-RNA

<400> SEQUENCE: 178
agcguggcga gguuagggcu agaagucggu cgacacgcu                                39

<210> SEQ ID NO 179
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 179
guguugcgga gguuagggcu agaagucggu cagcagcac                                39

<210> SEQ ID NO 180
<211> LENGTH: 48
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 180
cgugcggccu aagagguuag ggcuuaaagu cggucuuugg ccaacacg                      48

<210> SEQ ID NO 181
<211> LENGTH: 48
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 181
cgugcgcuug agauaggggu uagggcuuaa agucggcuga uucucacg                      48

<210> SEQ ID NO 182
<211> LENGTH: 48
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 182
cgugauuggu gaggggguuag ggcuugaagu cggccuuguc cagucacg                     48

<210> SEQ ID NO 183
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 183
agcgugaagg gguuagggcu cgaagucggc ugacacgcu 39

<210> SEQ ID NO 184
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 184
gugcugcggg gguuagggcu cgaagucggc ccgcagcac 39

<210> SEQ ID NO 185
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 185
guguucccgg gguuagggcu ugaagucggc cggcagcac 39

<210> SEQ ID NO 186
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 186
guguugcagg gguuagggcu ugaagucggc cugcagcac 39

<210> SEQ ID NO 187
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 187
gugcugcggg gguuagggcu caaagucggc cugcagcac 39

<210> SEQ ID NO 188
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 188
gugcugccgg gguuagggcu aaagucggcc gacagcac 38

```
<210> SEQ ID NO 189
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 189
gugcuguggg ggucagggcu agaagucggc cugcagcac                              39

<210> SEQ ID NO 190
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 190
ugagauaggg guuagggcuu aaagucggcu gauucuca                               38

<210> SEQ ID NO 191
<211> LENGTH: 36
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 191
gagauagggg uuagggcuua aagucggcug auucuc                                 36

<210> SEQ ID NO 192
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 192 ggggguuaggg cuuaaagucg gcugauucu                                        29

<210> SEQ ID NO 193
<211> LENGTH: 37
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 193
gcguggcgag guuagggcua gaagucgguc gacacgc                                37

<210> SEQ ID NO 194
<211> LENGTH: 35
<212> TYPE: DNA
<213> ORGANISM: artificial
```

<220> FEATURE:
<223> OTHER INFORMATION: synthetic
<220> FEATURE:
<221> NAME/KEY: misc_feature
<223> OTHER INFORMATION: D-RNA

<400> SEQUENCE: 194
cguggcgagg uuagggcuag aagucggucg acacg                              35

<210> SEQ ID NO 195
<211> LENGTH: 33
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 195
cgggcgaggu uagggcuaga agucggucga ccg                                33

<210> SEQ ID NO 196
<211> LENGTH: 33
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 196
cgggcgaggu uagggcuaga agucggucgc ccg                                33

<210> SEQ ID NO 197
<211> LENGTH: 31
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 197
cggcgagguu agggcuagaa gucggucgcc g                                  31

<210> SEQ ID NO 198
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 198
cgggagguua gggcuagaag ucgucccg                                      29

<210> SEQ ID NO 199
<211> LENGTH: 27
<212> TYPE: DNA
<213> ORGANISM: artificial
<220> FEATURE:
<223> OTHER INFORMATION: synthetic

```
<220> FEATURE:
<221> NAME/KEY: misc_feature
<223> OTHER INFORMATION: D-RNA

<400> SEQUENCE: 199
gggagguuag ggcuagaagu cgguccc                                          27

<210> SEQ ID NO 200
<211> LENGTH: 27
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 200
ccgcgguuag ggcuagaagu cgggcgg                                          27

<210> SEQ ID NO 201
<211> LENGTH: 27
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 201
cccggguuag ggcuagaagu cggcggg                                          27

<210> SEQ ID NO 202
<211> LENGTH: 27
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 202
ggcggguuag ggcuagaagu cggcgcc                                          27

<210> SEQ ID NO 203
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 203
cccgcgguua gggcuagaag ucgggcggg                                        29

<210> SEQ ID NO 204
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA
```

```
<400> SEQUENCE: 204
gccgcgguua gggcuagaag ucgggcggc                                29

<210> SEQ ID NO 205
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 205
ccccggguua gggcuagaag ucggcgggg                                29

<210> SEQ ID NO 206
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 206
cggcggguua gggcuagaag ucggcgccg                                29

<210> SEQ ID NO 207
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 207
gggcggguua gggcuagaag ucggcgccc                                29

<210> SEQ ID NO 208
<211> LENGTH: 37
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 208
ugcugcgggg guuagggcua gaagucggcc ugcagca                       37

<210> SEQ ID NO 209
<211> LENGTH: 35
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 209
gcugcggggg uuagggcuag aagucggccu gcagc                         35
```

```
<210> SEQ ID NO 210
<211> LENGTH: 33
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 210
cugcgggggu uagggcuaga agucggccug cag                                    33

<210> SEQ ID NO 211
<211> LENGTH: 31
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 211 ugcgggggu u agggcuagaa gucggccugc a                                     31

<210> SEQ ID NO 212
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 212
gcggggguua gggcuagaag ucggccugc                                         29

<210> SEQ ID NO 213
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 213 gccggggguua gggcuagaag ucggccggc                                        29

<210> SEQ ID NO 214
<211> LENGTH: 31
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 214
ggccgggguu agggcuagaa gucggccggc c                                      31

<210> SEQ ID NO 215
<211> LENGTH: 31
<212> TYPE: DNA
<213> ORGANISM: artificial
```

```
<220> FEATURE:
<223> OTHER INFORMATION: synthetic
<220> FEATURE:
<221> NAME/KEY: misc_feature
<223> OTHER INFORMATION: D-RNA

<400> SEQUENCE: 215 cgccggggu agggcuagaa gucggccggc g                                    31

<210> SEQ ID NO 216
<211> LENGTH: 48
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 216
cgugguccgu ugugucaggu cuauucgccc cggugcaggg cauccgcg                 48

<210> SEQ ID NO 217
<211> LENGTH: 49
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 217
gcagugugac gcggacguga uaggacagag cugaucccgc ucaggugag                49

<210> SEQ ID NO 218
<211> LENGTH: 49
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 218
caacagcagu gugacgcgga cgugauagga cagagcugau cccgcucag                49

<210> SEQ ID NO 219
<211> LENGTH: 40
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (1)..(1)
<223> OTHER INFORMATION: 40 kDa-PEG-moiety attached to 5'-end

<400> SEQUENCE: 219
uaaggaaacu cggucugaug cgguagcgcu gugcagagcu                          40

<210> SEQ ID NO 220
<211> LENGTH: 17
<212> TYPE: DNA
<213> ORGANISM: artificial
```

```
<220> FEATURE:
<223> OTHER INFORMATION: synthetic
<220> FEATURE:
<221> NAME/KEY: misc_feature
<223> OTHER INFORMATION: L-RNA

<400> SEQUENCE: 220
cgugcgcuug agauagg                                                    17

<210> SEQ ID NO 221
<211> LENGTH: 12
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 221
cugauucuca cg                                                         12

<210> SEQ ID NO 222
<211> LENGTH: 10
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 222
cugauucuca                                                            10

<210> SEQ ID NO 223
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (1)..(1)
<223> OTHER INFORMATION: 40 kDa-PEG-moiety attached to 5'-end

<400> SEQUENCE: 223
gccgggguua gggcuagaag ucggccggc                                       29

<210> SEQ ID NO 224
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (1)..(1)
<223> OTHER INFORMATION: 40 kDa-PEG-moiety attached to 5'-end

<400> SEQUENCE: 224
cgggagguua gggcuagaag ucggucccg                                       29
```

```
-continued

<210> SEQ ID NO 225
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (1)..(1)
<223> OTHER INFORMATION: 40 kDa-PEG-moiety attached to 5'-end

<400> SEQUENCE: 225
cgcauggacu gauccuaguc gguuauguag aucuagugug gugcg                45
```